United States Patent
Kinney et al.

(10) Patent No.: US 9,169,298 B2
(45) Date of Patent: *Oct. 27, 2015

(54) DENGUE SEROTYPE 1 ATTENUATED STRAIN

(75) Inventors: Richard Kinney, Fort Collins, CO (US); Claire Y. H. Kinney, Fort Collins, CO (US); Véronique Barban, Craponne (FR); Jean Lang, Mions (FR); Bruno Guy, Lyons (FR)

(73) Assignees: Sanofi Pasteur, Lyons (FR); Centers for Disease Control and Prevention, Atlanta, GA (US)

( * ) Notice: Subject to any disclaimer, the term of this patent is extended or adjusted under 35 U.S.C. 154(b) by 810 days.

This patent is subject to a terminal disclaimer.

(21) Appl. No.: 13/281,240

(22) Filed: Oct. 25, 2011

(65) Prior Publication Data

US 2012/0083584 A1 Apr. 5, 2012

Related U.S. Application Data

(60) Continuation of application No. 12/633,411, filed on Dec. 8, 2009, now Pat. No. 8,067,565, which is a division of application No. 11/449,876, filed on Jun. 9, 2006, now Pat. No. 7,641,907.

(60) Provisional application No. 60/691,243, filed on Jun. 17, 2005.

(51) Int. Cl.
*A61K 39/12* (2006.01)
*C07K 14/005* (2006.01)
*C12N 7/00* (2006.01)
*A61K 39/00* (2006.01)

(52) U.S. Cl.
CPC ............... *C07K 14/005* (2013.01); *A61K 39/12* (2013.01); *C12N 7/00* (2013.01); *A61K 2039/5254* (2013.01); *A61K 2039/545* (2013.01); *C12N 2770/24121* (2013.01); *C12N 2770/24122* (2013.01); *C12N 2770/24134* (2013.01); *C12N 2770/24164* (2013.01)

(58) Field of Classification Search
None
See application file for complete search history.

(56) References Cited

U.S. PATENT DOCUMENTS

2004/0137013 A1 7/2004 Katinger et al.

FOREIGN PATENT DOCUMENTS

| EP | 1159968 A1 | 12/2001 |
|---|---|---|
| WO | WO-96/40933 A1 | 12/1996 |
| WO | WO-00/57907 A2 | 10/2000 |
| WO | WO-01/60847 A2 | 8/2001 |
| WO | WO-02/095075 A1 | 11/2002 |
| WO | WO-03/092592 A2 | 11/2003 |

OTHER PUBLICATIONS

Database EMBL (online) Sep. 18, 2002, "Dengue virus type 1 recombinant clone RDEN1, complete genome." XP002397884 retrieved from EBI accession No. EM_PRO:AY145121, Database accession No. AY145121 nt 5962->A.

Butrapet et al., "Attenuation markers of a candidate dengue type 2 vaccine virus, strain 16681 (PDK-53), are defined by mutations in the 5' noncoding region and nonstructural proteins 1 and 3," J Virol. 74(7):3011-9 (2000).

Gowen et al., "Animal models of highly pathogenic RNA viral infections: hemorrhagic fever viruses," Antiviral Res. 78(1):79-90 (2008).

Huang et al., "Chimeric dengue type 2 (vaccine strain PDK-53)/ dengue type 1 virus as a potential candidate dengue type 1 virus vaccine," J Virol. 74(7):3020-8 (2000).

Kinney et al., "Construction of infectious cDNA clones for dengue 2 virus: strain 16681 and its attenuated vaccine derivative, strain PDK-53," Virology. 230(2):300-8 (1997).

Kinney et al., "Development of new vaccines against dengue fever and Japanese encephalitis," Intervirology. 44(2-3):176-97 (2001).

Montagnon et al., "Experience with vero cells at Pasteur Mérieux Connaught developments in biological standardization," Dev Biol Stand. 98:137-40 (1997).

GenBank: AF180818.1, Dengue virus type 1 strain 16007 (PDK-13) polyprotein precursor, mRNA, complete CDS, retrieved on Dec. 5, 2013 (5 pages).

Putnak et al., "Development of a purified, inactivated, dengue-2 virus vaccine prototype in Vero cells: immunogenicity and protection in mice and rhesus monkeys," J Infect Dis. 174(6):1176-84 (1996).

Sanchez et al., "Innate and adaptive cellular immunity in flavivirus-naïve human recipients of a live-attenuated dengue serotype 3 vaccine produced in Vero cells (VDV3)," Vaccine. 24(23):4914-26 (2006).

*Primary Examiner* — Stacy B Chen
(74) *Attorney, Agent, or Firm* — Clark & Elbing LLP; Susan M. Michaud

(57) ABSTRACT

The invention relates to live attenuated VDV1 (VERO-Derived Dengue serotype 1 virus) strains which have been derived from the wild-type dengue-1 strain 16007 by passaging on PDK and sanitization on Vero cells and nucleic acids th strain 16007 (Day 7)

VDV1 (Day 7)

LAV1 (Day 7)

DENGUE SEROTYPE 1 ATTENUATED STRAIN

CROSS-REFERENCE TO RELATED APPLICATIONS

The present application is a continuation of U.S. application Ser. No. 12/633,411, filed Dec. 8, 2009 now U.S. Pat. No. 8,067,565, which is a divisional of U.S. application Ser. No. 11/449,876, filed Jun. 9, 2006 now U.S. Pat. No. 7,641,907, which claims the benefit of U.S. provisional application 60/691,243, filed on Jun. 17, 2005, all of said applications incorporated herein by reference.

The invention relates to new live attenuated VDV1 (VERO-Derived Dengue serotype 1 virus) strains which are derived from the wild-type dengue-1 strain 16007 by passaging on PDK and Vero cells, and sanitization. The invention further relates to a vaccine composition which comprises such VDV1 strain.

Dengue diseases are caused by four closely related, but antigenically distinct, virus serologic types (Gubler, 1988; Kautner et al., 1997; Rigau-Pérez et al., 1998; Vaughn et al., 1997), of the genus Flavivirus (Gubler, 1988). Infection with a dengue virus serotype can produce a spectrum of clinical illnesses ranging from a non-specific viral syndrome to severe, fatal haemorrhagic disease. The incubation period of dengue fever (DF) after the mosquito bite averages 4 days (range 3-14 days). DF is characterised by biphasic fever, headache, pain in various parts of the body, prostration, rash, lymphadenopathy and leukopenia (Kautner et al., 1997; Rigau-Pérez et al., 1998). The viremic period is the same as of febrile illness (Vaughn et al., 1997). Recovery from DF is usually complete in 7 to 10 days but prolonged asthenia is common. Leukocytes and platelets counts decreases are frequent.

Dengue haemorrhagic fever (DHF) is a severe febrile disease characterised by abnormalities of homeostasis and increased vascular permeability that can lead to hypovolemia and hypotension (dengue shock syndrome, DSS) often complicated by severe internal bleeding. The case fatality rate of DHF can be as high as 10% without therapy, but below 1% in most centres with therapeutic experience (WHO Technical Guide, 1986).

Routine laboratory diagnosis of dengue infections are based on virus isolation and/or the detection of dengue virus-specific antibodies.

Dengue disease is the second most important tropical infectious disease after malaria, with over half of the world's population (2.5 billion) living in areas at risk for epidemic transmission. An estimated 50 to 100 million cases of dengue, 500,000 hospitalised DHF patients and 25,000 deaths occur each year. Dengue is endemic in Asia, the Pacific, Africa, Latin America, and the Caribbean. More than 100 tropical countries have endemic dengue virus infections, and DHF have been documented in more than 60 of these (Gubler, 2002; Monath, 1994). A number of well described factors appear to be involved in dengue infections: population growth, unplanned and uncontrolled urbanisation particularly in association with poverty, increased air travel, lack of effective mosquito control, and the deterioration of sanitary and public health infrastructure (Gubler, 2002). The awareness of dengue in travellers and expatriates is increasing (Shirtcliffe et al., 1998). Dengue has proven to be a major cause of febrile illness among US troops during deployments in dengue-endemic tropical areas (DeFraites et al., 1994).

The viruses are maintained in a cycle that involves humans and *Aedes aegypti*, a domestic, day-biting mosquito that prefers to feed on humans. Human infection is initiated by the injection of virus during blood feeding by an infected *Aedes aegypti* mosquito. Salivary virus is deposited mainly in the extravascular tissues. The primary cell subset infected after inoculation is dendritic cells, which subsequently migrate to draining lymph nodes (Wu et al., 2000). After initial replication in the skin and draining lymph nodes, virus appears in the blood during the acute febrile phase, generally for 3 to 5 days.

Monocytes and macrophages are with dendritic cells among the primary target of dengue virus. Protection against homotypic reinfection is complete and probably lifelong, but cross-protection between dengue types lasts less than 12 weeks (Sabin, 1952). Consequently a subject can experience a second infection with a different serotype. A second dengue infection is a theoretical risk factor of developing severe dengue disease. However, DHF is multifactorial including: the strain of the virus involved, as well as the age, immune status, and genetic predisposition of the patient. Two factors play a major role in the occurrence of DHF: a rapid viral replication with high viremia (the severity of the disease being related to the level of viremia (Vaughn et al., 2000) and an important inflammatory response with release of high levels of inflammatory mediators (Rothman and Ennis, 1999).

There is no specific treatment against Dengue diseases. The management of DF is supportive with bed rest, control of fever and pain with antipyretics and analgesics, and adequate fluid intake. The treatment of DHF needs correction of fluid loss, replacement of coagulation factors, and infusion of heparin.

Preventive measures presently rely on vector control and personal protection measures, which are difficult to enforce and expensive. No vaccine against dengue is currently registered. Since the 4 serotypes of dengue are circulating worldwide and since they are reported to be involved in cases of DHF, vaccination should ideally confer protection against all 4 dengue virus serotypes.

Live attenuated vaccines (LAVs), which reproduce natural immunity, have been used for the development of vaccines against many diseases, including some viruses belonging to the same genus as dengue (examples of commercially available flavivirus live-attenuated vaccines include yellow fever and Japanese encephalitis vaccines). The advantages of live-attenuated virus vaccines are their capacity of replication and induction of both humoral and cellular immune responses. In addition, the immune response induced by a whole virion vaccine against the different components of the virus (structural and non-structural proteins) reproduced those induced by natural infection.

A dengue vaccine project was initiated in Thailand at the Centre for Vaccine Development, Institute of Sciences and Technology for Development Mahidol University. Candidate live-attenuated vaccines were successfully developed, at a laboratory scale, for dengue serotype 1 (strain 16007, passage 13=LAV1), serotype 2 (strain 16681, passage 53), and serotype 4 (strain 1036, passage 48) viruses in Primary Dog Kidney (PDK) Cells, and for serotype 3 (strain 16562) in Primary Green Monkey Kidney (PGMK) cells (passage 30) and Fetal Rhesus Lung (FRhL) cells (passage 3). These vaccines have been tested as monovalent (single serotype), bivalent (two serotypes), trivalent (three serotypes), and tetravalent (all four serotypes) vaccines in Thai volunteers. Those vaccines were found to be safe and immunogenic in children and in adults (Gubler, 1997). These LAV 1-4 strains have been described in EP 1159968 in the name of the Mahidol University and were deposited before the CNCM (CNCM I-2480; CNCM I-2481; CNCM I-2482 and CNCM I-2483 respectively).

The complete sequence of the Dengue 1 Live-Attenuated Virus strain (LAV1) was established by R. Kinney et al. (CDC, Fort Collins). Sequence differences between parent DEN-1 strain 16007 (SEQ ID No.2) and LAV1 (SEQ ID No.3) strain are described in Table 1. Thus, genetic comparison of the wild-type virus strain 16007 and LAV1 strain showed a set of 14 point mutations which could be linked to LAV1 attenuation.

TABLE 1

DEN-1 16007 and DEN-1 16007/PDK13 (LAV1) Sequence Differences

| Coordinates | | LAV1 (DEN-1 16007/PDK13) | | 16007 | |
|---|---|---|---|---|---|
| Gene-aa | position | Nt | aa | nt | aa |
| E-130 | Nt-1323 | C | Ala | T | Val |
| E-203 | Nt-1541 | A | Lys | G | Glu |
|  | Nt-1543 | G |  | A |  |
| E-204 | Nt-1545 | A | Lys | G | Arg |
| E-211 | Nt-1567 | G | Gln | A | Gln |
| E-225 | Nt-1608 | T | Leu | C | Ser |
| E-477 | Nt-2363 | G | Val | A | Met |
| NS1-92 | Nt-2695 | C | Asp | T | Asp |
| NS1-121 | Nt-2782 | T | Ala | C | Ala |
| NS3-182 | Nt-5063 | A | Lys | G | Glu |
| NS3-510 | Nt-6048 | T | Phe | A | Tyr |
| NS4A-144 | Nt-6806 | G | Val | A | Met |
| NS4B-168 | Nt-7330 | G | Gln | A | Gln |
| NS5-624 | Nt-9445 | T | Ser | C | Ser |

Nucleotide changes modifying the corresponding codon are indicated in bold.

The LAV1 strain which was initially established in 1983 was further rapidly identified as potential vaccine candidate (Bhamarapravati and Yoksan, 1997).

However, at that time, transmission to humans of Spongiform Encephalitis through mammalian cultures was not perceived as a risk and the virus was routinely maintained in Primary Dog Kidney cells (PDK). Furthermore, this LAV1 strain corresponds to a heterogeneous population. This heterogeneity represents an additional risk due to a potential in vitro or in vivo selection of one of the strain present in the composition.

In view of these increasing concerns, the Applicant decided to set up a sanitization process in order to get rid of any such risks. By first transferring the LAV1 vaccine strain from PDK to VERO cells and then transfecting Vero cells with the purified genomic RNA of LAV1, followed by two successive steps of virus plaque purification the Applicant produced a new Vero-Derived serotype 1 virus (VDV1).

This new VDV1 strain which has been thus derived by transfer to VERO cells and biological cloning differs from the LAV1 strain by sequence, an homogenous plaque size and temperature sensitivity but importantly has conserved some phenotypic and genotypic features of the LAV1 such as e.g. attenuation spots, small plaque phenotype, growth restriction at high temperature, and has conserved the immunogenic features of the LAV1 strains. These features make this new strain a valuable vaccine candidate for prophylactic immunization in humans.

DEFINITIONS

"Dengue viruses" are positive-sense, single-stranded RNA viruses belonging to the Flavivirus genus of the flaviridae family. In the case of dengue serotype 1 (DEN-1) strain 16007, the entire sequence is 10735 nucleotides long (SEQ ID No.2). The RNA genome contains a type I cap at the 5'-end but lacks a 3'-end poly (A)-tail. The gene organization is 5'-noncoding region (NCR), structural protein (capsid (C), premembrane/membrane (prM/M), envelope (E)) and non structural protein (NS1-NS2A-NS2B-NS3-NS4A-NS4B-NS5) and 3' NCR. The viral RNA genome is associated with the C proteins to form nucleocapsid (icosahedral symmetry). As with other flaviviruses, the DEN viral genome encodes the uninterrupted open reading frame (ORF) which is translated to a single polyprotein.

Serial passaging of a virulent (disease-causing) strain of dengue-1 results in the isolation of modified virus which are "live attenuated", i.e., infectious, yet not capable of causing disease. These modified viruses are usually tested in monkeys to evaluate their attenuation. However, Humans are the only primates that exhibit signs of clinical disease. The viruses that cause mild (i.e. acceptable in terms of regulatory purposes as presenting a positive benefit/risk ratio) to low or no secondary effects (i.e. systemic events and/or biological abnormalities and/or local reactions) in the majority of the tested humans but still infect and induce an immune response are called "live attenuated".

The term "LAV" denotes live attenuated Dengue viral strains. In the context of the invention "LAVs" are live attenuated strains initially derived from the Dengue serotype 1 (DEN-1) strain 16007 by passages, e.g. 10, 11, 12 or 13 passages, in Primary Dog Kidney (PDK) Cells. For instance "LAV1/PDK13" is the attenuated strain established after 13 passages of strain 16007 in PDK cells (also named DEN-1 16007/PDK13). LAV1/PDK13 nucleotide sequence is shown in SEQ ID No.3.

"VDV1" is meant a LAV obtainable by the sanitization process disclosed in the present application. A VDV1 is thus a biological clone (homogeneous) VERO-adapted Dengue serotype 1 virus capable of inducing a specific humoral immune response including neutralizing antibodies in primate especially in humans. The VDV1 strains of the invention can be easily reconstructed starting directly from the here disclosed VDV1 sequences. The induction of a specific humoral immune response can be easily determined by an ELISA assay. The presence of neutralising antibody in the serum of a vaccinee is evaluated by the plaque reduction neutralization test as described in section 4.1.2.2. A serum is considered to be positive for the presence of neutralizing antibodies when the neutralizing antibody titer thus determined is at least superior or equal to 1:10.

The terms "mutation" means any detectable change in genetic material, e.g. DNA, RNA, cDNA, or any process, mechanism, or result of such a change. Mutations include substitutions of one or more nucleotides. In the context of the instant application, mutations identified in dengue-1 virus genomic sequence or polyprotein are designated pursuant to the nomenclature of Dunnen and Antonarakis (2000). As defined by Dunnen and Antonarakis at the nucleic acid level, substitutions are designated by ">", e.g. "31A>G" denotes that at nucleotide 31 of the reference sequence a A is changed to a G.

Variations at the protein level describe the consequence of the mutation and are reported as follows. Stop codons are designated by X (e.g. R97X denotes a change of Arg96 to a termination codon). Amino acid substitutions are designated for instant by "S9G", which means that Ser in position 9 is replaced by Gly.

VERO-Derived Dengue Serotype 1 Viruses (VDV1)

The composition of the previously developed dengue-1 vaccine candidate LAV1 was improved by a sanitization process.

The VERO-Derived Dengue serotype 1 viruses (VDV1) disclosed herein use the DEN-1 16007 virus attenuated by serial passages on PDK cells. VDV1 contains the whole genomic sequence of the live-attenuated DEN-1 virus, and bears the same spots which have been linked to attenuation as the original LAV1 strain that was tested in humans.

Sanitization of the LAV1 vaccine candidate was performed by removing proteins and introducing only purified viral genomic material into Vero cells. More specifically, sanitization of the strain was performed in 2 steps:

1) Amplification of DEN16007/PDK11 (LAV1/PDK11) on Vero cells, at 32° C.
2) Purification and transfection of viral RNA into Vero cells.

Step 1 has been carried out by one passage of LAV1/PDK11 on Vero cells. For that purpose, Vero cells were infected with LAV1/PDK11 at a moi of 0.01 and incubated at 32° C. for 5 days.

For step 2, advantage was taken of the fact that the viral genome is an infectious RNA, which means that it is able, when introduced into a cell, to reconstitute a complete infectious virus. The second purification and transfection step thus comprised the steps consisting of:
  a) extracting and purifying viral RNA from plaque-purified viruses;
  b) advantageously associating of the purified RNA with cationic lipids;
  c) transfecting Vero cell, in particular Vero cell LS10;
  d) recovering of the neo-synthesized viruses; and
  e) purifying a VDV strain by plaque purification and optionally amplifying it in host cells, especially Vero cells.

The Vero cell technology is a well-known technology which has been used for different commercial products (injectable and oral polio vaccines, rabies vaccine). In the present invention qualified Vero cells were advantageously used to guarantee the absence of any risks potentially linked to the presence of adventitious agents. By "qualified VERO cells" is meant cells or cell lines for which culture conditions are known and is such that the said cells are free from any adventitious agents. These include e.g. the VERO cell LS10 of Sanofi Pasteur.

The thus isolated VDV strains are classically stored either in the form of a freezed composition or in the form of a lyophilised product. For that purpose, the VDV can be mixed with a diluent classically a buffered aqueous solution comprising cryoprotective compounds such a sugar alcohol and stabilizer. The pH before freezing or lyophilisation is advantageously settled in the range of 6 to 9, e.g. around 7 such as a pH of 7.5+/−0.2 as determined by a pH meter at RT. Before use, the lyophilised product is mixed with a pharmaceutical diluent or excipient such as a sterile NaCl 4% solution to reconstitute a liquid immunogenic composition or vaccine.

Sequencing, at attenuation-specific loci, of virus recovered after transfection, did not reveal any mutation, compared to the LAV1/PDK13 strain. The biologically cloned VDV1 virus exhibits a homogenous plaque phenotype and a remarkable genetic stability with regard to its LAV1 parent as it can be deduced especially from the conservation of the attenuation genotype.

VDV1 strain was sequenced and compared with the serotype 1 Dengue Live Attenuated Virus (LAV1/PDK13) strain sequence (SEQ ID No 3). A set of 3 nucleotide differences was found with regard to the reference LAV1 sequence. One of them is silent at the amino acid level (position 2719). The two others (positions 5962 and 7947) are located in non-structural peptides coding sequences (NS3-481 and NS5-125, respectively). None of these differences corresponds to any of the LAV1 attenuation positions.

The invention thus provides for live attenuated dengue-1 virus strains that have been obtained from the wild type virus DEN-1 16007 attenuated by serial passages on PDK cells and then by passage and sanitization on VERO cells. In particular the attenuated strains of the invention comprise at least the identified sequence mutations (non-silent and optionally silent) relative to the nucleotide sequence or polyprotein sequence of the wild-type DEN-1 16007 and LAV1/PDK13 strains.

Accordingly, the invention relates to an isolated live attenuated dengue-1 virus strain which comprises, or consists of, the sequence of LAV1/PDK13 strain (SEQ ID No.3) wherein at least nucleotides at positions 5962 and 7947, and optionally 2719, are mutated, with the proviso that the following nucleotides are not mutated: 1323, 1541, 1543, 1545, 1567, 1608, 2363, 2695, 2782, 5063, 6048, 6806, 7330, and 9445. Preferably, the mutations are substitutions. Preferably, the nucleotide at position 5962 is A, the nucleotide at position 7947 is G. Still preferably, the isolated strain according to the invention contains sequence SEQ ID No.3 which comprises the mutations 2719 G>A, 5962 C>A, and 7947 A>G.

Hence, a live attenuated dengue-1 virus strain according to the invention comprises the sequence of wild-type dengue-1 strain 16007 (SEQ ID No.2) wherein said sequence comprises at least the mutations 1323 T>C, 1541 G>A, 1543 A>G, 1545 G>A, 1567 A>G, 1608 C>T, 2363 A>G, 2695 T>C, 2782 C>T, 5063 G>A, 5962 C>A, 6048 A>T, 6806 A>G, 7330 A>G, 7947 A>G, and 9445 C>T. Preferably, a live attenuated strain according to the invention further comprises the mutation 2719 G>A by reference to the nucleotide sequence of wild-type strain 16007 (SEQ ID No.2).

The live attenuated dengue-1 virus strains according to the invention encompass variant strains that comprise a sequence SEQ ID No.3 mutated in positions 5962 and 7947, as defined above, and that further comprise a substitution of one or more nucleotides in a given codon position that results in no alteration in the amino acid encoded at that position.

Advantageously, the live attenuated dengue-1 virus strain according to the invention comprises a sequence which differs by a limited number of mutations, e.g. no more than 5, still preferably no more than 2, from SEQ ID No.1.

Preferably, the genomic sequence of a dengue-1 virus strain according to the invention consists of the nucleotide sequence SEQ ID No.1.

The invention also relates to live attenuated dengue-1 strains that may be derived from the VDV1 strain of sequence SEQ ID No.1 by further passages on cells, in particular Vero cells.

The invention also relates to an isolated nucleic acid which comprises, or consists of, the DNA sequence SEQ ID No.1 or its equivalent RNA sequence.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix.

As used herein, by RNA sequence "equivalent" to SEQ ID No.1 is meant a sequence SEQ ID No.1 wherein deoxythymidines have been replaced by uridines. As SEQ ID No.1 constitutes VDV1 cDNA sequence, the equivalent RNA sequence thus corresponds to the positive strand RNA of VDV1.

The invention further relates to the polyprotein of sequence SEQ ID No.41 and to fragments thereof. SEQ ID No.41 is the sequence of the polyprotein encoded by SEQ ID No.1

A "fragment" of a reference protein is meant a polypeptide which sequence comprises a chain of consecutive amino acids of the reference protein. A fragment may be at least 8, at least 12, at least 20, amino acid long.

Said fragments of the polyprotein of sequence SEQ ID No.41 comprise at least a lysine at position 481 of NS3 protein (position 1956 of SEQ ID No.41), and/or an arginine at position 125 of NS5 protein (position 2618 of SEQ ID No.41).

According to an embodiment the fragment of the polyprotein encoded by SEQ ID No.1 is or comprises NS3 protein and/or NS5 protein.

Immunogenic and Vaccine Compositions

The invention also relates to an immunogenic composition, suitable to be used as a vaccine, which comprises a VDV1 strain according to the invention.

The immunogenic compositions according to the invention elicit a specific humoral immune response toward the dengue virus comprising neutralizing antibodies.

Preferably, the immunogenic composition is a vaccine.

According to an embodiment, the immunogenic is a monovalent composition, i.e. it elicits a specific immune response and/or confers protection against Dengue-1 virus only.

According to another embodiment, the invention relates to a multivalent dengue immunogenic composition. Such a multivalent immunogenic composition or vaccine may be obtained by combining individual monovalent dengue vaccines. The immunogenic or vaccine composition may further comprise at least a live attenuated dengue virus of another serotype. In particular, the immunogenic or vaccine composition may comprise a VDV1 according to the invention in combination with at least a live attenuated dengue virus selected from the group consisting of serotype 2, serotype 3, and serotype 4.

Preferably, the immunogenic or vaccine composition may be a tetravalent dengue vaccine composition, i.e. a vaccine composition that comprises a VDV1 according to the invention in combination with a live attenuated dengue-2 virus strain, a live attenuated dengue-3 virus strain and a live attenuated dengue-4 virus strain.

Live attenuated dengue-2, dengue-3 and dengue-4 virus strains have been described previously. Reference may be made to the live-attenuated vaccines that were developed by Mahidol University by passaging dengue serotype 2 (strain 16681, passage 53; LAV2), and serotype 4 (strain 1036, passage 48, LAV4) viruses in Primary Dog Kidney (PDK) Cells, and for serotype 3 (strain 16562) in Primary Green Monkey Kidney (PGMK) cells (passage 30) and Fetal Rhesus Lung (FRhL) cells (passage 3) (LAV3). The nucleotide sequences of LAV2 (SEQ ID No.42), LAV3 (SEQ ID No.43), and LAV4 (SEQ ID No.44) are shown in the annexed sequence listing.

Advantageously, a live attenuated dengue-2 strain may correspond to a VDV2 strain which has been obtained from the LAV2 strain developed by Mahidol by a process of sanitization on Vero cells. In particular a live attenuated dengue-2 strain (VDV2) may comprise, and advantageously consists of the sequence SEQ ID No.40.

Immunogenic compositions including vaccines may be prepared as injectables which can correspond to liquid solutions, suspensions or emulsions. The active immunogenic ingredients may be mixed with pharmaceutically acceptable excipients which are compatible therewith.

The immunogenic compositions or vaccines according to the present invention may be prepared using any conventional method known to those skilled in the art. Conventionally the antigens according to the invention are mixed with a pharmaceutically acceptable diluent or excipient, such as water or phosphate buffered saline solution, wetting agents, fillers, emulsifier stabilizer. The excipient or diluent will be selected as a function of the pharmaceutical form chosen, of the method and route of administration and also of pharmaceutical practice. Suitable excipients or diluents and also the requirements in terms of pharmaceutical formulation, are described in Remington's Pharmaceutical Sciences, which represents a reference book in this field.

Preferably, the immunogenic composition or vaccine corresponds to an injectable composition comprising an aqueous buffered solution to maintain e.g. a pH (as determined at RT with a pH meter) in the range of 6 to 9.

The composition according to the invention may further comprise an adjuvant, i.e. a substance which improves, or enhances, the immune response elicited by the VDV1 strain. Any pharmaceutically acceptable adjuvant or mixture of adjuvants conventionally used in the field of human vaccines may be used for this purpose.

The immunogenic compositions or vaccines according to the invention may be administered by any conventional route usually used in the field of human vaccines, such as the parenteral (e.g. intradermal, subcutaneous, intramuscular) route In the context of the present invention immunogenic compositions or vaccines are preferably injectable compositions administered subcutaneously in the deltoid region.

Method for Immunizing

The invention further provides for a method of immunizing a host in need thereof against a dengue infection which comprises administering the host with an immunoeffective amount of an immunogenic composition or a vaccine according to the invention.

A "host in need thereof" denotes a person at risk for dengue infection, i.e. individuals travelling to regions where dengue virus infection is present, and also inhabitants of those regions.

The route of administration is any conventional route used in the vaccine field. The choice of administration route depends on the formulation that is selected. Preferably, the immunogenic composition or vaccine corresponds to an injectable composition administered via subcutaneous route, advantageously in the deltoid region.

The amount of LAV or VDV in particular VDV1 in the immunogenic compositions or vaccines may be conveniently expressed in viral plaque forming unit (PFU) unit or Cell Culture Infectious Dose 50% ($CCID_{50}$) dosage form and prepared by using conventional pharmaceutical techniques.

For instance, the composition according to the invention may be prepared in dosage form containing 10 to $10^6$ CCID$_{50}$, or from $10^3$ to $10^5$ CCID$_{50}$ of LAV or VDV, for instance 4±0.5 log$_{10}$ CCID$_{50}$ of VDV1 strain for a monovalent composition. Where the composition is multivalent, to reduce the possibility of viral interference and thus to achieve a balanced immune response (i.e. an immune response against all the serotype contained in the composition), the amounts of each of the different dengue serotypes present in the administered vaccines may not be equal.

An "immunoeffective amount" is an amount which is capable of inducing a specific humoral immune response comprising neutralising antibodies in the serum of a vaccinee, as evaluated by the plaque reduction neutralization test as described in section 4.1.2.2; a serum being considered to be positive for the presence of neutralizing antibodies when the neutralizing antibody titer thus determined is at least superior or equal to 1:10.

The volume of administration may vary depending on the route of administration. Subcutaneous injections may range in volume from about 0.1 ml to 1.0 ml, preferably 0.5 ml.

The optimal time for administration of the composition is about one to three months before the initial exposure to the dengue virus. The vaccines of the invention can be administered as prophylactic agents in adults or children at risk of Dengue infection. The targeted population thus encompasses persons which are naïve as well as well as non-naïve with regards to dengue virus. The vaccines of the invention can be administered in a single dose or, optionally, administration can involve the use of a priming dose followed by a booster dose that is administered, e.g. 2-6 months later, as determined to be appropriate by those of skill in the art.

The invention will be further described in view of the following figures and examples.

FIGURES

Figure 3:
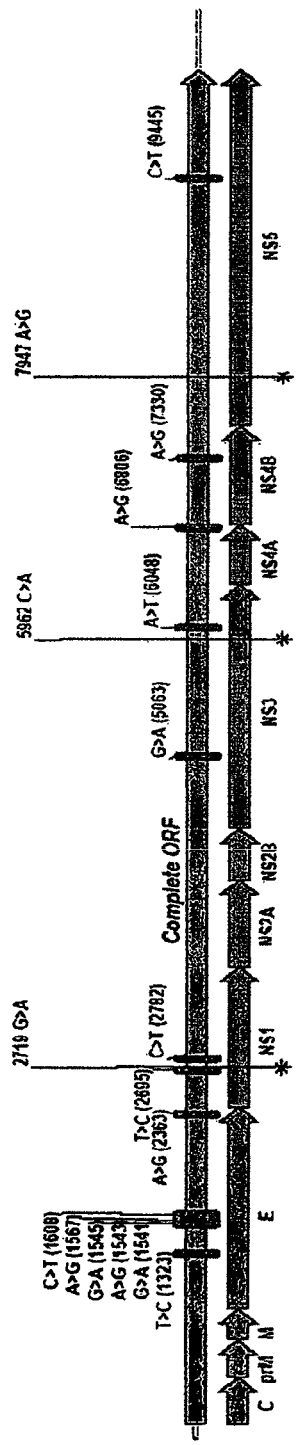

FIG. 3 is a diagrammatic representation of VDV1 genome map. The above arrow is the polyprotein coding sequence. The below arrows represent mature peptides coding sequence. The vertical bars symbolize the nucleotidic variations between wild-type dengue 1 strain 16007 and LAV1 strain. The stars designate the nucleotidic variations between LAV1 and VDV1.

Figure 4:
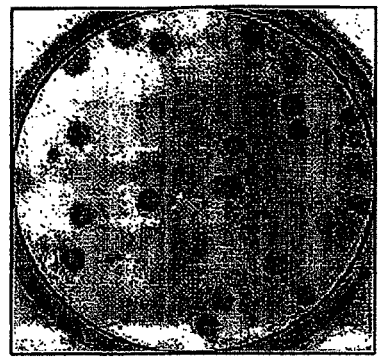
Figure 4:
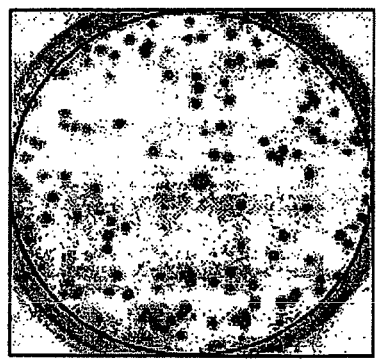
Figure 4:
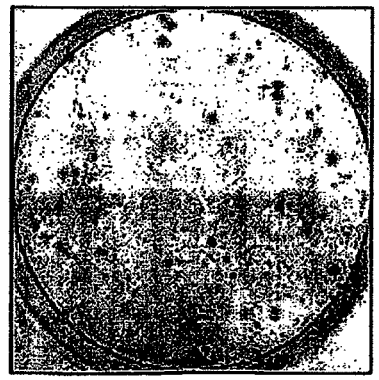

FIG. 4 shows plaque size analysis after 7 days of incubation at 37° C. for dengue-1 viruses LAV1, VDV1, and strain 16007.

Figure 5:
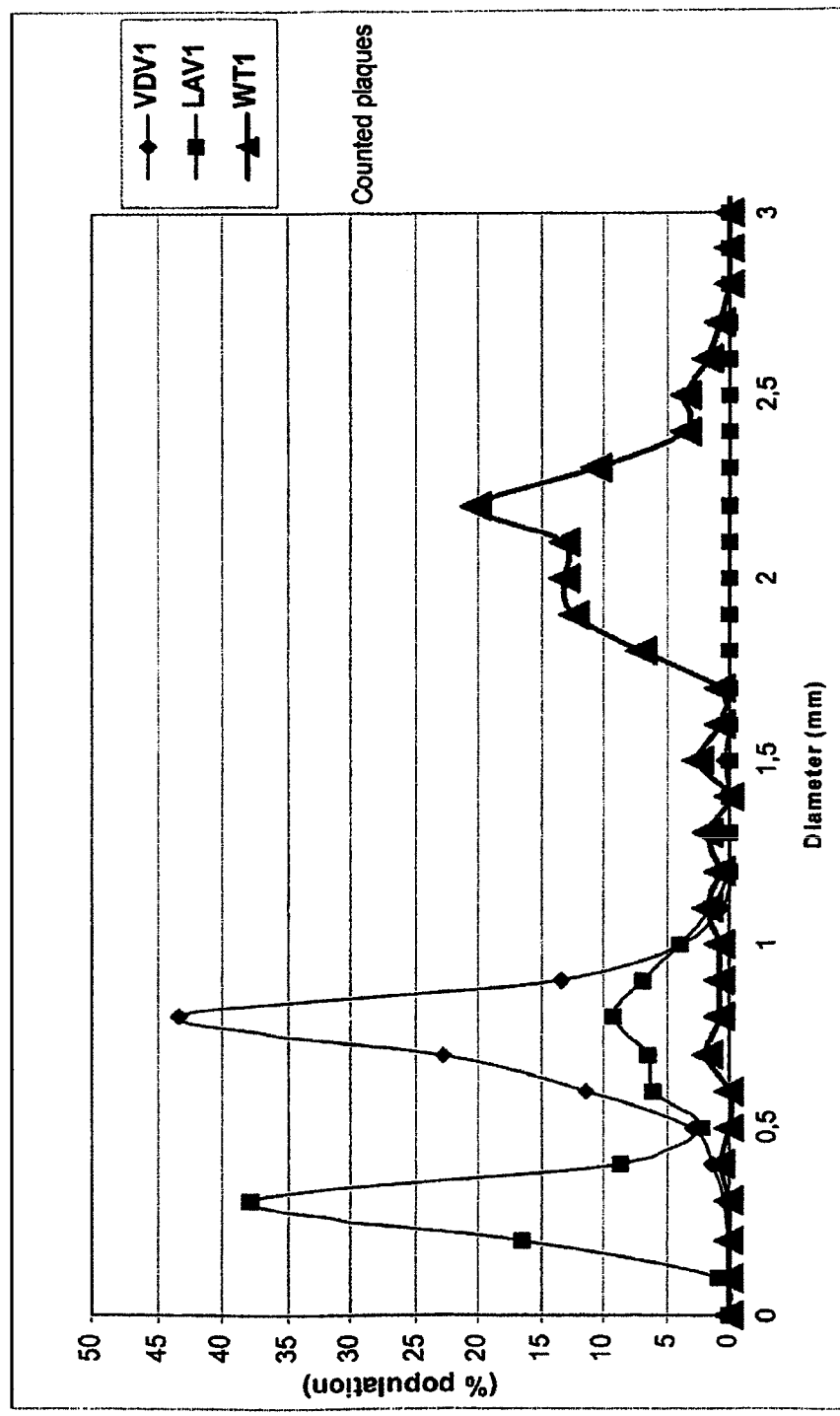

FIG. 5 is a graphic analysis showing plaque size distribution for dengue-1 viruses LAV1, VDV1, and strain 16007.

Figure 6:
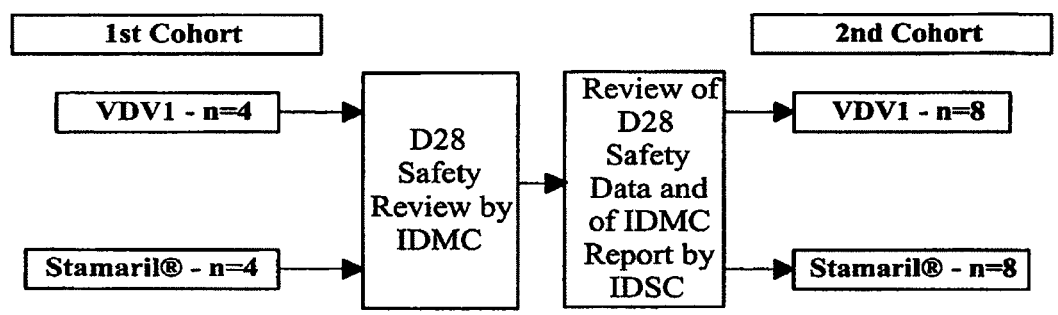

FIG. 6 is a summary of Trial Design for assessment of safety of VDV1 monovalent in healthy flavivirus-naïve adults.

EXAMPLES

Example 1

Sanitization 1.1 Viral RNA Purification

It was initially intended to perform sanitization of LAV1 by purifying and transfecting viral RNA directly extracted from an early seed of the vaccine strain, DEN-16007/PDK10 or DEN-16007/PDK11 (produced by Sanofi Pasteur. Titer: 4.60 log TCID$_{50}$/ml). Eight unsuccessful assays were carried out in that way, with RNA quantities varying from $10^3$ to $10^7$ copies. It was then decided to perform one adaptation passage on Vero cells, before RNA extraction and transfection.

Vero cells (VERO LS10 p142 to 145) were infected with a sample of the master seed DEN-1/PDK11, at m.o.i 0.01, and incubated at 32° C. for 5 days. Culture medium was then replaced by infection medium (containing 10 mM MgSO$_4$). Clear cytopathic effects were visible the following day, and presence of viral RNA in culture supernatant was confirmed by RT-PCR. Culture medium was collected at day 8 post-infection, diluted with an equivalent volume of an aqueous buffered solution comprising cryoprotective agents (pH=7.5) and kept frozen at –70° C. until use. This Vero-amplified virus was named DEN-1/V100. Its infectious titer was determined on Vero cells and was of 6.9 log TCID$_{50}$/ml.

The RNA purification and transfection process was performed as follows. DEN-1 V100 suspension was diluted in order to contain at least $3\times10^4$ and up to $3\times10^7$ TCID$_{50}$ or PFU of virus per milliliter. One unit of benzonase diluted in 0.01 ml of William's medium was added to 0.5 ml of virus, in order to digest DNA or RNA molecules from cellular origin, and the solution was incubated for 2 hours at 4° C. on an agitator. At the end of incubation step, 0.65 ml of a denaturing buffer containing guanidium chloride, detergent (SDS), and βmercaptoethanol (RTL-βmercaptoethanol buffer, provided in the kit RNeasy Mini kit, Qiagen Ref. 74104) were added and proteins were extracted once with phenol/chloroform (1/1) vol/vol and once with chloroform vol/vol, followed by centrifugation for 5 min at 14,000 rpm at room temperature. After each extraction, the aqueous phase was collected, taking care not to collect material (white precipitate) at the interface, and transferred to a clean 1 ml-Eppendorf tube. The RNA solution was then applied onto a QIAgen column following the recommendations of the manufacturer (RNeasy minikit, QIAgen), in order to remove traces of solvent, and eluted with 0.06 ml of nuclease-free H2O water. The presence of viral RNA was confirmed by quantitative RT-PCR, using a reference curve established with known quantities of virus, in TCID$_{50}$/ml.

1.2 Transfection of Vero Cells with Purified RNA

Transfection was performed using lipofectamine (LF2000 Reagent, Life Technologies), a mixture of cationic lipids that associate to RNA through charge interactions and allows transfer of the complexes into the cytoplasm of the cells by fusion with the cell membrane. The optimal quantity of LF2000 reagent was determined in a preliminary experiment by incubating Vero cells, plated 16 to 24 hours before (0.3-0.5×10$^6$ cells per well in a 6 wells plate) with increasing doses (5 to 20 µl) of lipofectamine. Cells were then incubating 4 to 5 hours at 32° C., 5% CO$_2$, before replacing the medium by fresh culture medium without FCS, and the incubation was continued overnight at 32° C. Toxicity (round, refringent or floating cells, homogeneity of the cell monolayer) was checked regularly for 48 hours, under an inverted microscope. The highest dose of lipofectamine that was not toxic under these conditions was 10 µl and was chosen for RNA transfection.

Four transfections were carried out in parallel, using 1/10 of the purified RNA preparation (corresponding to about 4×10$^5$ TCID$_{50}$). Twelve microliters of viral RNA solution were diluted in 500 µl of OptiMEM medium (GIBCO) containing 10 µl of LF2000 Reagent (a mixture of cationic lipids that associate to RNA through charge interactions, and allow transfer of the complexes into the cytoplasm of the cells by fusion with the cell membrane). 200 ng of yeast tRNA were added as carrier in 2 out of the 4 reactions.

The 4 transfection mixes were allowed to precipitate for 10 min at room temperature before addition to 6-wells plates of confluent Vero cells. After 4 hours of incubation at 32° C., transfection mix was removed and cells were rinsed once in PBS. Three milliliters of post-transfection medium (Williams, GIBCO) were added, and incubation was continued for 5 days at 32° C. Culture medium was then replaced by 3 ml of Dengue infection medium (Williams supplemented with 10 mM $MgSO_4$).

Moderate toxic effects were observed 24 hours post-transfection and disappeared on day 3. Typical cytopathic effects (round, refringent cells) were detected 6 to 8 days post-transfection in all transfection assays. Release of virus in the supernatant of these cells was confirmed by qRT-PCR. Culture fluids (3 ml) were collected at day 6 and at day 8 post-transfection, and pooled. The viruses were diluted with 6 ml of an aqueous buffered solution comprising cryoprotective agents (pH=7.5) and frozen until further amplification.

The four viral solutions such obtained after transfection were named TV (for Transfection in Vero cells) 100, TV200, TV300 and TV400, and exhibited similar infectious titers (see below):

TV100: 6.95 log $TCID_{50}$
TV200: 6.80 log $TCID_{50}$
TV300: 6.80 log $TCID_{50}$
TV400: 6.85 log $TCID_{50}$ Of note, transfection efficiency was not significantly increased in samples transfected in presence of tRNA (TV300 and TV400).

1.3 Characterization of Viruses Recovered after Transfection

Plaques sizes of DEN1-V100 and TV100 to 400 were determined. Briefly, Vero cells were plated at a density of 1,000,000 cells/$cm^2$ in culture medium containing 4 of FBS. After overnight incubation, the medium was removed and cells were infected with serial twofold or fivefold dilutions of virus. After 1.5 hour at 37° C. 5% $CO_2$, the inoculum was removed and cells were incubated at 37° C. 5% $CO_2$ in Minimal Eagle Medium (MEM) containing 1.26% methylcellulose and 10% FBS. After 11 days of incubation, plates were fixed 20 minutes in cold acetone at −20° C. and revealed by immuno-coloration with a flavivirus-specific mAb, diluted at 2.5 μg/ml. Viral plaques were measured using an image analysis software (Saisam/Microvision)

As a control, DEN-1 16007 and LAV1 were plated in parallel. The data are presented in Table 1.

TABLE 1

Plaques size of DEN-1 16007, LAV1, V100 (before transfection) and TVX00 (after transfection)

| Step | Virus | Phenotype: Large Plaque | Phenotype: Small Plaque |
|---|---|---|---|
| | DEN1 16007 (wt) | 42 | 0 |
| Master Seed/PDK11 | MS-16007/PDK11 | 0 | 91 |
| Working Seed/PDK12 | WS LST-22 | 0 | 84 |
| Bulk Seed/PDK13 | D1-0010R1 | 0 | 188 |
| VERO amplification | V100 | 0 | 90 |
| Transfected viruses | TV100 | 0 | 115 |
| | TV200 | 1 | 90 |
| | TV300 | 0 | 92 |
| | TV400 | 0 | 107 |

The V100 virus, amplified on Vero cells, exhibits a homogeneous small plaque (SP) phenotype. Plaques are slightly larger than observed in the different samples of LAV1 (2-3 mm diameter instead of <2 mm). This SP phenotype is retained in the viruses recovered after transfection. One large plaque (LP), among 90 virus plated, was detected in TV200 sample. However, this proportion shifted to 10 LP for 82 SP plated after just one amplification passage on VERO cells suggesting that the LP population was dominant.

Of note, sequencing of attenuation-critical positions performed in parallel did not reveal any mutation in transfected viruses, compared to LAV1.

1.4 Plaque-Purifications

A sample of DEN-1/TV100 virus, presenting a homogenous SP phenotype was chosen for plaque-purification. Briefly, Vero cells were plated in 6-well plates and infected with serial dilutions of virus, in order to get between 1 and 20 plaques by plate. After 1.5 hour at 37° C. 5% $CO_2$, the inoculum was removed and cells were incubated under 3 ml of solid medium composed of MEM-10% FCS pre-heated at 42° C. and mixed extemporaneally with 2% of melted agarose equilibrated at 42° C. The medium was allowed to solidify at room temperature for 30 min; under flow hood, and plates were incubated in inverted position for 10 days at 32° C.-5% $CO_2$. A second layer of the same medium supplemented with 0.01% of neutral red was then added and plates were incubated for an additional night at 32° C. Four well-isolated small plaques were picked under sterile conditions using a micro-pipet equipped with a 0.1 ml tip, and transferred into sterile tubes containing 0.2 ml of MEM-4% FCS. The suspension was homogenized by vortexing, serially diluted in the same medium, and immediately used to infect 6-well plates of Vero cells. The protocol was repeated and a second picking of six SP was done. Each picked plaque was diluted in 1 ml of medium, before amplification on Vero cells, in T25 $cm^2$ flasks. Culture medium was collected at day 6 post-infection, diluted with the same volume of an aqueous buffered solution comprising cryoprotective agent (pH 7.5) and frozen at −70° C. All these steps were performed at 32° C.

Plaque-purified viruses were named DEN-1/TV111, DEN-1/TV112, DEN-1/TV121, DEN-1/TV131, DNE-1/TV132 and DEN-1/TV141, respectively. Infectious titers were determined on Vero cells (see below):

TV111=6,85 Log $CCID_{50}$/ml TV112=6,80 Log $CCID_{50}$/ml

TV121=6,80 Log $CCID_{50}$/ml TV131=6,70 Log $CCID_{50}$/ml

TV132=6,45 Log $CCID_{50}$/ml TV141=5,70 Log $CCID_{50}$/ml

A second amplification on Vero cells was carried out for three clones: TV111, TV112 and TV121.

1.5 Characterization of Cloned Virus

Plaques size of DEN-1/TV111, DEN-1/TV112, DEN-1/TV121, DEN-1/TV131, DEN-1 TV132 and DEN-1/TV141 candidates were determined. Spot-sequencing of specific attenuation loci was also performed and revealed no mutation (Table 2).

TABLE 2

Sequencing at attenuation-specific spots of DEN-1 viruses

| Step/cell | Virus | E | | | | | | NS1 | | NS3 | | NS4A | NS4B | NS5 |
| --- | --- | --- | --- | --- | --- | --- | --- | --- | --- | --- | --- | --- | --- | --- |
| | | 1323 | 1541 | 1543 | 1545 | 1567 | 1608 | 2363 | 2695 | 2782 | 5063 | 6048 | 6806 | 7330 9445 |
| Non attenuated/PGMK | DEN-1 16007 | T | G | A | G | A | C | A | T | C | G | A | A | A C |
| Vaccine/PDK | DEN-1 16007/ PDK-13 | C | A | G | A | G | T | G | C | T | A | T | G | G T |
| | TV111 | C | A | G | A | G | T | G | C | T | A | T | G | G T |
| | TV112 | C | A | G | A | G | T | G | C | T | A | T | G | G T |
| 2nd plaque- | TV121 | C | A | G | A | G | T | G | C | T | A | T | G | G T |
| purification/VERO | TV131 | C | A | G | A | G | T | G | C | T | A | T | G | G T |
| | TV132 | C | A | G | A | G | T | G | C | T | A | T | G | G T |
| | TV141 | C | A | G | A | G | T | G | C | T | A | T | G | G T |
| Pre-master seed/VERO | VDV1 (VERO-6) | C | A | G | A | G | T | G | C | T | A | T | G | G T |

Nucleotides position are indicated below each gene and referred of DEN-1 16007 strain SEQ ID No 2.

In absence of any other criterion able to differentiate between these clones, TV121 was arbitrarily chosen as pre-master for VDV1.

In conclusion, a total number of 6 passages on VERO cells were carried out to adapt and clone the initial DEN-1 16007/PDK11 attenuated strain. Viral RNA was purified and transfected into qualified VERO cells, in conditions fitting with an industrial application (environmental control, traceability of raw material and experiments, certificate of analysis for animal-derived products). The VERO-adapted strain was cloned by plaque-purification to generate pre-master seed of VDV1 vaccine candidate, at VERO passage number 6.

Contrary to LAV1, VDV1 presents a homogenous small plaque size phenotype. Furthermore, no mutation was identified at attenuation-specific positions. Further characterizations have been performed then by determining bulk VDV1 complete sequence and phenotypic testing.

Example 2

Sequencing

The complete sequence of the virus was generated according to the following strategy. Starting from a VDV1-containing sample, the genomic RNA was extracted and purified, retro-transcribed into cDNA. Then all overlapping PCR amplifications were performed from the cDNA, with addition of the sequencing tags at both ends of each PCR product. All individual sequences were generated in automated devices and analysed. Next step consisted of the genome reconstruction by multiple alignments of all individual sequences. At this point, each unexpected nucleotide change, with regard to the reference sequence, was carefully re-analysed by going back to raw data. Such change was systematically confirmed by another sequence performed from a new PCR product. Once all ambiguities were solved, the sequenced virus genome was completed, and the new molecule was created in Vector NTi database. It can be used for inter genomes analysis, by multiple sequence alignment.

2.1 Materials
2.1.1 Viruses

The viruses to which it is referred here are DEN-1 16007; LAV-1/PDK13; VDV1, the sequences of which are given in the attached sequence listing. The complete genome sequence of these viruses is 10735 nucleotides in length.

2.1.2 Primers

All primers have been designed in Seqweb bioinformatics package (Accelrys), primer design module (Table 3).

TABLE 3 list of RT-PCT and sequencing primers

| Name | Primers sequences | NtStart | NtEnd | Primer length | RT-PCR length | Overlap |
| --- | --- | --- | --- | --- | --- | --- |
| D1 01+ | GTTTTCCCAGTCACGACtacgtggaccgacaagaacag (SEQ ID No. 4) | 12 | 32 | 38 | 897 | −32 |
| D1 01− | AACAGCTATGACCATGggatggagttaccagcatcag (SEQ ID No. 5) | 928 | 908 | 37 | | |
| D1 02+ | GTTTTCCCAGTCACGACtgaacaccgacgagacaaac (SEQ ID No. 6) | 688 | 707 | 37 | | 201 |
| D1 02− | AACAGCTATGACCATGaggtccaaggcagtggtaag (SEQ ID No. 7) | 1598 | 1579 | 36 | 892 | |

TABLE 3-continued list of RT-PCT and sequencing primers

| Name | Primers sequences | NtStart | NtEnd | Primer length | RT-PCR length | Overlap |
|---|---|---|---|---|---|---|
| D1 03+ | GTTTTCCCAGTCACGACttggaaatgagaccacagaac (SEQ ID No. 8) | 1386 | 1406 | 38 | | 173 |
| D1 03- | AACAGCTATGACCATGgaaacaccgctgaacaaaac (SEQ ID No. 9) | 2289 | 2270 | 36 | 885 | |
| D1 04+ | GTTTTCCCAGTCACGACggttcaagaagggaagcag (SEQ ID No. 10) | 2106 | 2124 | 36 | | 146 |
| D1 04- | AACAGCTATGACCATGttctatccagtacccatgtc (SEQ ID No. 11) | 3028 | 3008 | 37 | 903 | |
| D1 05+ | GTTTTCCCAGTCACGACcagaataccaccttcatcatcg (SEQ ID No. 12) | 2804 | 2825 | 39 | | 183 |
| D1 05- | AACAGCTATGACCATGttcccatccccatcttgtc (SEQ ID No. 13) | 3689 | 3671 | 35 | 868 | |
| D1 06+ | GTTTTCCCAGTCACGACggaaatcagaccagtcaaggag (SEQ ID No. 14) | 3418 | 3439 | 39 | | 232 |
| D1 06- | AACAGCTATGACCATGtgttgtgtgaggcaccagag (SEQ ID No. 15) | 4349 | 4330 | 36 | 913 | |
| D1 07+ | GTTTTCCCAGTCACGACgcaaaccactaaccatgtttc (SEQ ID No. 16) | 4077 | 4097 | 38 | | 233 |
| D1 07- | AACAGCTATGACCATGccacttgttgtcaccactc (SEQ ID No. 17) | 4995 | 4977 | 35 | 901 | |
| D1 08+ | GTTTTCCCAGTCACGACccaagggaagagactggaac (SEQ ID No. 18) | 4699 | 4718 | 37 | | 259 |
| D1 08- | AACAGCTATGACCATGtcctgatttgatgcttggaac (SEQ ID No. 19) | 5626 | 5606 | 37 | 908 | |
| D1 09+ | GTTTTCCCAGTCACGACaagcacattttaccgatccag (SEQ ID No. 20) | 5376 | 5396 | 38 | | 210 |
| D1 09- | AACAGCTATGACCATGgtcgtagtttctttcttttctccttc (SEQ ID No. 21) | 6299 | 6275 | 41 | 900 | |
| D1 10+ | GTTTTCCCAGTCACGACgcaatagacggggaatacag (SEQ ID No. 22) | 6074 | 6093 | 37 | | 182 |
| D1 10- | AACAGCTATGACCATGatgatggtggttttcagcag (SEQ ID No. 23) | 6901 | 6882 | 36 | 809 | |
| D1 11+ | GTTTTCCCAGTCACGACgtgttgcttattccagagcc (SEQ ID No. 24) | 6725 | 6744 | 37 | | 138 |
| D1 11- | AACAGCTATGACCATGgctgtcttttccatttttctcc (SEQ ID No. 25) | 7622 | 7601 | 38 | 877 | |
| D1 12+ | GTTTTCCCAGTCACGACactttgcacatcacagatcc (SEQ ID No. 26) | 7354 | 7373 | 37 | | 228 |
| D1 12- | AACAGCTATGACCATGttcgcactagcattcctcc (SEQ ID No. 27) | 8192 | 8174 | 35 | 821 | |
| D1 13+ | GTTTTCCCAGTCACGACcacctgagaaatgtgacacc (SEQ ID No. 28) | 7980 | 7999 | 37 | | 175 |
| D1 13- | AACAGCTATGACCATGtttccttgtttatgaagctccc (SEQ ID No. 29) | 8907 | 8886 | 38 | 907 | |
| D1 14+ | GTTTTCCCAGTCACGACcaaaagcgaaacgaggcac (SEQ ID No. 30) | 8661 | 8679 | 36 | | 207 |
| D1 14- | AACAGCTATGACCATGgttttcaccacacagtcatctcc (SEQ ID No. 31) | 9575 | 9554 | 38 | 894 | |
| D1 15+ | GTTTTCCCAGTCACGACagaccagcgaaaaatggaac (SEQ ID No. 32) | 9314 | 9333 | 37 | | 221 |

TABLE 3-continued list of RT-PCT and sequencing primers

| Name | Primers sequences | NtStart | NtEnd | Primer length | RT-PCR length | Overlap |
|---|---|---|---|---|---|---|
| D1 15- | AACAGCTATGACCATGtcccaatgagccttctcac (SEQ ID No. 33) | 10196 | 10178 | 35 | 865 | |
| D1 16+ | GTTTTCCCAGTCACGACgctaatgctatctgttcagcc (SEQ ID No. 34) | 9896 | 9916 | 38 | | 262 |
| D1 16- | AACAGCTATGACCATGtgattcaacagcaccattcc (SEQ ID No. 35) | 10726 | 10707 | 36 | | |
| D1 16i+ | ccatggaagctgtacgc (SEQ ID No. 36) | 10480 | 10496 | 17 | | |
| D1 16i- | gagacagcaggatctctgg (SEQ ID No. 37) | 10671 | 10652 | 19 | 812 | −28 |

2.2 Methods 2.2.1 Viral RNA Purification

From previous experience, a minimal of 1000 $DICC_{50}$ is required to get a positive RT-PCR reaction in the next steps. This means that a minimum virus titer of $10^4$ $DICC_{50}$/mL is necessary. Virus genomic RNA was purified using QIAamp viral RNA mini kit (Qiagen), according to the manufacturer's recommendations. Briefly, a volume of 140 μl from a crude viral sample was incubated in the presence of the lysis solution, and loaded onto a kit column. After washing steps, the purified viral RNA was eluted by 60 μl of sterile nuclease-free water containing 1 μl (40 units) of RNAse inhibitor (RNAse Out, Sigma).

2.2.2 Reverse Transcription

Viral RNA was reverse transcribed into cDNA by a reverse transcriptase (reverse iT) from ABGene. Again, standard operating conditions were applied, using 10 μl of purified RNA, in a final reaction volume of 20 μl. The reaction was initiated by hybridization of the minus strand primers. One RT reaction per PCR was performed (Table 1). The cDNA synthesis was obtained by 45 min incubation at 47° C.

2.2.3 PCR

All PCR were performed with Expand High Fidelity PCR system (Roche diagnostics), using all 16 pairs of primers (+) and (−) from Table 1. PCR conditions were the following ones:

| RT | 2 μl |
|---|---|
| 10x buffer | 2.5 μl |
| dNTP mix (10 mM) | 2 μl |
| Primers | 0.8 μl each |
| H2O | 16.4 μl |
| Enzyme | 0.5 μl |

| PCR program | | | |
|---|---|---|---|
| Denaturation | 94° C. | 2 min | |
| Denaturation | 94° C. | 15 sec | |
| Hybridization | 55° C. | 30 sec | 40 cycles |
| Elongation | 68° C. | 1 min | |
| Elongation | 68° C. | 5 min | |

All PCR products were controlled by electrophoresis on agarose gel.

2.2.4 Sequencing

The major part of the sequence reactions has been outsourced to Genome Express. Genome extremities, ambiguities, some inter-PCR junctions, and regions not sequenced by Genome Express for technical reasons were performed in-house.

Sequencing at Genome Express: PCR products were shipped at +4° C., and sequencing results were received as informatic sequence files. Text file, quality files and chromatograms are available for each individual sequence. After sequence alignment, all discrepancies were checked on the chromatogram, and corrected if identified as sequence algorithm errors.

In-house sequencing: Sequence reactions were performed on thermocycler PTC-200 (MJ Research), with Sequitherm Excell II LC kit (Epicentre). Each PCR product was sequenced on both strands independently in a single reaction. Reactions were loaded onto a sequence electrophoresis gel. Run and analysis of sequence were performed on the automated sequencer Gene ReadiR 4200 (Li-Cor).

Sequence Reaction

| DNA | up to 200/250 ng |
|---|---|
| Reaction buffer | 7.2 μl |
| Primers (1-2 pM) | 1.5 μl each |
| Enzyme | 1 μl |
| H2O | up to 20 μl |

| PCR program | | | |
|---|---|---|---|
| Denaturation | 92° C. | 2 min | |
| Denaturation | 92° C. | 15 sec | |
| Hybridization | 50° C. | 30 sec | 30 cycles |
| Elongation | 70° C. | 1 min | |
| Elongation | 70° C. | 10 sec | |

Addition of 3 μl of denaturating/loading buffer.

Denaturation of samples 3 min at 95° C. and ice cooling just before samples loading.

Sequence Electrophoresis

| Electrophoresis parameters | | Gel parameters | |
|---|---|---|---|
| Voltage | 1500 V | Gel hight | 41 cm |
| Current | 35 mA | Gel thickness | 0.2 mm |
| Power | 40 W | Temperature | 45° C. |
| Run time | 9H00 | Scan speed | 3 |

2.3 Results

All PCR fragments were sequenced from both ends using a common PCR added tail, i.e. a specific motif which has been added at 5' end of all primers:

```
                                (SEQ ID No. 38)
5' primers:   M13SEQ-GTTTTCCCAGTCACGAC (SEQ ID No. 39)
3' primers:   M13REV-AACAGCTATGACCATG
```

M13-SEQ and -REV sequences correspond to universal M13 primers motifs (New England Biolabs references).

For final contig assembly, a quick analysis was performed in Vector NTi, in ContigExpress module (Informax). The LAV1 reference sequence was compared with all individual sequencing results. In such conditions, all results could be aligned at the right place on the complete genome, even when some regions were still missing contig assembly, giving a quick visualization of the overall genome alignment.

2.3.1 Complete VDV1 Sequence Assembly

The final sequence alignment was performed in Vector NTi, AlignX module (Informax). The classical multiple sequence alignment algorithm ClustalW (Thompson et al., 1994) was used by the software to build the global alignment. All the sequence results were aligned together with the LAV1 reference sequence, thus allowing for a better reconstruction of the genome. Any discrepancy in the sequence with regard to the reference required a confirmation on another independent sequence reaction. The complete sequence of VDV1 is shown in SEQ ID No.1.

Some ambiguities are often found in single sequences, especially near sequence extremities. This is inherent to the somewhat poor quality of the reaction at both ends of any PCR fragment. Such poor quality sequences were excluded from the alignment, until two other independent sequence reactions were available from other PCR products. Discrepancy towards the reference was not taken into account in the final alignment when not confirmed in at least two independent other PCR sequences matching the consensus. Conversely, any discrepancy confirmed on two independent sequences was kept in the final sequence.

Table 4 summarizes the characteristics of each individual sequence reaction, indicating start, end and length. Overlaps between adjacent PCR are also indicated, as well as differences with regard to the reference sequence in the last column.

TABLE 4

Dengue VDV1 individual sequences characteristics

| Name | Start | End | Size | Overlap | Comments |
|---|---|---|---|---|---|
| D1 01+ | 35 | 921 | 886 | 0 | |
| D1 01− | 899 | 33 | 866 | 209 | |
| D1 02+ | 712 | 1596 | 884 | | |
| D1 02− | 1569 | 713 | 856 | 196 | |
| D1 03+ | 1415 | 2277 | 862 | | |
| D1 03− | 2253 | 1400 | 853 | 160 | |
| D1 04+ | 2133 | 3027 | 894 | | 2719 G > A (NS1-100 s) |
| D1 04− | 3000 | 2117 | 883 | 212 | 2719 G > A (NS1-100 s) |
| D1 05+ | 2834 | 3681 | 847 | | |
| D1 05− | 3654 | 2815 | 839 | 247 | |
| D1 06+ | 3451 | 4332 | 881 | | |
| D1 06− | 4325 | 3434 | 891 | 243 | |
| D1 07+ | 4113 | 4987 | 874 | | |
| D1 07− | 4961 | 4089 | 872 | 245 | |
| D1 08+ | 4742 | 5564 | 822 | | |
| D1 08− | 5583 | 4742 | 841 | 183 | |
| D1 09+ | 5400 | 5916 | 516 | | |
| D1 09− | 6274 | 5758 | 516 | 197 | 5962 C > A (NS3-481 N > K); 2 sequences |
| D1 10+ | 6114 | 6868 | 754 | | |
| D1 10− | 6883 | 6077 | 786 | 135 | |
| D1 11+ | 6761 | 7504 | 743 | | |
| D1 11− | 7597 | 6733 | 864 | 217 | |
| D1 12+ | 7381 | 8034 | 653 | | 7947 A > G (NS5-125 K > R) |

TABLE 4-continued

Dengue VDV1 individual sequences characteristics

| Name | Start | End | Size | Overlap | Comments |
|---|---|---|---|---|---|
| D1 12- | 8143 | 7380 | 763 | 141 | 7947 A > G (NS5-125 K > R) |
| D1 13+ | 8003 | 9730 | 727 | | |
| D1 13- | 8857 | 8002 | 855 | 182 | |
| D1 14+ | 8687 | 9472 | 785 | | |
| D1 14- | 9544 | 8675 | 869 | 200 | |
| D1 15+ | 9344 | 10170 | 826 | | |
| D1 15- | 10162 | 9399 | 763 | 253 | |
| D1 16+ | 9917 | 10261 | 344 | | 2 sequences |
| D1 16- | 10706 | 10394 | 312 | | |
| D1 16i+ | 10500 | 10706 | 206 | 0 | |
| D1 16i- | 10649 | 10204 | 455 | | |

The two extremities of the genome could not be sequenced from PCR amplification, because cDNA synthesis and PCR DNA reaction required oligonucleotides complementary to the ends of the genome. During the amplification step, these oligonucleotides are incorporated into the PCR fragment. The sequence result is that of the synthetic oligonucleotide, and not that of the virus itself. PCR from both ends of the virus genome did work properly, suggesting that the viral sequence was not significantly different from the oligonucleotide sequence (if it had been the case, PCR amplification should have failed or at least should have been of poor quality). The two extremities of the genome could not be distinguished from all other PCR amplifications. So, in the reconstructed genome (SEQ ID No.1), both genome ends were considered as identical to oligonucleotide sequences (and also identical to the reference). At 5' end, the sequence is that of nucleotides 1 to 34. At 3' end, the sequence is that of nucleotides 10707 to 10735.

2.3.2 Sequence Comparison

Direct sequence comparison between VDV1 strain and LAV1 reference shows a series of 3 nucleotides differences. Table 5 gives the complete list of these positions.

TABLE 5

Sequence comparison between LAV1 and VDV1 strains

| Nucleotides | | | Amino Acids | | | | |
|---|---|---|---|---|---|---|---|
| Nt Position | LAV1 | VDV1 | Region | AA Position | LAV1 | VDV1 | Notes |
| 2719 | G | A | NS1 | 100 | G | G | Silent |
| 5962 | C | A | NS3 | 481 | N | K | |
| 7947 | A | G | NS5 | 125 | K | R | |

Nucleotide change in position 2719 is silent at the amino acid level. The second difference in position 5962 triggers an amino acid change at NS3-481 (asparagine to lysine). Both are hydrophilic, but lysine is positively charged, whereas asparagine is not. The last difference is located in NS5 peptide, substituting lysine to arginine in position NS5-125. Such amino acid substitution is relatively conservative from a chemical point of view, both arginine and lysine residues being hydrophilic and positively charged.

TABLE 6

Search of discrepancies on other Dengue 1 strains

| Nucleotide position on VDV1 strain | Number of strains sharing the same nucleotide |
|---|---|
| 2719 | 24/40 |
| 5962 | 6/40 |
| 7947 | 1/40 |

When performing sequence alignment between all available Genbank serotype 1 Dengue genomic sequences, it appears that most of the identified differences are also present on other strains (see Table 6). One position is unique in the VDV1 strain (position 7947; NS5-125).

Thus, the full genomic sequence of a VDV1 strain of the dengue virus has been established.

Three nucleotide differences have been detected with regard to the parent LAV1 genomic sequence. VDV1 vaccine strain is derived from LAV1, through virus "sanitization" and passage from dog to monkey cells.

Differences between LAV1 and VDV1 can have several origins. First, cloning steps can elect a viral subpopulation that is not 100% identical to the major sequence previously detected in LAV1. Second, LAV1 has been produced on PDK cells, whereas VDV1 has been made on Vero cells. Such passage from dog to monkey cells potentially induces virus changes that reflect adaptation to the new cell line. Third, as for all RNA viruses, the lower viral RNA polymerase fidelity triggers a higher genomic mutation rate than DNA polymerases do.

In term of sequences only 3 differences between LAV1 and VDV1 were observed, corresponding to only 2 amino acids substitutions. All 14 nucleotide positions that have been linked to LAV1 viral attenuation are conserved in VDV1. Furthermore the sequences of master and bulk VDV1 have been compared (Table 7).

TABLE 7

Dengue 1 nucleotide differences between wild type 16007 strain and attenuated LAV1/PDK13 and VDV1 strains

| Virus | 1323 / E-130 | 1541-3 / E-203 | 1545 / E-204 | 1567 / E-211 | 1608 / E-225 | 2363 / NS1-47 | 2695 / NS1-92 | 2719 / NS1-100 | 2782 / NS1-121 | 5063 / NS3-182 | 5962 / NS3-481 | 6048 / NS3-510 | 6806 / NS4a-144 | 7330 / NS4b-168 | 7947 / NS5-125 | 9445 / NS5-624 |
|---|---|---|---|---|---|---|---|---|---|---|---|---|---|---|---|---|
| DEN-1 16007 | T / Val | GaA / Glu | G / Arg | A / Gln | C / Ser | A / Met | T / Asp | G / Gly | C / Ala | G / Glu | C / Asn | A / Tyr | A / Met | A / Gln | A / Lys | C / Ser |
| LAV1/ PDK13 | C / Ala | AaG / Lys | A / Lys | G / Gln | T / Leu | G / Val | C / Asp | G / Gly | T / Ala | A / Lys | C / Asn | T / Tyr | G / Val | G / Gln | A / Lys | T / Ser |
| VDV1 Master | C / Ala | AaG / Lys | A / Lys | G / Gln | T / Leu | G / Val | C / Asp | A / Gly | T / Ala | A / Lys | A / Lys | T / Tyr | G / Val | G / Gln | G / Arg | T / Ser |
| VDV1 Bulk | C / Ala | AaG / Lys | A / Lys | G / Gln | T / Leu | G / Val | C / Asp | A / Gly | T / Ala | A / Lys | A / Lys | T / Tyr | G / Val | G / Gln | G / Arg | T / Ser |

Complete VDV1 master seed sequence was aligned with the bulk sequence. No difference between the two sequences was observed, indicating genetic stability across passages.

VDV1 shows a remarkable genetic stability with regard to its LAV1 parent.

Example 3

Characterization

The objective of these studies was to assess whether changes in attenuation markers occurred through passages.

Figure 1:
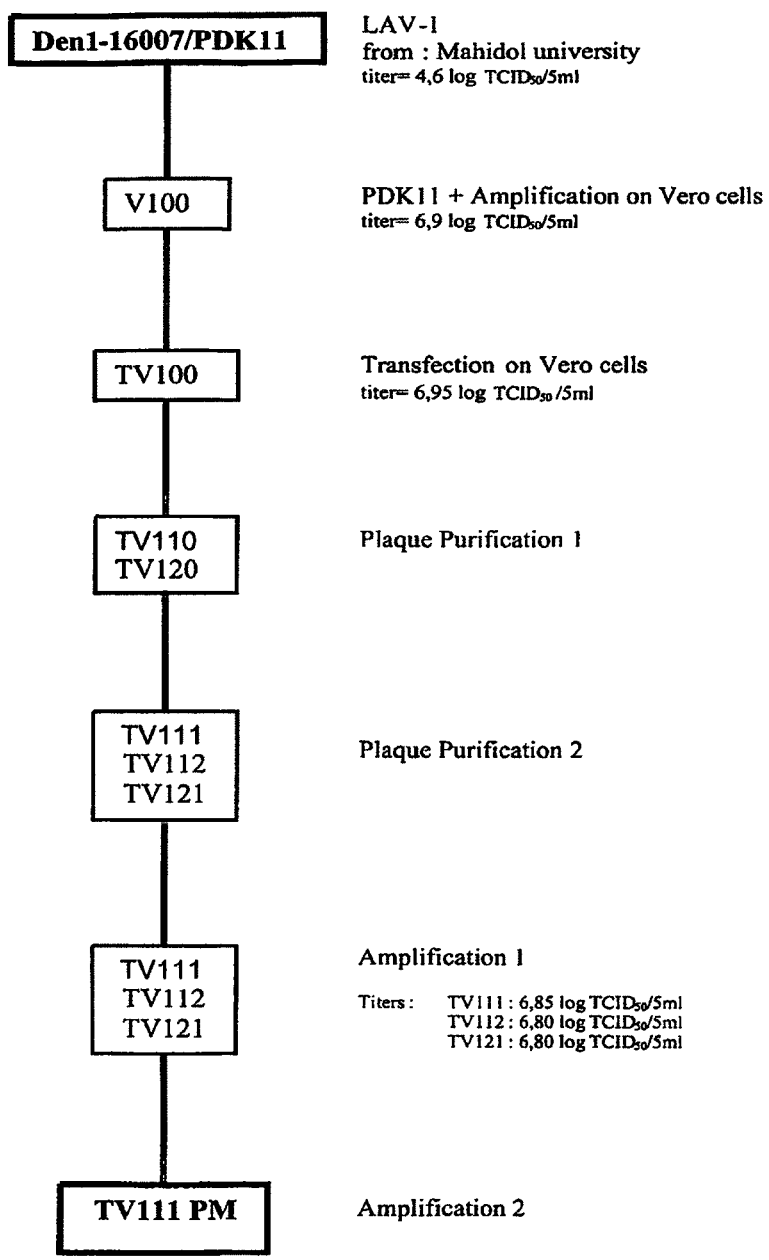
FIG. 1 is a summary of History of VDV1 pre-master seed.
Figure 2:
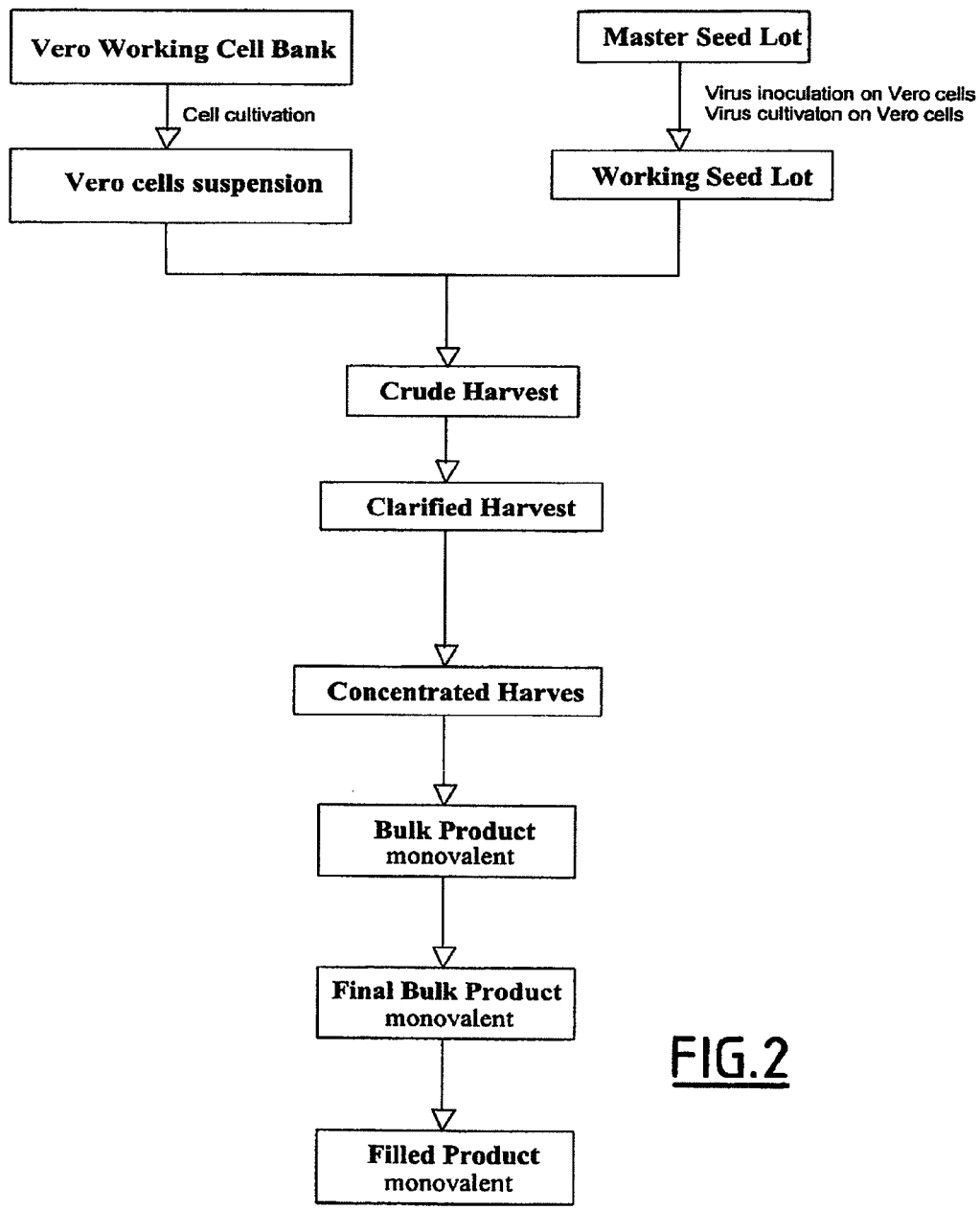
FIG. 2 is a flow chart that summarises the developed manufacturing process that gives rise to the Filled Product (monovalent), "ready to use" doses.

The flow chart shown on FIG. 2 summarises the developed manufacturing process that gives rise to the Filled Product (monovalent), "ready to use" doses Briefly, after 2 successive passages on Vero cells of the Viral Pre-Master Seeds delivered by the Research department, the respective working seeds were obtained. The final virus cultivations were also conducted by infection of a Vero cell suspension. The viruses produced are then harvested. DesoxyRiboNucleic Acid (DNA) was digested according to an enzymatic treatment. Impurities were removed by ultrafiltration. Infectious titers were enhanced by a concentration step. An aqueous buffered solution comprising cryoprotective agents (pH=7.5) is added and this 0.22-µm filtrated mixture is then diluted at the targeted dose within the same solution. The active substance is then filled into glass vials, freeze-dried, and stored before use.

3.1 Phenotypic Markers

The results are shown in Table 8. The validated tests performed for the master seed and the bulk are:

Plaque size: the assay was performed in Vero cells at 37° C. after 7 days of incubation. Sizing of the plaques was performed by Saisam v.5.2.0 (Microvision Instruments) dedicated software, after image capture with a video camera. Two populations (0.3 mm and 0.8 mm) were detected in LAV1. The major population was the smallest. After adaptation to Vero cells and biological cloning, VDV1 plaque size distribution appears homogenous, with more than 98% of the population showing a single peak, centered to 0.8 mm in diameter. These plaques are clearly distinct from plaques obtained with DEN-1 16007 virus (see FIGS. 4 and 5).

Temperature sensitivity: monovalent 1 exhibits clear restricted growth at 39° C. with respect to the non-temperature sensitive (Ts), wild-type (WT) D1-16007. This was demonstrated both by infectious titer assay and by viral RNA quantification. Master, bulk and passage 18 (10 passages after the bulk passage) of the monovalent 1 seed display 90% or more of titer reduction at 39° C., compared to 37° C.

TABLE 8

Summary of DEN-1 viral phenotypes

| Virus | Score | Temperature sensitivity (Percent titer reduction at 39° C.)$_{Fold\ reduction}$ | | | | Neurovirulence in newborn Swiss Webster mice | |
|---|---|---|---|---|---|---|---|
| | | Day 3 | Day 4 | Day 5 | Day 6 | Mortality$_n$* | AST (S.D.) |
| D1-16007 | − | $62.1_{2.6}$ | $59.3_{2.5}$ | $56.3_{2.3}$ | $(-28.5_{-1.4})$ | $6.25\%_{16}$ | 19.0 (0.0) |
| D1-PDK13 | + | $87.1_{7.8}$ | $91.3_{11.5}$ | $95.6_{22.2}$ | $96.5_{28.6}$ | $0.00\%_{16}$ | n.a. |
| VDV1 MS | + | $97.2_{35.7}$ | $97.7_{43.5}$ | $98.8_{83.3}$ | $99.5_{200.0}$ | $0.00\%_{16}$ | n.a. |

*$_n$number of animals

3.2 Genotypic Markers

VDV1 vaccine strain can be distinguished from parental strains at the genomic level. Attenuation-specific loci have been identified. These loci are conserved in master and bulk seeds.

Example 4

Immunogenicity, Viremia, and Toxicology in Monkeys

The most solid and numerous data that can be obtained in monkeys concern immunogenicity and viremia. Viremia, in particular, has been identified as one of the factors associated with virulence and disease severity in humans, and then constitutes an important parameter to consider. Obviously, immunogenicity is a key parameter when testing vaccines.

Inventors have established minimal/maximal values for viremia and immunogenicity.

TABLE 9

Minimal requirements for responses induced by Dengue vaccine candidates in monkeys, as measured in Vero or LLC-MK2 cells by plaque assay (these cells being considered equivalent in such an assay)

| Viremia mean duration (days) (all serotypes being considered) | Viremia mean peak titer (log 10 pfu) (all serotypes being considered) | Mean neutralizing titer Day 30 (for each serotype) PRNT 50 |
|---|---|---|
| ≤3 days | ≤1.5-2 | ≥80 | pfu: plaque forming unit
PRNT 50: Plaque Reduction Neutralization Titer 50 (titre corresponding to a reduction of 50% of plaque number)

4.1 Material and Methods 4.1.1 Monkey Experiments

Monkey experiments were carried out according to European guidelines regarding animal experiments.

Immunizations were performed on cynomolgus monkeys (*Macaca fascicularis*) originating from Mauritius (CRP Le Vallon). Monkeys were quarantined for 6 weeks in the animal facility of Sanofi Pasteur before immunization.

Monkeys were immunized by subcutaneous (SC) route in the arm with vaccines in a volume of 0.5 ml (see each respective section). After light anesthesia with ketamine (Imalgene, Merial), blood was collected by puncture of the inguinal or saphene veins. At days 0 and 28, 5 ml of blood were sampled for evaluating antibody responses while between days 2 and 10 only 1 ml of blood was sampled for evaluating viremia. Blood was collected on ice and kept on ice until serum separation. To do so, blood was centrifuged for 20 minutes at 4° C., and serum collected and stored at −80° C. until testing in Rich Kinney's laboratory. Shipment to USA was performed in dry ice.

4.1.2 Viremia and Neutralizing Antibody Responses (Plaque Reduction Neutralization Test, PRNT)

All analyses were performed in the laboratory of R. Kinney in CDC, Fort Collins, USA. Serum samples were shipped and stored at −80° C. until the time of testing. At the time of first thawing, the samples were tested for viremia, and a 1:5 dilution of the serum was made. The 1:5 serum dilutions were inactivated for 30 min at 56° C. before testing for neutralizing antibodies.

4.1.2.1 Viremia 0.125 ml of serum was added to 0.125 ml of diluent (RPMI medium) in the first well of 96-well plate and serial 10-fold dilution series were done, transferring 0.025 ml into 0.225 ml of diluent for each dilution. 0.2 ml of $10^{0.3}$-$10^{5.3}$ dilution series was plated in 6-well plate of Vero cells (virus was adsorbed at 37° C. for 1.5 hour, overlayed with 4 ml of agarose lacking neutral red, overlayed 6-7 days later with 2 ml of agarose containing neutral red, and plaques counted). The limit of virus detection was =10 PFU/ml. For controls stock DEN-16007 PDK-13 (LAV1) vaccine was plated.

4.1.2.2 PRNT (Plaque Reduction Neutralization Test)

Neutralizing antibodies were quantified as described in Huang et al. (2000). Briefly, 0.2 ml of heat-inactivated, 1:5 dilution of serum was added to the first well of 96-well plate and serial 2-fold dilution series were made, transferring 0.1 ml into 0.1 ml of diluent (RPMI medium) for each dilution. This resulted in a 1:10-1:320 serum dilution series. 0.1 ml of DEN virus (60-160 PFU; parental DEN1 16007 virus) was added to each serum dilution well for a total of 0.2 ml of serum-virus mixture. 96-well plates were incubated overnight at 4° C. 0.1 ml of serum-virus mixtures (containing 30-80 PFU of input virus) were plated in 6-well Vero plates (as indicated above in the Viremia section) and plaques were counted after staining with neutral red. Multiple back titrations of the input viruses at 2-fold, 1-fold, and 0.5-fold test concentrations provided direct experimental determination of the input PFU, which was the basis for determining 50% ($PRNT_{50}$) and 70% ($PRNT_{70}$) endpoint antibody titers. A negative serum result should have a neutralizing antibody titer of <1:10. Sera showing neutralization titers of 320 were retested at dilutions 1:80-1:2560 for determination of endpoint titer.

4.2 Evaluation of VDV Candidates 4.2.1 VDV 1/Pre-Master

Purification/selection of D1 candidate has been conducted as described in example 1. The selected clones (based on phenotypic markers and sequence) have been tested in sanofi pasteur as described in Material and Methods (Marcy l'Etoile animal facility, I15) on male cynomolgus macaques (*Macaca fascicularis*, mean weight 3.1 kg) originating from CRP Le Vallon, Mauritius.

After immunization on D0, viremia was followed from D2 to D10, and immunogenicity measured at D0 and D28. All viruses and vaccines, when in liquid form, were kept at −70° C.

LAV1: titre: $10^{3.9}$ $DICC_{50}$/ml; lyophilized, resuspended in 0.5 ml of PBS (containing $Ca^{2+}$ and $Mg^{2+}$; $CaCl_2.2H_2O$ 0.133 g/l; $MgCl_2.6H_2O$, 0.1 g/l) and administered in totality.

Premaster VDV1 DEN1-TV111: Titre: $10^{5.9}$ $DICC_{50}$/ml; liquid, diluted at $10^{5.3}$ pfu/ml in PBS (containing $Ca^{2+}$ and $Mg^{2+}$; $CaCl_2.2H_2O$ 0,133 g/l; $MgCl_2.6H_2O$, 0.1 g/l); 0.5 ml administered.

Injection was done by SC route in the arm with a 23G1 needle, at a $10^5$ $DICC_{50}$ dose for VDV1.

The results are as presented in Table 10. Titrations at day 28 were carried out in triplicate ($PRNT_{70}$) or in duplicate ($PRNT_{50}$).

TABLE 10

VDV1 PreMaster immunogenicity
AvP monovalent VDV1 (Exp A) DEN Monkey study
(F. Mi.DEN003.Si): PRNT and Viremia Results

| Serum | Group | Neutralizing Antibody Titer | | | | Viremia (PFU/ml in Vero cells) | | | | | | | | | |
|---|---|---|---|---|---|---|---|---|---|---|---|---|---|---|---|
| | | Day (−15) | | Day 28 | | Day −15 | Day 2 | Day 3 | Day 4 | Day 5 | Day 6 | Day 7 | Day 8 | Day 9 | Day 10 |
| | | $PRNT_{70}$ | $PRNT_{50}$ | $PRNT_{70}$ | $PRNT_{50}$ | | | | | | | | | | |
| AD 333 | LAV DEN-1 | <10/<10 | <10 | 320/160/160 | 160/320 | 0 | 0 | 0 | 0 | 0 | 0 | 0 | 0 | 0 | 0 |
| AC 763 | | <10/<10 | <10 | 640/640/640 | 1280/1280 | 0 | 0 | 0 | 0 | 0 | 0 | 0 | 0 | 50 | 150 |
| AD 209 | | <10/<10 | <10 | 320/160/160 | 160/320 | 0 | 0 | 0 | 0 | 0 | 0 | 0 | 0 | 0 | 0 |
| AC 755 | | <10/<10 | <10 | 160/80/160 | 160/160 | 0 | 0 | 0 | 0 | 0 | 0 | 50 | 0 | 0 | 0 |
| AC 775 | VDV DEN-1 | <10/<10 | <10 | 160/80/80 | 160/160 | 0 | 0 | 0 | 0 | 0 | 0 | 0 | 0 | 0 | 0 |
| AC 881 | TV111 | <10/<10 | <10 | 20/10/10 | 20/20 | 0 | 0 | 0 | 0 | 0 | 0 | 0 | 0 | 0 | 0 |
| AD 145 | | <10/<10 | <10 | 320/80/80 | 160/80 | 0 | 0 | 0 | 0 | 0 | 0 | 0 | 0 | 0 | 0 |
| AD 113 | | <10/<10 | <10 | 20/10/10 | 20/20 | 0 | 0 | 0 | 0 | 0 | 0 | 0 | 0 | 0 | 0 |

| Virus | Exp#1 | Exp#2 | Exp#3 |
|---|---|---|---|
| DEN-1 | 112 PFU | 45 PFU | 101 PFU |

Briefly, responses were rather homogeneous within each group, and some clear tendencies could be identified for each construct. No dramatic differences were found between VDV1 and LAV1: low and late viremia was observed in some LAV1 monkeys. VDV1 looked satisfactory, and in particular presented no viremia.

Viremia and immunogenicity have been measured as usual in CDC by R Kinney. The results are shown in Table 11.

VDV1 monovalent vaccine induced a significant immune response while viremia was absent. Thus, this monovalent VDV1 fulfilled the success criteria initially defined in monkeys.

TABLE 11

VDV Bulk VDV1 immunogenicity and viremia
Monkey study (F.MI.DEN004.Mk): Monovalent and Tetravalent VDV1

| Monkey | Group | Neutralizing Antibody Titer | | | | Viremia (PFU/ml in Vero cells) | | | | | | | | |
|---|---|---|---|---|---|---|---|---|---|---|---|---|---|---|
| | | Day (−14) | | Day 28 | | Day −14 | Day 2 | Day 3 | Day 4 | Day 5 | Day 6 | Day 7 | Day 8 | Day 9 |
| | | $PRNT_{50}$ | $PRNT_{70}$ | $PRNT_{50}$ | $PRNT_{50}$ | | | | | | | | | |
| AE 484 | VDV DEN-1 | — | — | 14 | 5 | 0 | 0 | 0 | 0 | 0 | 0 | 0 | 0 | 0 |
| AE 627 | | — | — | 8122 | 4558 | 0 | 0 | 0 | 0 | 5 | 0 | 0 | 0 | 0 |
| AF 115 | | — | — | 359 | 202 | 0 | 0 | 0 | 0 | 0 | 0 | 0 | 0 | 0 |
| AF 227 | | — | — | 557 | 367 | 0 | 5 | 0 | 5 | 0 | 0 | 0 | 0 | 0 |
| Geo Mean | Homologous response | — | — | 388 | 203 | | | | | | | | | |
| AE 538 | Placebo | —/—/—/— | —/—/—/— | 2.5/—/2/2 | —/—/—/— | 0 | 0 | 0 | 0 | 0 | 0 | 0 | 0 | 0 |
| AE 548 | | —/—/—/— | —/—/—/— | —/—/1/2 | —/—/—/— | 0 | 0 | 0 | 0 | 0 | 0 | 0 | 0 | 0 |
| AE 556 | | —/—/1.5/2 | —/—/—/— | 1/—/—/— | —/—/—/— | 0 | 0 | 0 | 0 | 0 | 0 | 0 | 0 | 0 |
| AE 572 | | —/—/1.5/5 | —/—/1.5/2 | 5/—/—/2 | —/—/—/— | 0 | 0 | 0 | 0 | 0 | 0 | 0 | 0 | 0 |
| Geo Mean | Response against the four serotypes | —/—/1.2/3 | —/—/1/1 | 2/—/1.2/1.6 | —/—/—/— | | | | | | | | | |
| | | D 1/D 2/ D 3/D 4 | D 1/D 2/ D 3/D 4 | D 1/D 2/ D 3/D 4 | D 1/D 2/ D 3/D 4 | | | | | | | | | |

4.2.2 VDV 1 Bulk

As immunogenicity of the vaccines had been tested at the Premaster stage, a further experiment was designed to test each monovalent at the Bulk stage.

Male *Macaca fascicularis* monkeys were used as before, originating from C.R.P. Le Vallon, Ile Maurice (24 monkeys, mean weight 3.4 kg).

VDV1; Batch: Titre: 8.37 log 10 $DICC_{50}$/ml

Placebo: PBS with $Ca^{2+}$ and $Mg^{2+}$

Vaccines were diluted at $10^{5.3}$ $DICC_{50}$/ml in PBS (containing $Ca^{2+}$ and $Mg^{2+}$; $CaCl_2.2H_2O$ 0.133 g/l; $MgCl_2.6H_2O$, 0.1 g/l); 0.5 ml administered by SC route in the arm with a 23G1 needle, corresponding to a dose of $10^5$ $DICC_{50}$.

4.3 Neurovirulence Tests in Monkeys

For each virus type, 10 cynomolgus monkeys from Mauritius were inoculated with VDV1 master seed by the intracerebral route ($10^{7.23}$ $CCID_{50}$/mL in the thalamus of each hemisphere). At the end of the test, the monkeys were sacrificed and perfused with formaline solution. Tissue samples were taken from the brain of each monkey (medulla oblongata, pons and cerebellum, midbrain, thalamus including the left and the right parts, the left and the right of the cerebral cortex). Sections were cut at a thickness of 8 µm and stained by eosin and gallocyanin.

No histopathological signs of pathogenicity were observed in the monkey brains injected with VDV1 seeds.

Example 5

Safety of Monovalent VDV1 in Healthy, Flavivirus-Naive Adults Aged 18 to 40 Years The aim of this phase 1 trial is to document the safety, viremia, and immunogenicity profiles of monovalent VDV1 at a virus concentration of $10^4$ $CCID_{50}$ compared to Stamaril® (used as control group) in flavivirus-naive adults. Single injections are given, with follow-up at 6 and 12 months. For safety precaution, sequential inclusions are performed in the study.

Enrollment and vaccinations are therefore staggered; a 1st cohort (n=4 per group, total n=12) have been vaccinated. The safety data collected up to Day 28 have been reviewed by an Independent Data Monitoring Committee (IDMC) and by the Royal Adelaide Hospital Investigational Drugs Subcommittee (IDSC) before deciding to proceed with the vaccination of the remaining subjects (n=8 per group, total n=16). A schematic representation of the trial design is provided in FIG. 6.

After administration of the vaccine the patient are regularly submitted to various clinical examination and testing. A summary of this follow up is given in table 12 below.

The enrolled population consists of adults aged 18 to 40 years (i.e. the day of the 18th birthday to the day before the 41st birthday) on day of inclusion who are flaviviruses-naive [persons presenting vaccination against flavivirus diseases (e.g. yellow fever, Japanese encephalitis, dengue fever); or history of flavivirus infection (confirmed either clinically, serologically or microbiologically) or previous residence in or travel to areas with high dengue infection endemicity (whatever the duration), or residence in or travel to North Queensland for 2 weeks or more) were excluded]

The products tested are:

The vaccine evaluated is a lyophilised product in a vial that is reconstituted extemporaneously with the diluent provided separately:

Active ingredient: $4\pm0.5$ $\log_{10}$ $CCID_{50}$ of either monovalent Vero dengue virus serotype 1 (VDV1) per 0.5 mL dose;

Diluent: Sterile NaCl 4% solution for vaccine reconstitution.

The reconstituted vaccine, i.e 0.5 mL of NaCl 4%0 solution of monovalent VDV1, should be used immediately or be maintained until use +2° C. and +8° C.

The 0.5 mL vaccine dose is administered subcutaneously in the deltoid region.

The control vaccine Stamaril®, is a yellow fever vaccine produced by Aventis Pasteur. Stamaril® is presented as a lyophilised, avian-leukosis-free, stabilised product to be reconstituted with a diluent immediately before use. (Active ingredient: Live attenuated yellow fever virus (17D strain): ≥1,000 mouse Lethal Dose 50% ($LD_{50}$)/Diluent: Sterile NaCl 4% solution).

The control vaccine is administered subcutaneously in the deltoid region.

The preliminary results of the trial are reported in Table 13 below.

TABLE 12

Flow chart for follow up

| Visit Number | V 01 | V 02 | V 03 | V 04 | V 05 | V 06 | V 07 | V 08 | V 09 | V 10 | V 11 | V 12 |
|---|---|---|---|---|---|---|---|---|---|---|---|---|
| Trial timelines¤ | D 0 | D 2 | D 4 | D 6 | D 8 | D 10 | D 12 | D 14 | D 16 | D 28 | D 180 | D 365 |
| Time Windows | | | | | | ±1 d | ±1 d | | | ±4 d | ±15 d | ±30 d |
| Clinical Examination | ✓ | ✓ | ✓ | ✓ | ✓ | ✓ | ✓ | ✓ | ✓ | ✓ | ✓ | ✓ |
| Vital signs (BP, pulse rate) | ✓ | | | | | | | | | | | |
| Oral temperature | ✓ | ✓ | ✓ | ✓ | ✓ | ✓ | ✓ | ✓ | ✓ | ✓ | | |
| Blood Sampling: | | | | | | | | | | | | |
| Serology HBV/HCV/HIV | ✓ | | ✓ | | ✓ | | ✓ | | ✓ | ✓ | | |
| Biological Safety | ✓ | ✓ | ✓ | ✓ | ✓ | ✓ | ✓ | ✓ | ✓ | | | |
| Viremia | ✓ | ✓ | ✓ | ✓ | ✓ | ✓ | ✓ | ✓ | ✓ | ✓ | ✓ | ✓ |
| Immunogenicity | ✓ | ✓ | ✓ | ✓ | ✓ | ✓ | ✓ | ✓ | ✓ | ✓ | | |
| Cytokines in serum | ✓ | | | | | | | | | ✓ | | |
| PBMCs for T cell (subset) | ✓ | | | | | | | | | ✓ | | |
| immediate surveillance | ✓ | | | | | | | | | | | |
| Local & systemic events | ✓ | ✓ | ✓ | ✓ | ✓ | ✓ | ✓ | ✓ | ✓ | ✓ | ✓ | ✓ |

V: visit - D: day
¤ Time intervals between visits will be calculated from the date of study vaccination which might differ from the date of visit (e.g. in case a temporary exclusion criterion is met). V 06 and V 07 must be done with at least 1-day interval.

TABLE 13

| | preliminary safety data | | | | | | | | | | | | | |
|---|---|---|---|---|---|---|---|---|---|---|---|---|---|---|
| | Day 0 | Day 1 | Day 2 | Day 3 | Day 4 | Day 5 | Day 6 | Day 7 | Day 8 | Day 9 | Day 10 | Day 11 | Day 12 | Day 13 |
| LOCAL SOLICITED | | | | | | | | | | | | | | |
| Pain | 1 | | | | | | | | | | | | | |
| Erythema | | | | | | | | | | | | | | |

TABLE 13-continued preliminary safety data

| | Day 0 | Day 1 | Day 2 | Day 3 | Day 4 | Day 5 | Day 6 | Day 7 | Day 8 | Day 9 | Day 10 | Day 11 | Day 12 | Day 13 |
|---|---|---|---|---|---|---|---|---|---|---|---|---|---|---|
| Induration | | | | | | | | | 1 | | | | | |
| Edema | | | | | | | | | | | | | | |
| LOCAL UNSOLICITED | | | | | | | | | | | | | | |
| Bruise | | 1 | 1 | | | | | | | | | | | |
| Pruritis | | | | | | | | | | | | | | |
| OTHER SOLICITED | | | | | | | | | | | | | | |
| Temp ≥ 37.5 C. | | | 1 | | | 1 | | | | | | | | |
| Rigors | | | 1 | 1 | | | | | 1 | | | | | |
| Malaise | | 2 | 1 | 1 | 1 | 1 | 1 | 1 | 1 | | | 2 | 1 | 2 |
| Asthenia | | 1 | 2 | 1 | 1 | 2 | 1 | | 1 | | | 2 | 1 | 1 |
| Anorexia | | | 1 | 1 | 1 | | | | | | | 1 | 1 | 1 |
| Nausea | | 1 | 2 | 1 | | 1 | 1 | | 1 | | | 1 | 1 | 2 |
| Vomiting | | | 1 | 1 | | 1 | 1 | | | | | 1 | 1 | |
| Stomach Pain | 1 | 1 | 2 | 2 | 1 | 1 | 1 | | 1 | | | 1 | 1 | 1 |
| Headache | 2 | 1 | 2 | 2 | | 1 | 1 | 1 | 2 | 1 | | 1 | 1 | 1 |
| Myalgia | | | 1 | 1 | | 1 | | | | | | 1 | 1 | 2 |
| Arthralgia | | | 1 | 1 | | 1 | 1 | | | | | 1 | 1 | 1 |
| Avoidance of light | | | | | | | 1 | 1 | | | | 1 | | |
| Conjunctivitis | | | | | | | | | | | | | | |
| Eye Pain | | | | | | | 1 | 1 | | | | | | |
| RASH | | | | | | | | | | | | | | |
| Macular | | | | | | | | | | 1 (1%) | | | | |
| Papular | | 1 (1%) | | | | | | | | | | | | |
| Maculo-papular | | | | | | | | | | | | | 1 (90%) | 1 (90%) |
| OTHER UNSOLICITED | | | | | | | | | | | | | | |
| Decreased WCC | | | | | | | | | 2 | | 1 | | | |
| Neutropenia | | | | | | | | | 2 | | 1 | | | |
| Increased aPPT | | | | | 1 | | | | 1 | | | | | |
| Elevated CK | | | | | | | | | 1 | | | | | |
| Odd dreams | | | | | | | 1 | | | | | | | |
| Low abdo pain (kidneys/liver) | | | | | | | | | | | | 1 | 1 | 1 |
| Diarrhoea | | 1 | 1 | 1 | 1 | 1 | | | | | 1 | 1 | 1 | 1 |
| Sore throat | | | | 1 | | | | | | | | | | 1 |
| Cough | | | | | | | | | | | | | | 1 |
| Early menstruation | | | | | | | | | 1 | | | | | |
| Tiredness | | | | | | | | | | | 1 | | | |

Table 13 shows that biological abnormalities (WCC reductions, platelet count reductions) have all been mild. The symptoms have been mainly malaise, nausea, diarrhoea and occasional vomiting. They have been of moderate severity. One significant rash—typical "viral" maculopapular rash, onset day 12, 90% coverage.

The safety data of the second cohort are also satisfactory with no biological abnormality recorded. All subjects have antibody response 28 days after vaccination against dengue 1 (titer between 1315 and 13150).

REFERENCES

The following references are incorporated herein by reference as if set forth in their entirety herein:

Bhamarapravati, N and Yoksan S. (1997). Dengue and Dengue Hemorrhagic Fever. Live attenuated tetravalent dengue vaccines, CABI Publishing, 367-379.

DeFraites R F, Smoak B L, Trofa A F, Hoke C H, Kanesathasan N, King A, MacArthy P O, et al. Dengue fever among U.S. military personnel—Haiti, September-November, 1994. MMWR 1994; 43: 845-848.

Dunnen and Antonarakis (2000) Mutation nomenclature extensions and suggestions to describe complex mutations: a discussion. Hum Mutation. 15:7-12; Erratum in: Hum Mutat 2002; 20(5):403

Gubler D J. Dengue. (1988) In: Epidemiology of arthropod-borne viral disease. Monath T P M, editor, Boca Raton (Fla.): CRC Press: 223-60

Gubler D J, Kuno G. Dengue and Dengue Hemorrhagic Fever. CAB International Publishing 1997

Gubler D. Epidemic dengue/dengue hemorrhagic fever as a public health, social and economic problem in the 21st century. (2002) TRENDS in Microbiology. 10:100-103

Huang et al. (2000). J. Virol 74; 3020-3028.

Kautner I, Robinson M J, Kubnle U. (1997) Dengue Virus infection: Epidemiology, pathogenesis, clinical presentation, diagnosis, and prevention. J of Pediatrics; 131:516-524

Monath, T P. (1994) Dengue: the risk to developed and developing countries. Proc Natl Acad Sci; 91: 2395-2400.

Rigau-Pérez J G, Clark G G, Gubler D J, Reiter P, Sanders E J, Vorndam A V. (1998) Dengue and dengue haemorrhagic fever. Lancet; 352: 971-977.

Rothman A L, Ennis F A. (1999) Immunopathogenesis of dengue hemorrhagic fever. Virology; 257: 1-6

Sabin A B. (1952) Research on dengue during World War II. Am J Trop Med Hyg; 1: 30-50

Shirtcliffe P, Cameron E, Nicholson K G, Wiselka M J. (1998) Don't forget dengue! Clinical features of dengue fever in returning travellers. J Roy Coll Phys Lond.; 32: 235-237.

Thompson J D, Higgins D G, and Gibson T J. (1994) CLUSTAL W: improving the sensitivity of progressive multiple sequence alignment through sequence weighting, position-specific gap penalties and weight matrix choice. Nucl. Acids. Res., 22 (22), 4673-4680

Vaughn D W, Green S, Kalayanarooj S, Innis B L, Nimmannitya S, Suntayakorn S, Rothman A L, Ennis F A, Nisalak A. (1997) Dengue in the early febrile phase: viremia and antibody response. J Infect Dis; 176: 322-30.

Vaughn D W, Green S, Kalayanarooj S, Innis B L, Nimmannitya S, Suntayakorn S, Endy T P, Raengsakulrach B, Rothman A L, Ennis F A, Nisalak A. (2000) Dengue viremia titer, antibody response pattern, and virus serotype correlate with disease severity. J Inf Dis; 181: 2-9.

WHO Technical Guide, 1986. Dengue haemorrhagic fever: diagnosis, treatment and control, p 1-2. World Health Organization, Geneva, Switzerland Wu S, Grouard-Vogel G, Sun W, Mascola J, Brachtel E, Putvatana R. (2000) Human skin Langerhans cells are targets of dengue virus infection. Nature Med; 7:816-820

What is claimed is:

1. A live attenuated dengue-1 virus strain which comprises an RNA sequence having the sequence of SEQ ID NO: 3 wherein said RNA sequence comprises uridines in place of the deoxythymidines in SEQ ID NO: 3, wherein at least nucleotides at positions 5962 and 7947 of the RNA sequence are mutated with reference to SEQ ID NO: 3, with the proviso that the following nucleotides of the RNA sequence are not mutated: 1323, 1541, 1543, 1545, 1567,1608, 2363, 2695, 2782, 5063, 6048, 6806, 7330, and 9445.

2. The dengue-1 virus strain according to claim 1, wherein the RNA sequence comprises a further mutation at position 2719 with reference to SEQ ID NO: 3.

3. The dengue-1 virus strain according to claim 1, wherein the RNA sequence comprises the mutations 2719 G>A, 5962 C>A and 7947 A>G with reference to SEQ ID NO: 3.

4. The dengue-1 virus strain according to claim 1, wherein the RNA sequence further comprises a substitution of one or more nucleotides in a given codon position with reference to SEQ ID NO: 3, which results in no alteration in the amino acid encoded at that position, with reference to the amino acid encoded by SEQ ID NO: 3.

5. The dengue-1 virus strain according to claim 1, which comprises an RNA sequence having the sequence of SEQ ID NO: 1 wherein said RNA sequence comprises uridines in place of the deoxythymidines in SEQ ID NO: 1.

6. An immunogenic composition comprising a live attenuated dengue-1 virus strain according to claim 1, in a pharmaceutically acceptable carrier.

7. The immunogenic composition according to claim 6, which is a monovalent immunogenic composition.

8. The immunogenic composition according to claim 6, which is a multivalent dengue immunogenic composition.

9. The immunogenic composition according to claim 8, which comprises a live attenuated dengue-2 virus strain which comprises an RNA sequence having the sequence of SEQ ID NO: 40 wherein said RNA sequence comprises uridines in place of the deoxythymidines in SEQ ID NO: 40.

10. The immunogenic composition according to claim 6, which contains 10 to $10^6$ $CCID_{50}$ of said live attenuated dengue-1 virus strain.

* * * * *

SEQUENCE LISTING

```
<160> NUMBER OF SEQ ID NOS: 44

<210> SEQ ID NO 1
<211> LENGTH: 10735
<212> TYPE: DNA
<213> ORGANISM: Dengue virus
<220> FEATURE:
<221> NAME/KEY: misc_feature
<222> LOCATION: (1)..(10654)
<223> OTHER INFORMATION: VDV1

<400> SEQUENCE: 1
agttgttagt ctacgtggac cgacaagaac agtttcgaat cggaagcttg cttaacgtag     60
ttctaacagt tttttattag agagcagatc tctgatgatc aaccaacgaa aaaagacggg    120
tcgaccgtct ttcaatatgc tgaaacgcgc gagaaaccgc gtgtcaactg tttcacagtt    180
ggcgaagaga ttctcaaaag gattgctctc aggccaagga cccatgaaat tggtgatggc    240
tttcatagca ttcttaagat ttctagccat acccccaaca gcaggaattt tggctagatg    300
gggctcattc aagaagaatg gagcgattaa agtgttacgg ggtttcaaga gagaaatctc    360
aaacatgcta aacataatga acaggaggaa aagatccgtg accatgctcc ttatgctgct    420
gcccacagcc ctggcgttcc atctgacgac acgaggggga gagccgcata tgatagttag    480
caagcaggaa agaggaaagt cacttttgtt caagacctct gcaggtgtca acatgtgcac    540
cctcattgcg atggatttgg gagagttgtg tgaggacacg atgacctaca aatgcccccg    600
gatcactgag gcggaaccag atgacgttga ctgttggtgc aatgccacgg acacatgggt    660
gacctatgga acgtgctctc aaactggcga acaccgacga gacaaacgtt ccgtcgcatt    720
ggccccacac gtggggcttg gcctagaaac aagagccgaa acgtggatgt cctctgaagg    780
tgcttggaaa cagatacaaa aagtagagac ttgggctctg agacatccag gattcacggt    840
gatagccctt tttctagcac atgccatagg aacatccatc acccagaaag ggatcatttt    900
cattttgctg atgctggtaa caccatctat ggccatgcga tgcgtgggaa taggcaacag    960
agacttcgtg gaaggactgt caggagcaac atgggtggat gtggtactgg agcatggaag   1020
ttgcgtcacc accatggcaa aaaacaaacc aacactggac attgaactct tgaagacgga   1080
ggtcacaaac cctgcagttc tgcgtaaatt gtgcattgaa gctaaaatat caaacaccac   1140
caccgattcg agatgtccaa cacaaggaga agccacactg gtggaagaac aagacgcgaa   1200
ctttgtgtgc cgacgaacgt tcgtggacag aggctggggc aatggctgtg ggctattcgg   1260
```

```
aaaaggtagt ctaataacgt gtgccaagtt taagtgtgtg acaaaactag aaggaaagat    1320
agctcaatat gaaaacctaa aatattcagt gatagtcacc gtccacactg agatcagca     1380
ccaggtggga aatgagacta cagaacatgg aacaactgca accataacac ctcaagctcc    1440
tacgtcggaa atacagctga ccgactacgg aacccttaca ttagattgtt cacctaggac    1500
agggctagat tttaacgaga tggtgttgct gacaatgaaa aagaaatcat ggcttgtcca    1560
caaacagtgg tttctagact taccactgcc ttggacctct ggggctttaa catcccaaga    1620
gacttggaac agacaagatt tactggtcac atttaagaca gctcatgcaa agaagcagga    1680
agtagtcgta ctaggatcac aagaaggagc aatgcacact gcgctgactg gagcgacaga    1740
aatccaaacg tcaggaacga caacaatttt cgcaggacac ctaaaatgca gactaaaaat    1800
ggacaaacta actttaaaag ggatgtcata tgtgatgtgc acaggctcat tcaagttaga    1860
gaaagaagtg gctgagaccc agcatggaac tgttctggtg caggttaaat atgaaggaac    1920
agacgcacca tgcaagattc ccttttcgac ccaagatgag aaaggagcaa cccagaatgg    1980
gagattaata acagccaacc ccatagtcac tgacaaagaa aaaccagtca atattgaggc    2040
agaaccaccc tttggtgaga gctacatcgt ggtaggagca ggtgaaaaag ctttgaaact    2100
aagctggttc aagaaggaa gcagcatagg gaaaatgttt gaagcaactg cccgaggagc    2160
acgaaggatg gccattctgg agacaccgc atgggacttc ggttctatag gaggagtgtt    2220
cacgtctatg ggaaaactgg tacaccaggt ttttggaact gcatatggag ttttgttag    2280
cggagttct tggaccatga aaataggaat agggattctg ctgacatggc taggattaaa    2340
ttcaaggaac acgtccctt cggtgatgtg catcgcagtt ggcatggtca cactgtacct    2400
aggagtcatg gttcaggcag attcgggatg tgtaatcaac tggaaaggca gagaacttaa    2460
atgtggaagc ggcattttg tcactaatga agttcacact tggacagagc aatacaaatt    2520
ccaggctgac tcccccaaga gactatcagc agccattggg aaggcatggg aggagggtgt    2580
gtgtggaatc cgatcagcca ctcgtctcga gaacatcatg tggaaacaaa tatcaaatga    2640
attgaaccac atcctacttg aaaatgacat gaaatttaca gtggtcgtgg gagacgttag    2700
tggaatcttg gcccaaggaa aaaaatgat taggccacaa cccatggaac acaaatactc    2760
gtggaaaagc tggggaaaag ctaaaatcat aggagcggat gtacagaaca ccaccttcat    2820
catcgacggc ccaaacaccc cagaatgccc tgacaatcaa agagcatgga atatttggga    2880
agtagaggac tatggatttg ggatttttcac gacaaacata tggttgaaat tgcgtgactc    2940
ctacacccaa gtatgtgacc accggctgat gtcagctgcc attaaggaca gcaaggcagt    3000
ccatgctgac atgggtact ggatagaaag tgaaaagaac gagacatgga gttggcgag     3060
agcctccttt atagaagtta agacatgcat ctggccaaaa tcccacactc tatggagcaa    3120
tggagttctg gaaagtgaaa tgataattcc aaagatatat ggaggaccaa tatctcagca    3180
caactacaga ccaggatatt tcacacaaac agcagggccg tggcacctag caagttgga    3240
actagatttc gattttttgtg aaggtaccac agttgttgtg gatgaacatt gtggaaatcg    3300
aggaccatct ctcagaacca acagtcac aggaaagata atccatgaat ggtgctgcag    3360
atcttgtacg ctacccccc tacgtttcaa agggaagac gggtgttggt acggcatgga    3420
aatcagacca gtgaaggaca aggaagagaa cctggtcaag tcaatggtct ctgcagggtc    3480
aggagaagtg gacagctttt cactaggact gctatgcata tcaataatga ttgaagaagt    3540
gatgagatcc agatgagca aaaaaatgct gatgactgga acactggctg tgttcctcct    3600
tcttataatg ggacaattga catggagtga tctgatcagg ttatgtatta tggttggagc    3660
```

| | |
|---|---|
| caacgcttca gacaagatgg ggatgggaac aacgtaccta gctttaatgg ccactttcaa | 3720 |
| aatgagacca atgttcgccg tcgggctatt atttcgcaga ctaacatcta gagaagttct | 3780 |
| tcttcttaca attggcttga gcctggtggc atccgtggag ctaccaagtt ccctagagga | 3840 |
| gctgggggat ggacttgcaa taggcatcat gatgttgaaa ttattgactg attttcagtc | 3900 |
| acaccagcta tgggctactc tgctatcctt gacatttatt aaaacaactt tttcattgca | 3960 |
| ctatgcatgg aagacaatgg ctatggtact gtcaattgta tctctcttcc ctttatgcct | 4020 |
| gtccacgacc tctcaaaaaa caacatggct tccggtgctg ttgggatctc ttggatgcaa | 4080 |
| accactaccc atgtttctta taacagaaaa caaaatctgg ggaaggaaga gttggcccct | 4140 |
| caatgaagga attatggctg ttggaatagt tagtattcta ctaagttcac ttttaaaaaa | 4200 |
| tgatgtgccg ctagccggcc cattaatagc tggaggcatg ctaatagcat gttatgtcat | 4260 |
| atccggaagc tcagctgatt tatcactgga gaaagcggct gaggtctcct gggaggaaga | 4320 |
| agcagaacac tcaggcgcct cacacaacat actagtagag gttcaagatg atggaaccat | 4380 |
| gaagataaaa gatgaagaga gagatgacac gctcaccatt ctccttaaag caactctgct | 4440 |
| ggcagtctca ggggtgtacc caatgtcaat accagcgacc cttttgtgt ggtattttg | 4500 |
| gcagaaaaag aaacagagat caggagtgct atgggacaca cccagccccc cagaagtgga | 4560 |
| aagagcagtt cttgatgatg gcatctatag aattttgcaa agaggactgt tgggcaggtc | 4620 |
| ccaagtagga gtaggagttt tccaagaagg cgtgttccac acaatgtggc acgtcactag | 4680 |
| gggagctgtc ctcatgtatc aaggaaaaag gctggaacca agctgggcca gtgtcaaaaa | 4740 |
| agacttgatc tcatatggag gaggttggag gtttcaagga tcctggaaca cgggagaaga | 4800 |
| agtacaggtg attgctgttg aaccgggaaa aaaccccaaa aatgtacaaa caacgccggg | 4860 |
| taccttcaag ccccctgaag gcgaagttgg agccatagcc ttagacttta aacctggcac | 4920 |
| atctggatct cccatcgtaa acagagaggg aaaaatagta ggtctttatg gaaatggagt | 4980 |
| ggtgacaaca agcggaactt acgttagtgc catagctcaa gctaaggcat cacaagaagg | 5040 |
| gcctctacca gagattgagg acaaggtgtt taggaaaaga aacttaacaa taatggacct | 5100 |
| acatccagga tcgggaaaaa caagaagata ccttccagcc atagtccgtg aggccataaa | 5160 |
| aaggaagctg cgcacgctaa tcctagctcc cacaagagtt gtcgcttctg aaatggcaga | 5220 |
| ggcactcaag ggagtgccaa taggtatca gacaacagca gtgaagagtg aacacacagg | 5280 |
| aaaggagata gttgacctta tgtgccacgc cactttcacc atgcgcctcc tgtctcccgt | 5340 |
| gagagttccc aattataaca tgattatcat ggatgaagca cacttcaccg atccagccag | 5400 |
| catagcagcc agagggtaca tctcaacccg agtgggtatg ggtgaagcag ctgcgatctt | 5460 |
| tatgacagcc actcccccag gatcggtgga ggcctttcca cagagcaatg caattatcca | 5520 |
| agatgaggaa agagacattc ctgagagatc atggaactca ggctatgact ggatcactga | 5580 |
| ttttccaggt aaaacagtct ggtttgttcc aagcatcaaa tcaggaaatg acattgccaa | 5640 |
| ctgtttaaga aaaacggga aacgggtgat ccaattgagc agaaaaacct tgacactga | 5700 |
| gtaccagaaa acaaaaaaca acgactggga ctatgtcgtc acaacagaca tttccgaaat | 5760 |
| gggagcaaat ttccgggccg acaggtaat agacccaagg cggtgtctga accggtaat | 5820 |
| actaaaagat ggtccagagc gcgtcattct agccggaccg atgccagtga ctgtggccag | 5880 |
| tgccgcccag aggagaggaa gaattggaag gaaccaaaac aaggaaggtg atcagtatat | 5940 |
| ttacatggga cagcctttaa aaaatgatga ggaccacgct cattggacag aagcaaagat | 6000 |

-continued

```
gctccttgac aatataaaca caccagaagg gattatccca gccctctttg agccggagag      6060
agaaaagagt gcagctatag acggggaata cagactgcgg ggtgaagcaa ggaaaacgtt      6120
cgtggagctc atgagaagag gggatctacc agtctggcta tcctacaaag ttgcctcaga      6180
aggcttccag tactccgaca gaaggtggtg cttcgatggg gaaaggaaca accaggtgtt      6240
ggaggagaac atggacgtgg agatctggac aaaagaagga gaaagaaaga aactacgacc      6300
tcgctggttg gacgccagaa catactctga cccactggct ctgcgcgagt ttaaagagtt      6360
tgcagcagga agaagaagcg tctcaggtga cctaatatta gaaatagggga aacttccaca      6420 acatttgacg caaagggccc agaatgcttt ggacaacttg gtcatgttgc acaattccga      6480
acaaggagga aaagcctata gacatgctat ggaagaactg ccagacacaa tagaaacgtt      6540
gatgctccta gccttgatag ctgtgttgac tggtggagtg acgctgttct tcctatcagg      6600
aagaggtcta ggaaaaacat ctatcggctt actctgcgtg atggcctcaa gcgcactgtt      6660
atggatggcc agtgtggagc cccattggat agcggcctcc atcatactgg agttctttct      6720
gatggtactg cttattccag agccagacag acagcgcact ccacaggaca accagctagc      6780
atatgtggtg ataggtctgt tattcgtgat attgacagtg gcagccaatg agatgggatt      6840
attggaaacc acaaagaaag acctgggat tggccatgta gctgctgaaa accaccacca      6900
tgctacaatg ctggacgtag acctacatcc agcttcagcc tggaccctct atgcagtggc      6960
cacaacaatc atcactccta tgatgagaca cacaattgaa aacacaacgg caaatatttc      7020
cctgacagcc atcgcaaacc aagcagctat attgatggga cttgacaagg gatggccaat      7080
atcgaagatg gacataggag ttccacttct cgccttgggg tgctattccc aagtgaatcc      7140
gctgacactg atagcggcag tattgatgct agtagctcat tacgccataa ttggacctgg      7200
actgcaagca aaagctacta gagaagctca aaaagaaca gcggctggaa taatgaaaaa      7260
tccaactgtc gacgggattg ttgcaataga cttagatccc gtggtttacg atgcaaaatt      7320
tgaaaaacag ctaggccaaa taatgttgtt gatactttgc acatcacaga ttcttttgat      7380
gcggactaca tgggccttgt gtgaatccat cacattggct actggacctc tgaccactct      7440
ttgggaggga tctccaggaa aattctggaa caccacaata gcggtatcca tggcaaacat      7500
tttcaggggg agttatctag caggagcagg tctggccttc tcattaatga aatctctagg      7560
aggaggtagg agaggcacgg gagcccaagg ggaaacactg ggagaaaaat ggaaaagaca      7620
actaaaccaa ctgagcaagt cagaattcaa tacttacaag aggagtggga ttatggaggt      7680
ggatagatcc gaagccaaag agggactgaa aagaggagaa acaaccaaac acgcagtatc      7740
gagaggaacg gccaaactga ggtggttcgt ggagaggaac cttgtgaaac cagaagggaa      7800
agtcatagac ctcggttgtg gaagaggtgg ctggtcatat tattgcgctg ggctgaagaa      7860
agtcacagaa gtgaaaggat acacaaaagg aggacctgga catgaggaac caatcccaat      7920
ggcgacctat ggatggaacc tagtaaggct gcactccgga aaagatgtat ttttatacc      7980 acctgagaaa tgtgacaccc ttttgtgtga tattggtgag tcctctccga acccaactat      8040
agaggaagga gaacgttac gtgttctgaa aatggtggaa ccatggctca gaggaaacca      8100
attttgcata aaaattctaa atccctatat gccgagcgtg gtagaaactc tggaacaaat      8160
gcaaagaaaa catggaggaa tgctagtgcg aaacccactc tcaagaaatt ccacccatga      8220
aatgtactgg gtttcatgtg aacaggaaa cattgtgtca gcagtaaaca tgacatctag      8280
aatgttgcta aatcggttca caatggctca caggaagcca acatatgaaa gagacgtgga      8340
cttaggcgct ggaacaagac atgtggcagt agaaccagag gtagccaacc tagatatcat      8400
```

```
tggccagagg atagagaata taaaaaatga acataagtca acatggcatt atgatgagga   8460
caatccatac aaaacatggg cctatcatgg atcatatgag gttaagccat caggatcggc   8520
ctcatccatg gtcaatggcg tggtgagatt gctcaccaaa ccatgggatg ttatccccat   8580
ggtcacacaa atagccatga ctgataccac acccttggga caacagaggg tgtttaaaga   8640
gaaagttgac acgcgcacac caaaagcaaa acgtggcaca gcacaaatta tggaagtgac   8700
agccaggtgg ttatggggtt tcctttctag aaacaaaaaa cccagaattt gcacaagaga   8760
ggagtttaca agaaaagtta ggtcaaacgc agctattgga gcagtgttcg ttgatgaaaa   8820
tcaatggaac tcggcaaaag aagcagtgga agacgaacgg ttctgggaac ttgtccacag   8880
agagagggag cttcataaac aggggaaatg tgccacgtgt gtctacaata tgatggggaa   8940
gagagagaaa aaattaggag agttcggaaa ggcaaaagga agtcgtgcaa tatggtacat   9000
gtggttggga gcacgcttcc tagagtttga agcccttggt ttcatgaatg aagatcactg   9060
gttcagtaga gagaattcac tcagtggagt ggaaggagaa ggactccaca aacttggata   9120
catactcaga gacatatcaa ggattccagg ggggaacatg tatgcagatg acacagccgg   9180
atgggacaca agaataacag aggatgatct ccagaatgag gctaaaatca ctgacatcat   9240
ggagcccgaa catgccctgc tggctacgtc aatctttaag ctgacctacc aaaataaggt   9300
ggtaagggtg cagagaccag caaaaaatgg aaccgtgatg gatgttatat ccagacgtga   9360
ccagagaggc agtggacagg ttggaactta tggcttaaac actttcacca acatggaggc   9420
ccaactgata agacaaatgg agtctgaggg aatcttttta cccagcgaat tggaaacccc   9480
aaatctagcc ggaagagttc tcgactggtt ggaaaaatat ggtgtcgaaa ggctgaaaag   9540
aatggcaatc agcggagatg actgtgtggt gaaaccaatt gatgacaggt tcgcaacagc   9600
cttaacagct ttgaatgaca tgggaaaagt aagaaaagac ataccacaat gggaaccttc   9660
aaaaggatgg aatgattggc aacaagtgcc tttctgttca caccacttcc accagctaat   9720
tatgaaggat gggagggaga tagtggtgcc atgccgcaac caagatgaac ttgtggggag   9780
ggccagagta tcacaaggcg ccggatggag cctgagagaa accgcatgcc taggcaagtc   9840
atatgcacaa atgtggcagc tgatgtattt ccacaggaga gacctgagac tggcggctaa   9900
cgctatttgt tcagccgttc cagttgattg ggtcccaacc agccgcacca cctggtcgat   9960
ccatgcccat caccaatgga tgacaacaga agacatgtta tcagtatgga ataggtctg  10020
gatagaggaa aacccatgga tggaggataa gactcatgtg tccagttggg aagaagttcc  10080
atacctagga aagagggaag atcagtggtg tggatccctg ataggcttaa cagcaagggc  10140
cacctgggcc actaatatac aagtggccat aaaccaagtg agaaggctca ttgggaatga  10200
gaattatcta gattacatga catcaatgaa gagattcaag aatgagagtg atcccgaagg  10260
ggcactctgg taagtcaaca cattcacaaa ataaggaaa ataaaaaatc aaatgaggca  10320
agaagtcagg ccagattaag ccatagtacg gtaagagcta tgctgcctgt gagccccgtc  10380
caaggacgta aaatgaagtc aggccgaaag ccacggtttg agcaagccgt gctgcctgtg  10440
gctccatcgt ggggatgtaa aaacccggga ggctgcaacc catggaagct gtacgcatgg  10500
ggtagcagac tagtggttag aggagacccc tcccaagaca caacgcagca gcggggccca  10560
acaccagggg aagctgtacc ctggtggtaa ggactagagg ttagaggaga ccccccgcgt  10620
aacaataaac agcatattga cgctgggaga gaccagagat cctgctgtct ctacagcatc  10680
attccaggca cagaacgcca gaaaatggaa tggtgctgtt gaatcaacag gttct       10735
```

<210> SEQ ID NO 2
<211> LENGTH: 10735
<212> TYPE: DNA
<213> ORGANISM: Dengue virus
<220> FEATURE:
<221> NAME/KEY: misc_feature
<222> LOCATION: (1)..(10735)
<223> OTHER INFORMATION: Dengue virus type 1 strain 16007 polyprotein
      precursor, complete cds

<400> SEQUENCE: 2

```
agttgttagt ctacgtggac cgacaagaac agtttcgaat cggaagcttg cttaacgtag      60
ttctaacagt tttttattag agagcagatc tctgatgatc aaccaacgaa aaaagacggg     120
tcgaccgtct ttcaatatgc tgaaacgcgc gagaaaccgc gtgtcaactg tttcacagtt     180
ggcgaagaga ttctcaaaag gattgctctc aggccaagga cccatgaaat tggtgatggc     240
tttcatagca ttcttaagat ttctagccat accccccaaca gcaggaattt tggctagatg     300
gggctcattc aagaagaatg gagcgattaa agtgttacgg ggtttcaaga gagaaatctc     360
aaacatgcta acataatga acaggaggaa aagatccgtg accatgctcc ttatgctgct     420
gcccacagcc ctggcgttcc atctgacgac acgaggggga gagccgcata tgatagttag     480
caagcaggaa agaggaaagt cacttttgtt caagacctct gcaggtgtca acatgtgcac     540
cctcattgcg atggatttgg gagagttgtg tgaggacacg atgacctaca atgccccccg     600
gatcactgag gcggaaccag atgacgttga ctgttggtgc aatgccacgg acacatgggt     660
gacctatgga acgtgctctc aaactggcga acaccgacga gacaaacgtt ccgtcgcatt     720
ggccccacac gtgggcttgg cctagaaaac aagagccgaa acgtggatgt cctctgaagg     780
tgcttggaaa cagatacaaa agtagagac ttgggctctg agacatccag gattcacggt     840
gatagccctt tttctagcac atgccatagg aacatccatc acccagaaag ggatcatttt     900
cattttgctg atgctggtaa caccatctat ggccatgcga tgcgtgggaa taggcaacag     960
agacttcgtg gaaggactgt caggagcaac atgggtggat gtggtactgg agcatggaag    1020
ttgcgtcacc accatggcaa aaacaaaacc aacactggac attgaactct tgaagacgga    1080
ggtcacaaac cctgcagttc tgcgtaaatt gtgcattgaa gctaaaatat caacaccac    1140 caccgattcg agatgtccaa cacaaggaga agccacactg gtggaagaac aagacgcgaa    1200 cttttgtgtgc cgacgaacgt tcgtggacag aggctgggc aatggctgtg gctattcgg    1260 aaaaggtagt ctaataacgt gtgccaagtt taagtgtgtg acaaaactag aaggaaagat    1320
agttcaatat gaaaacctaa aatattcagt gatagtcacc gtccacactg agatcagca    1380 ccaggtggga aatgagacta cagaacatgg aacaactgca accataacac ctcaagctcc    1440
tacgtcggaa atacagctga ccgactacgg aaccctttaca ttagattgtt cacctaggac    1500
agggctagat tttaacgaga tggtgttgct gacaatgaaa gaaaagatca tggcttgtcca    1560 caaacaatgg tttctagact accactgcc ttggaccctct ggggcttcaa catcccaaga    1620
gacttggaac agacaagatt tactggtcac atttaagaca gctcatgcaa agaagcagga    1680
agtagtcgta ctaggatcac aagaaggagc aatgcacact gcgctgactg gagcgacaga    1740
aatccaaacg tcaggaacga caacaatttt cgcaggacac ctaaaatgca gactaaaaat    1800
ggacaaacta actttaaaag ggatgtcata tgtgatgtgc acaggctcat tcaagttaga    1860
gaaagaagtg gctgagaccc agcatggaac tgttctggtg caggttaaat atgaaggaac    1920
agacgcacca tgcaagattc cctttttcgac ccaagatgag aaaggagcaa cccagaatgg    1980
```

```
gagattaata acagccaacc ccatagtcac tgacaaagaa aaaccagtca atattgaggc    2040
agaaccaccc tttggtgaga gctacatcgt ggtaggagca ggtgaaaaag ctttgaaact    2100
aagctggttc aagaaaggaa gcagcatagg gaaaatgttt gaagcaactg cccgaggagc    2160
acgaaggatg gccattctgg gagacaccgc atgggacttc ggttctatag gaggagtgtt    2220
cacgtctatg ggaaaactgg tacaccaggt ttttggaact gcatatggag ttttgtttag    2280
cggagtttct tggaccatga aaataggaat agggattctg ctgacatggc taggattaaa    2340
ttcaaggaac acgtcccttt cgatgatgtg catcgcagtt ggcatggtca cactgtacct    2400
aggagtcatg gttcaggcag attcgggatg tgtaatcaac tggaaaggca gagaacttaa    2460
atgtggaagc ggcattttg tcactaatga agttcacact tggacagagc aatacaaatt    2520
ccaggctgac tcccccaaga gactatcagc agccattggg aaggcatggg aggagggtgt    2580
gtgtggaatc cgatcagcca ctcgtctcga gaacatcatg tggaaacaaa tatcaaatga    2640
attgaaccac atcctacttg aaaatgacat gaaatttaca gtggtcgtgg agatgttag     2700 tggaatcttg gcccaaggga aaaaatgat taggccacaa cccatggaac acaaatactc     2760
gtggaaaagc tggggaaaag ccaaaatcat aggagcggat gtacagaaca ccaccttcat    2820
catcgacggc ccaaacaccc cagaatgccc tgacaatcaa agagcatgga atatttggga    2880
agtagaggac tatggatttg ggattttcac gacaaacata tggttgaaat tgcgtgactc    2940
ctacacccaa gtatgtgacc accggctgat gtcagctgcc attaaggaca gcaaggcagt    3000
ccatgctgac atgggtgtact ggatagaaag tgaaaagaac gagacatgga agttggcgag    3060
agcctccttt atagaagtta agacatgcat ctggccaaaa tcccacactc tatggagcaa    3120
tggagttctg gaaagtgaaa tgataattcc aaagatatat ggaggaccaa tatctcagca    3180
caactacaga ccaggatatt tcacacaaac agcagggccg tggcacctag caagttgga     3240 actagatttc gattttgtg aaggtaccac agttgttgtg gatgaacatt gtggaaatcg     3300
aggaccatct ctcagaacca caacagtcac aggaaagata tccatgaat ggtgctgcag     3360 atcttgtacg ctaccccccc tacgtttcaa aggggaagac gggtgttggt acggcatgga    3420
aatcagacca gtgaaggaca aggaagagaa cctggtcaag tcaatggtct ctgcagggtc    3480
aggagaagtg gacagctttt cactaggact gctatgcata tcaataatga ttgaagaagt    3540
gatgagatcc agatggagca aaaaaatgct gatgactgga acactggctg tgttcctcct    3600
tcttataatg ggacaattga catggagtga tctgatcagg ttatgtatta tggttggagc    3660
caacgcttca gacaagatgg ggatgggaac aacgtaccta gctttaatgg ccactttcaa    3720
aatgagacca atgttcgccg tcgggctatt atttcgcaga ctaacatcta gagaagttct    3780
tcttcttaca attggcttga gcctggtggc atccgtggag ctaccaagtt ccctagagga    3840
gctgggggat ggacttgcaa taggcatcat gatgttgaaa ttattgactg attttcagtc    3900
acaccagcta tggctactc tgctatcctt gacatttatt aaaacaactt tttcattgca     3960
ctatgcatgg aagacaatgg ctatggtact gtcaattgta tctctcttcc ctttatgcct    4020
gtccacgacc tctcaaaaaa caacatggct tccggtgctg ttgggatctc ttggatgcaa    4080
accactaccc atgtttctta acagaaaaa caaaatctgg ggaaggaaga gttggcccct    4140
caatgaagga attatggctg ttggaatagt tagtattcta ctaagttcac ttttaaaaaa    4200
tgatgtgccg ctagccggcc cattaatagc tggaggcatg ctaatagcat gttatgtcat    4260
atccggaagc tcagctgatt tatcactgga gaaagcggct gaggtctcct gggaggaaga    4320
agcagaacac tcaggcgcct cacacaacat actagtagag gttcaagatg atggaaccat    4380
```

```
gaagataaaa gatgaagaga gagatgacac gctcaccatt ctccttaaag caactctgct    4440
ggcagtctca ggggtgtacc caatgtcaat accagcgacc cttttttgtgt ggtatttttg   4500 gcagaaaaag aaacagagat caggagtgct atgggacaca cccagccccc cagaagtgga    4560
aagagcagtt cttgatgatg gcatctatag aattttgcaa agaggactgt tgggcaggtc    4620
ccaagtagga gtaggagttt tccaagaagg cgtgttccac acaatgtggc acgtcactag    4680
gggagctgtc ctcatgtatc aaggaaaaag gctggaacca agctgggcca gtgtcaaaaa    4740
agacttgatc tcatatggag gaggttggag gtttcaagga tcctggaaca cgggagaaga    4800
agtacaggtg attgctgttg aaccgggaaa aaaccccaaa aatgtacaaa caacgccggg    4860
taccttcaag accctgaag gcgaagttgg agccatagcc ttagacttta aacctggcac     4920
atctggatct cccatcgtaa acagagaggg aaaaatagta ggtctttatg gaaatggagt    4980
ggtgacaaca agcggaactt acgttagtgc catagctcaa gctaaggcat cacaagaagg    5040
gcctctacca gagattgagg acgaggtgtt taggaaaaga aacttaacaa taatggacct    5100
acatccagga tcgggaaaaa caagaagata ccttccagcc atagtccgtg aggccataaa    5160
aaggaagctg cgcacgctaa tcctagctcc cacaagagtt gtcgcttctg aaatggcaga    5220
ggcactcaag ggagtgccaa taaggtatca gacaacagca gtgaagagtg aacacacagg    5280
aaaggagata gttgacctta tgtgccacgc cactttcacc atgcgcctcc tgtctcccgt    5340
gagagttccc aattataaca tgattatcat ggatgaagca cacttcaccg atccagccag    5400
catagcagcc agagggtaca tctcaacccg agtgggtatg ggtgaagcag ctgcgatctt    5460
tatgacagcc actcccccag gatcggtgga ggcctttcca cagagcaatg caattatcca    5520
agatgaggaa agagacattc ctgagagatc atggaactca ggctatgact ggatcactga    5580
ttttccaggt aaaacagtct ggtttgttcc aagcatcaaa tcaggaaatg acattgccaa    5640
ctgtttaaga aaaaacggga acggtgatcc caattgagc agaaaaacct ttgacactga      5700
gtaccagaaa acaaaaaaca acgactggga ctatgtcgtc acaacagaca tttccgaaat    5760
gggagcaaat ttccgggccg acagggtaat agacccaagg cggtgtctga accggtaat    5820 actaaaagat ggtccagagc gcgtcattct agccggaccg atgccagtga ctgtggccag    5880
tgccgcccag aggagaggaa gaattggaag gaaccaaaac aaggaaggtg atcagtatat    5940
ttacatggga cagcctttaa acaatgatga ggaccacgct cattggacag aagcaaagat    6000
gctccttgac aatataaaca caccagaagg gattatccca gccctctatg agccggagag    6060
agaaaagagt gcagctatag acgggggaata cagactgcgg ggtgaagcaa ggaaaacgtt    6120
cgtggagctc atgagaagag gggatctacc agtctggcta tcctacaaag ttgcctcaga    6180
aggcttccag tactccgaca aggtggtgct tcgatggg gaaggaaca accaggtgtt      6240 ggaggagaac atggacgtgg agatctggac aaaagaagga gaaagaaaga aactacgacc    6300
tcgctggttg gacgccagaa catactctga cccactggct ctgcgcgagt ttaaagagtt    6360
tgcagcagga agaagaagcg tctcaggtga cctaatatta gaaatagga aacttccaca     6420 acatttgacg caagggccc agaatgcttt ggacaacttg gtcatgttgc acaattccga      6480
acaaggagga aaagcctata gacatgctat ggaagaactg ccagacacaa tagaaacgtt    6540
gatgctccta gccttgatag ctgtgttgac tggtggagtg acgctgttct tcctatcagg    6600
aagaggtcta ggaaaaacat ctatcggctt actctgcgtg atggcctcaa gcgcactgtt    6660
atggatggcc agtgtggagc cccattggat agcggcctcc atcatactgg agttctttct    6720
```

```
gatggtactg cttattccag agccagacag acagcgcact ccacaggaca accagctagc    6780
atatgtggtg ataggtctgt tattcatgat attgacagtg gcagccaatg agatgggatt    6840
attggaaacc acaaagaaag acctggggat tggccatgta gctgctgaaa accaccacca    6900
tgctacaatg ctggacgtag acctacatcc agcttcagcc tggaccctct atgcagtggc    6960
cacaacaatc atcactccta tgatgagaca cacaattgaa aacacaacgg caaatatttc    7020
cctgacagcc atcgcaaacc aagcagctat attgatggga cttgacaagg gatggccaat    7080
atcgaagatg gacataggag ttccacttct cgccttgggg tgctattccc aagtgaatcc    7140
gctgacactg atagcggcag tattgatgct agtagctcat tacgccataa ttggacctgg    7200
actgcaagca aaagctacta gagaagctca aaaaagaaca gcggctggaa taatgaaaaa    7260
tccaactgtc gacgggattg ttgcaataga cttagatccc gtggtttacg atgcaaaatt    7320
tgaaaaacaa ctaggccaaa taatgttgtt gatactttgc acatcacaga ttcttttgat    7380
gcggactaca tgggccttgt gtgaatccat cacattggct actggacctc tgaccactct    7440
ttgggaggga tctccaggaa aattctggaa caccacaata gcggtatcca tggcaaacat    7500
tttcaggggg agttatctag caggagcagg tctggccttc tcattaatga aatctctagg    7560
aggaggtagg agaggcacgg gagcccaagg ggaaacactg ggagaaaaat ggaaaagaca    7620
actaaaccaa ctgagcaagt cagaattcaa tacttacaag aggagtggga ttatggaggt    7680
ggatagatcc gaagccaaag agggactgaa agaggagaga caaccaaac acgcagtatc    7740 gagaggaacg gccaaactga ggtggttcgt ggagaggaac cttgtgaaac cagaagggaa    7800
agtcatagac ctcggttgtg gaagaggtgg ctggtcatat tattgcgctg ggctgaagaa    7860
agtcacagaa gtgaaaggat acacaaaagg aggacctgga catgaggaac caatcccaat    7920
ggcgacctat ggatggaacc tagtaaagct gcactccgga aaagatgtat tttttatacc    7980
acctgagaaa tgtgacaccc ttttgtgtga tattggtgag tcctctccga acccaactat    8040
agaggaagga gaacgttac gtgttctgaa atggtggaa ccatggctca gaggaaacca    8100
attttgcata aaaattctaa atccctatat gccgagcgtg gtagaaactc tggaacaaat    8160
gcaaagaaaa catggaggaa tgctagtgcg aaacccactc tcaagaaatt ccacccatga    8220
aatgtactgg gtttcatgtg gaacaggaaa cattgtgtca gcagtaaaca tgacatctag    8280
aatgttgcta atcggttcaa atggctcag aggaagcca acatatgaaa gagacgtgga    8340
cttaggcgct ggaacaagac atgtggcagt agaaccagag gtagccaacc tagatatcat    8400
tggccagagg atagagaata taaaaaatga acataagtca acatggcatt atgatgagga    8460
caatccatac aaaacatggg cctatcatgg atcatatgag gttaagccat caggatcggc    8520
ctcatccatg gtcaatggcg tggtgagatt gctcaccaaa ccatgggatg ttatccccat    8580
ggtcacacaa atagccatga ctgataccac acccctttgga caacagaggg tgtttaaaga    8640
gaaagttgac acgcgcacac caaaagcaaa acgtggcaca gcacaaatta tggaagtgac    8700
agccaggtgg ttatggggtt tccttttctag aaacaaaaaa cccagaattt gcacaagaga    8760
ggagtttaca agaaaagtta ggtcaaacgc agctattgga gcagtgttcg ttgatgaaaa    8820
tcaatggaac tcggcaaaag aagcagtgga agacgaacgg ttctgggaac ttgtccacag    8880
agagagggag cttcataaac agggaaatg tgccacgtgt gtctacaata tgatggggaa    8940
gagagagaaa aaattaggag agttcggaaa ggcaaaagga agtcgtgcaa tatggtacat    9000
gtggttggga gcacgcttcc tagagtttga agcccttggt ttcatgaatg aagatcactg    9060
gttcagtaga gagaattcac tcagtggagt ggaaggagaa ggactccaca aacttggata    9120
```

-continued

| | |
|---|---|
| catactcaga gacatatcaa ggattccagg ggggaacatg tatgcagatg acacagccgg | 9180 |
| atgggacaca agaataacag aggatgatct ccagaatgag gctaaaatca ctgacatcat | 9240 |
| ggagcccgaa catgccctgc tggctacgtc aatctttaag ctgacctacc aaaataaggt | 9300 |
| ggtaagggtg cagagaccag caaaaaatgg aaccgtgatg gatgttatat ccagacgtga | 9360 |
| ccagagaggc agtggacagg ttggaactta tggcttaaac actttcacca acatggaggc | 9420 |
| ccaactgata agacaaatgg agtccgaggg aatcttttta cccagcgaat ggaaaccccc | 9480 |
| aaatctagcc ggaagagttc tcgactggtt ggaaaaatat ggtgtcgaaa ggctgaaaag | 9540 |
| aatggcaatc agcggagatg actgtgtggt gaaaccaatt gatgacaggt tcgcaacagc | 9600 |
| cttaacagct ttgaatgaca tgggaaaagt aagaaaagac ataccacaat gggaaccttc | 9660 |
| aaaaggatgg aatgattggc aacaagtgcc tttctgttca caccacttcc accagctaat | 9720 |
| tatgaaggat gggagggaga tagtggtgcc atgccgcaac caagatgaac ttgtggggag | 9780 |
| ggccagagta tcacaaggcg ccggatggag cctgagagaa accgcatgcc taggcaagtc | 9840 |
| atatgcacaa atgtggcagc tgatgtattt ccacaggaga gacctgagac tggcggctaa | 9900 |
| cgctatttgt tcagccgttc cagttgattg ggtcccaacc agccgcacca cctggtcgat | 9960 |
| ccatgcccat caccaatgga tgacaacaga agacatgtta tcagtatgga ataggtctg | 10020 |
| gatagaggaa aacccatgga tggaggataa gactcatgtg tccagttggg aagaagttcc | 10080 |
| atacctagga aagagggaag atcagtggtg tggatccctg ataggcttaa cagcaagggc | 10140 |
| cacctgggcc actaatatac aagtggccat aaaccaagtg agaaggctca ttgggaatga | 10200 |
| gaattatcta gattacatga catcaatgaa gagattcaag aatgagagtg atcccgaagg | 10260 |
| ggcactctgg taagtcaaca cattcacaaa ataaaggaaa ataaaaaatc aaatgaggca | 10320 |
| agaagtcagg ccagattaag ccatagtacg gtaagagcta tgctgcctgt gagccccgtc | 10380 |
| caaggacgta aaatgaagtc aggccgaaag ccacggtttg agcaagccgt gctgcctgtg | 10440 |
| gctccatcgt ggggatgtaa aaacccggga ggctgcaacc catggaagct gtacgcatgg | 10500 |
| ggtagcagac tagtggttag aggagacccc tcccaagaca caacgcagca gcggggccca | 10560 |
| acaccagggg aagctgtacc ctggtggtaa ggactagagg ttagaggaga ccccccgcgt | 10620 |
| aacaataaac agcatattga cgctgggaga ccagagat cctgctgtct ctacagcatc | 10680 |
| attccaggca cagaacgcca gaaaatggaa tggtgctgtt gaatcaacag gttct | 10735 |

<210> SEQ ID NO 3
<211> LENGTH: 10735
<212> TYPE: DNA
<213> ORGANISM: Dengue virus
<220> FEATURE:
<221> NAME/KEY: misc_feature
<222> LOCATION: (1)..(10735)
<223> OTHER INFORMATION: LAV-1
    Dengue virus type 1 strain 16007 (PDK-13) polyprotein precursor,
    complete cds

<400> SEQUENCE: 3

| | |
|---|---|
| agttgttagt ctacgtggac cgacaagaac agtttcgaat cggaagcttg cttaacgtag | 60 |
| ttctaacagt ttttttattag agagcagatc tctgatgatc aaccaacgaa aaaagacggg | 120 |
| tcgaccgtct ttcaatatgc tgaaacgcgc gagaaaccgc gtgtcaactg tttcacagtt | 180 |
| ggcgaagaga ttctcaaaag gattgctctc aggccaagga cccatgaaat tggtgatggc | 240 |
| tttcatagca ttcttaagat ttctagccat accccccaaca gcaggaattt tggctagatg | 300 |

```
gggctcattc aagaagaatg gagcgattaa agtgttacgg ggtttcaaga gagaaatctc    360
aaacatgcta acataatga acaggaggaa aagatccgtg accatgctcc ttatgctgct    420
gcccacagcc ctggcgttcc atctgacgac acgaggggga gagccgcata tgatagttag    480
caagcaggaa agaggaaagt cacttttgtt caagacctct gcaggtgtca acatgtgcac    540
cctcattgcg atggatttgg gagagttgtg tgaggacacg atgacctaca aatgcccccg    600
gatcactgag gcggaaccag atgacgttga ctgttggtgc aatgccacgg acacatgggt    660
gacctatgga acgtgctctc aaactggcga acaccgacga gacaaacgtt ccgtcgcatt    720
ggccccacac gtggggcttg gcctagaaac aagagccgaa acgtggatgt cctctgaagg    780
tgcttggaaa cagatacaaa agtagagac ttgggctctg agacatccag gattcacggt    840
gatagccctt tttctagcac atgccatagg aacatccatc acccagaaag ggatcatttt    900 catttgctg atgctggtaa caccatctat ggccatgcga tgcgtgggaa taggcaacag    960
agacttcgtg gaaggactgt caggagcaac atgggtggat gtggtactgg agcatggaag   1020
ttgcgtcacc accatggcaa aaacaaacc aacactggac attgaactct gaagacgga    1080 ggtcacaaac cctgcagttc tgcgtaaatt gtgcattgaa gctaaaatat caaacaccac   1140
caccgattcg agatgtccaa cacaaggaga agccacactg gtggaagaac aagacgcgaa   1200
ctttgtgtgc cgacgaacgt tcgtggacag aggctggggc aatggctgtg ggctattcgg   1260
aaaaggtagt ctaataacgt gtgccaagtt taagtgtgtg acaaaactag aaggaaagat   1320
agctcaatat gaaaacctaa atattcagt gatagtcacc gtccacactg gagatcagca   1380
ccaggtggga aatgagacta cagaacatgg aacaactgca accataacac ctcaagctcc   1440
tacgtcggaa atacagctga ccgactacgg aaccttaca ttagattgtt cacctaggac   1500
agggctagat tttaacgaga tggtgttgct gacaatgaaa aagaaatcat ggcttgtcca   1560
caaacagtgg tttctagact accactgcc ttggacctct ggggctttaa catcccaaga   1620
gacttggaac agacaagatt tactggtcac atttaagaca gctcatgcaa agaagcagga   1680
agtagtcgta ctaggatcac aagaaggagc aatgcacact gcgctgactg gagcgacaga   1740
aatccaaacg tcaggaacga caacaatttt cgcaggacac ctaaaatgca gactaaaaat   1800
ggacaaacta actttaaaag ggatgtcata tgtgatgtgc acaggctcat tcaagttaga   1860
gaaagaagtg gctgagaccc agcatggaac tgttctggtg caggttaaat atgaaggaac   1920
agacgcacca tgcaagattc ccttttcgac ccaagatgag aaaggagcaa cccagaatgg   1980
gagattaata acagccaacc ccatagtcac tgacaaagaa aaaccagtca atattgaggc   2040
agaaccaccc tttggtgaga gctacatcgt ggtaggagca ggtgaaaaag ctttgaaact   2100
aagctggttc aagaaggaa gcagcatagg gaaaatgttt gaagcaactg cccgaggagc   2160
acgaaggatg gccattctgg agacaccgc atgggacttc ggttctatag gagagtgtt    2220 cacgtctatg ggaaaactgg tacaccaggt ttttggaact gcatatggag ttttgttttag   2280 cggagtttct tggaccatga aaataggaat agggattctg ctgacatggc taggattaaa   2340
ttcaaggaac acgtccctt cggtgatgtg catcgcagtt ggcatggtca cactgtacct   2400
aggagtcatg gttcaggcag attcgggatg tgtaatcaac tggaaaggca gagaacttaa   2460
atgtggaagc ggcattttg tcactaatga agttcacact tggacagagc aatacaaatt   2520
ccaggctgac tcccccaaga gactatcagc agccattggg aaggcatggg aggagggtgt   2580
gtgtggaatc cgatcagcca ctcgtctcga aacatcatg tggaaacaaa tatcaaatga   2640
attgaaccac atcctacttg aaaatgacat gaaatttaca gtggtcgtgg gagacgttag   2700
```

```
tggaatcttg gcccaaggga aaaaaatgat taggccacaa cccatggaac acaaatactc   2760
gtggaaaagc tggggaaaag ctaaaatcat aggagcggat gtacagaaca ccaccttcat   2820
catcgacggc ccaaacaccc cagaatgccc tgacaatcaa agagcatgga atatttggga   2880
agtagaggac tatggatttg ggattttcac gacaaacata tggttgaaat tgcgtgactc   2940
ctacacccaa gtatgtgacc accggctgat gtcagctgcc attaaggaca gcaaggcagt   3000
ccatgctgac atggggtact ggatagaaag tgaaaagaac gagacatgga agttggcgag   3060
agcctccttt atagaagtta agacatgcat ctggccaaaa tcccacactc tatggagcaa   3120
tggagttctg gaaagtgaaa tgataattcc aaagatatat ggaggaccaa tatctcagca   3180
caactacaga ccaggatatt tcacacaaac agcagggccg tggcacctag caagttgga    3240 actagatttc gattttgtg aaggtaccac agttgttgtg gatgaacatt gtggaaatcg   3300
aggaccatct ctcagaacca acagtcac aggaaagata atccatgaat ggtgctgcag   3360
atcttgtacg ctaccccccc tacgtttcaa aggggaagac gggtgttggt acggcatgga   3420
aatcagacca gtgaaggaca aggaagagaa cctggtcaag tcaatggtct ctgcagggtc   3480
aggagaagtg gacagctttt cactaggact gctatgcata tcaataatga ttgaagaagt   3540
gatgagatcc agatggagca aaaaaatgct gatgactgga acactggctg tgttcctcct   3600
tcttataatg ggacaattga catggagtga tctgatcagg ttatgtatta tggttggagc   3660
caacgcttca gacaagatgg ggatgggaac aacgtaccta gctttaatgg ccactttcaa   3720
aatgagacca atgttcgccg tcgggctatt atttcgcaga ctaacatcta gagaagttct   3780
tcttcttaca attggcttga gcctggtggc atccgtggag ctaccaagtt ccctagagga   3840
gctgggggat ggacttgcaa taggcatcat gatgttgaaa ttattgactg attttcagtc   3900
acaccagcta tgggctactc tgctatcctt gacatttatt aaaacaactt tttcattgca   3960
ctatgcatgg aagacaatgg ctatggtact gtcaattgta tctctcttcc ctttatgcct   4020
gtccacgacc tctcaaaaaa caacatggct tccggtgctg ttgggatctc ttggatgcaa   4080
accactaccc atgtttctta acagaaaaa caaaatctgg ggaaggaaga gttggccct    4140 caatgaagga attatggctg ttggaatagt tagtattcta ctaagttcac ttttaaaaaa   4200
tgatgtgccg ctagccggcc cattaatagc tggaggcatg ctaatagcat gttatgtcat   4260
atccggaagc tcagctgatt tatcactgga gaaagcggct gaggtctcct gggaggaaga   4320
agcagaacac tcaggcgcct cacacaacat actagtagag gttcaagatg atggaaccat   4380
gaagataaaa gatgaagaga gagatgacac gctcaccatt ctccttaaag caactctgct   4440
ggcagtctca ggggtgtacc caatgtcaat accagcgacc cttttgtgt ggtatttttg   4500 gcagaaaaag aaacagagat caggagtgct atgggacaca cccagccccc cagaagtgga   4560
aagagcagtt cttgatgatg gcatctatag aattttgcaa agaggactgt gggcaggtc    4620 ccaagtagga gtaggagttt tccaagaagg cgtgttccac acaatgtggc acgtcactag   4680
gggagctgtc ctcatgtatc aaggaaaaag gctggaacca agctgggcca gtgtcaaaaa   4740
agacttgatc tcatatggag gaggttggag gtttcaagga tcctggaaca cgggagaaga   4800
agtacaggtg attgctgttg aaccgggaaa aaaccccaaa aatgtacaaa caacgccggg   4860
taccttcaag accctgaag gcgaagttgg agccatagcc ttagacttta aacctggcac   4920
atctggatct cccatcgtaa acagagaggg aaaaatagta ggtctttatg gaaatggagt   4980
ggtgacaaca agcggaactt acgttagtgc catagctcaa gctaaggcat cacaagaagg   5040
```

```
gcctctacca gagattgagg acaaggtgtt taggaaaaga aacttaacaa taatggacct    5100
acatccagga tcgggaaaaa caagaagata ccttccagcc atagtccgtg aggccataaa    5160
aaggaagctg cgcacgctaa tcctagctcc cacaagagtt gtcgcttctg aaatggcaga    5220
ggcactcaag ggagtgccaa taaggtatca gacaacagca gtgaagagtg aacacacagg    5280
aaaggagata gttgacctta tgtgccacgc cactttcacc atgcgcctcc tgtctcccgt    5340
gagagttccc aattataaca tgattatcat ggatgaagca cacttcaccg atccagccag    5400
catagcagcc agagggtaca tctcaacccg agtgggtatg ggtgaagcag ctgcgatctt    5460
tatgacagcc actcccccag gatcggtgga ggccttttcca cagagcaatg caattatcca    5520
agatgaggaa agagacattc ctgagagatc atggaactca ggctatgact ggatcactga    5580 tttttccaggt aaacagtct ggtttgttcc aagcatcaaa tcaggaaatg acattgccaa    5640
ctgtttaaga aaaacgggaa acgggtgat ccaattgagc agaaaaacct ttgacactga    5700
gtaccagaaa acaaaaaaca acgactggga ctatgtcgtc acaacagaca tttccgaaat    5760
gggagcaaat ttccgggccg acagggtaat agacccaagg cggtgtctga aaccggtaat    5820
actaaaagat ggtccagagc gcgtcattct agccggaccg atgccagtga ctgtggccag    5880
tgccgcccag aggagaggaa gaattggaag gaaccaaaac aaggaaggtg atcagtatat    5940
ttacatggga cagcctttaa acaatgatga ggaccacgct cattggacag aagcaaagat    6000
gctccttgac aatataaaca caccagaagg gattatccca gccctctttg agccggagag    6060
agaaaagagt gcagctatag acggggaata cagactgcgg ggtgaagcaa ggaaaacgtt    6120
cgtggagctc atgagaagag gggatctacc agtctggcta tcctacaaag ttgcctcaga    6180
aggcttccag tactccgaca aaggtggtg cttcgatggg gaaaggaaca accaggtgtt    6240
ggaggagaac atggacgtgg agatctggac aaaagaagga gaaagaaaga aactacgacc    6300
tcgctggttg gacgccagaa catactctga cccactggct ctgcgcgagt taaagagtt    6360 tgcagcagga agaagaagcg tctcaggtga cctaatatta gaaatagggga aacttccaca    6420 acatttgacg caaagggccc agaatgcttt ggacaacttg gtcatgttgc acaattccga    6480
acaaggagga aaagcctata gacatgctat ggaagaactg ccagacacaa tagaaacgtt    6540
gatgctccta gccttgatag ctgtgttgac tggtggagtg acgctgttct tcctatcagg    6600
aagaggtcta ggaaaaacat ctatcggctt actctgcgtg atggcctcaa gcgcactgtt    6660
atggatggcc agtgtggagc cccattggat agcggcctcc atcatactgg agttctttct    6720
gatggtactg cttattccag agccagacag acagcgcact ccacaggaca accagctagc    6780
atatgtggtg ataggtctgt tattcgtgat attgacagtg gcagccaatg agatgggatt    6840
attggaaacc acaaagaaag acctggggat tggccatgta gctgctgaaa accaccacca    6900
tgctacaatg ctggacgtag acctacatcc agcttcagcc tggaccctct atgcagtggc    6960
cacaacaatc atcactccta tgatgagaca cacaattgaa aacacaacgg caaatatttc    7020
cctgacagcc atcgcaaacc aagcagctat attgatggga cttgacaagg gatggccaat    7080
atcgaagatg gacatagagg ttccactttct cgccttgggg tgctattccc aagtgaatcc    7140
gctgacactg atagcggcag tattgatgct agtagctcat tacgccataa ttggacctgg    7200
actgcaagca aaagctacta gagaagctca aaaagaaca gcggctggaa taatgaaaaa    7260
tccaactgtc gacgggattg ttgcaataga cttagatccc gtggtttacg atgcaaaatt    7320
tgaaaaacag ctaggccaaa taatgttgtt gatactttgc acatcacaga ttctttttgat    7380 gcggactaca tgggcccttgt gtgaatccat cacattggct actggaccct ctgaccactct    7440
```

```
ttgggaggga tctccaggaa aattctggaa caccacaata gcggtatcca tggcaaacat   7500
tttcaggggg agttatctag caggagcagg tctggccttc tcattaatga aatctctagg   7560
aggaggtagg agaggcacgg gagcccaagg ggaaacactg ggagaaaaat ggaaaagaca   7620
actaaaccaa ctgagcaagt cagaattcaa tacttacaag aggagtggga ttatggaggt   7680
ggatagatcc gaagccaaag agggactgaa agaggagaa acaaccaaac acgcagtatc   7740
gagaggaacg gccaaactga ggtggttcgt ggagaggaac cttgtgaaac cagaagggaa   7800
agtcatagac ctcggttgtg gaagaggtgg ctggtcatat tattgcgctg ggctgaagaa   7860
agtcacagaa gtgaaaggat acacaaaagg aggacctgga catgaggaac caatcccaat   7920
ggcgacctat ggatggaacc tagtaaagct gcactccgga aaagatgtat tttttatacc   7980
acctgagaaa tgtgacaccc ttttgtgtga tattggtgag tcctctccga acccaactat   8040
agaggaagga agaacgttac gtgttctgaa aatggtggaa ccatggctca gaggaaacca   8100
attttgcata aaaattctaa atccctatat gccgagcgtg gtagaaactc tggaacaaat   8160
gcaaagaaaa catggaggaa tgctagtgcg aaacccactc tcaagaaatt ccacccatga   8220
aatgtactgg gtttcatgtg gaacaggaaa cattgtgtca gcagtaaaca tgacatctag   8280
aatgttgcta aatcggttca caatggctca caggaagcca acatatgaaa gagacgtgga   8340
cttaggcgct ggaacaagac atgtggcagt agaaccagag gtagccaacc tagatatcat   8400
tggccagagg atagagaata taaaaaatga acataagtca acatggcatt atgatgagga   8460
caatccatac aaaacatggg cctatcatgg atcatatgag gttaagccat caggatcggc   8520
ctcatccatg gtcaatggcg tggtgagatt gctcaccaaa ccatgggatg ttatccccat   8580
ggtcacacaa atagccatga ctgataccac acccttggga caacagaggg tgtttaaaga   8640
gaaagttgac acgcgcacac caaaagcaaa acgtggcaca gcacaaatta tggaagtgac   8700
agccaggtgg ttatggggtt tccttttctag aaacaaaaaa cccagaattt gcacaagaga   8760
ggagtttaca agaaaagtta ggtcaaacgc agctattgga gcagtgttcg ttgatgaaaa   8820
tcaatggaac tcggcaaaag aagcagtgga agacgaacgg ttctgggaac ttgtccacag   8880
agagagggag cttcataaac aggggaaatg tgccacgtgt gtctacaata tgatggggaa   8940
gagagagaaa aaattaggag agttcggaaa ggcaaaagga agtcgtgcaa tatggtacat   9000
gtggttggga gcacgcttcc tagagtttga agcccttggt ttcatgaatg aagatcactg   9060
gttcagtaga gagaattcac tcagtggagt ggaaggagaa ggactccaca acttggata   9120 catactcaga gacatatcaa ggattccagg ggggaacatg tatgcagatg acacagccgg   9180
atgggacaca gaataacag aggatgatct ccagaatgag gctaaaatca ctgacatcat   9240
ggagcccgaa catgccctgc tggctacgtc aatctttaag ctgacctacc aaataaggt   9300 ggtaagggtg cagagaccag caaaaaatgg aaccgtgatg gatgttatat ccagacgtga   9360
ccagagaggc agtggacagg ttggaactta tggcttaaac actttcacca acatggaggc   9420
ccaactgata agacaaatgg agtctgaggg aatcttttta cccagcgaat ggaaacccc   9480 aaatctagcc ggaagagttc tcgactggtt ggaaaaatat ggtgtcgaaa ggctgaaaag   9540
aatggcaatc agcggagatg actgtgtggt gaaaccaatt gatgacaggt tcgcaacagc   9600
cttaacagct ttgaatgaca tgggaaaagt aagaaaagac ataccacaat gggaaccttc   9660
aaaaggatgg aatgattggc aacaagtgcc tttctgttca caccacttcc accagctaat   9720
tatgaaggat gggagggaga tagtggtgcc atgccgcaac aagatgaac ttgtggggag   9780
```

| | |
|---|---|
| ggccagagta tcacaaggcg ccggatggag cctgagagaa accgcatgcc taggcaagtc | 9840 |
| atatgcacaa atgtggcagc tgatgtattt ccacaggaga gacctgagac tggcggctaa | 9900 |
| cgctatttgt tcagccgttc cagttgattg ggtcccaacc agccgcacca cctggtcgat | 9960 |
| ccatgcccat caccaatgga tgacaacaga agacatgtta tcagtatgga atagggtctg | 10020 |
| gatagaggaa aacccatgga tggaggataa gactcatgtg tccagttggg aagaagttcc | 10080 |
| atacctagga agagggaag atcagtggtg tggatccctg ataggcttaa cagcaagggc | 10140 |
| cacctgggcc actaatatac aagtggccat aaaccaagtg agaaggctca ttgggaatga | 10200 |
| gaattatcta gattacatga catcaatgaa gagattcaag aatgagagtg atcccgaagg | 10260 |
| ggcactctgg taagtcaaca cattcacaaa ataaggaaa ataaaaaatc aaatgaggca | 10320 |
| agaagtcagg ccagattaag ccatagtacg gtaagagcta tgctgcctgt gagccccgtc | 10380 |
| caaggacgta aaatgaagtc aggccgaaag ccacggtttg agcaagccgt gctgcctgtg | 10440 |
| gctccatcgt ggggatgtaa aaacccggga ggctgcaacc catggaagct gtacgcatgg | 10500 |
| ggtagcagac tagtggttag aggagacccc tcccaagaca caacgcagca gcgggcccca | 10560 |
| acaccagggg aagctgtacc ctggtggtaa ggactagagg ttagaggaga cccccgcgt | 10620 |
| aacaataaac agcatattga cgctgggaga gaccagagat cctgctgtct ctacagcatc | 10680 |
| attccaggca cagaacgcca gaaaatggaa tggtgctgtt gaatcaacag gttct | 10735 |

<210> SEQ ID NO 4
<211> LENGTH: 38
<212> TYPE: DNA
<213> ORGANISM: Artificial Sequence
<220> FEATURE:
<223> OTHER INFORMATION: primer

<400> SEQUENCE: 4
gttttcccag tcacgactac gtggaccgac aagaacag                          38

<210> SEQ ID NO 5
<211> LENGTH: 37
<212> TYPE: DNA
<213> ORGANISM: Artificial sequence
<220> FEATURE:
<223> OTHER INFORMATION: primer

<400> SEQUENCE: 5
aacagctatg accatgggat ggagttacca gcatcag                           37

<210> SEQ ID NO 6
<211> LENGTH: 37
<212> TYPE: DNA
<213> ORGANISM: Artificial sequence
<220> FEATURE:
<223> OTHER INFORMATION: primer

<400> SEQUENCE: 6
gttttcccag tcacgactga acaccgacga gacaaac                           37

<210> SEQ ID NO 7
<211> LENGTH: 36
<212> TYPE: DNA
<213> ORGANISM: Artificial sequence
<220> FEATURE:
<223> OTHER INFORMATION: primer

<400> SEQUENCE: 7
aacagctatg accatgaggt ccaaggcagt ggtaag                            36

<210> SEQ ID NO 8
<211> LENGTH: 38
<212> TYPE: DNA
<213> ORGANISM: Artificial sequence
<220> FEATURE:
<223> OTHER INFORMATION: primer

<400> SEQUENCE: 8
gttttcccag tcacgacttg gaaatgagac cacagaac                        38

<210> SEQ ID NO 9
<211> LENGTH: 36
<212> TYPE: DNA
<213> ORGANISM: Artificial sequence
<220> FEATURE:
<223> OTHER INFORMATION: primer

<400> SEQUENCE: 9
aacagctatg accatggaaa caccgctgaa caaaac                          36

<210> SEQ ID NO 10
<211> LENGTH: 36
<212> TYPE: DNA
<213> ORGANISM: Artificial sequence
<220> FEATURE:
<223> OTHER INFORMATION: primer

<400> SEQUENCE: 10
gttttcccag tcacgacggt tcaagaaggg aagcag                          36

<210> SEQ ID NO 11
<211> LENGTH: 37
<212> TYPE: DNA
<213> ORGANISM: Artificial sequence
<220> FEATURE:
<223> OTHER INFORMATION: primer

<400> SEQUENCE: 11
aacagctatg accatgttct atccagtacc ccatgtc                         37

<210> SEQ ID NO 12
<211> LENGTH: 39
<212> TYPE: DNA
<213> ORGANISM: Artificial sequence
<220> FEATURE:
<223> OTHER INFORMATION: primer

<400> SEQUENCE: 12
gttttcccag tcacgaccag aataccacct tcatcatcg                       39

<210> SEQ ID NO 13
<211> LENGTH: 35
<212> TYPE: DNA
<213> ORGANISM: Artificial sequence
<220> FEATURE:
<223> OTHER INFORMATION: primer

<400> SEQUENCE: 13
aacagctatg accatgttcc catccccatc ttgtc                           35

<210> SEQ ID NO 14
<211> LENGTH: 39
<212> TYPE: DNA
<213> ORGANISM: Artificial sequence
<220> FEATURE:

<223> OTHER INFORMATION: primer

<400> SEQUENCE: 14
gttttcccag tcacgacgga aatcagacca gtcaaggag                     39

<210> SEQ ID NO 15
<211> LENGTH: 36
<212> TYPE: DNA
<213> ORGANISM: Artificial sequence
<220> FEATURE:
<223> OTHER INFORMATION: primer

<400> SEQUENCE: 15
aacagctatg accatgtgtt gtgtgaggca ccagag                       36

<210> SEQ ID NO 16
<211> LENGTH: 38
<212> TYPE: DNA
<213> ORGANISM: Artificial sequence
<220> FEATURE:
<223> OTHER INFORMATION: primer

<400> SEQUENCE: 16
gttttcccag tcacgacgca aaccactaac catgtttc                     38

<210> SEQ ID NO 17
<211> LENGTH: 35
<212> TYPE: DNA
<213> ORGANISM: Artificial sequence
<220> FEATURE:
<223> OTHER INFORMATION: primer

<400> SEQUENCE: 17
aacagctatg accatgccac ttgttgtcac cactc                        35

<210> SEQ ID NO 18
<211> LENGTH: 37
<212> TYPE: DNA
<213> ORGANISM: Artificial sequence
<220> FEATURE:
<223> OTHER INFORMATION: primer

<400> SEQUENCE: 18
gttttcccag tcacgaccca agggaagaga ctggaac                      37

<210> SEQ ID NO 19
<211> LENGTH: 37
<212> TYPE: DNA
<213> ORGANISM: Artificial sequence
<220> FEATURE:
<223> OTHER INFORMATION: primer

<400> SEQUENCE: 19
aacagctatg accatgtcct gatttgatgc ttggaac                      37

<210> SEQ ID NO 20
<211> LENGTH: 38
<212> TYPE: DNA
<213> ORGANISM: Artificial sequence
<220> FEATURE:
<223> OTHER INFORMATION: primer

<400> SEQUENCE: 20
gttttcccag tcacgacaag cacatttac cgatccag                      38

```
<210> SEQ ID NO 21
<211> LENGTH: 41
<212> TYPE: DNA
<213> ORGANISM: Artificial sequence
<220> FEATURE:
<223> OTHER INFORMATION: primer

<400> SEQUENCE: 21
aacagctatg accatggtcg tagtttcttt ctttctcctt c                        41

<210> SEQ ID NO 22
<211> LENGTH: 37
<212> TYPE: DNA
<213> ORGANISM: Artificial sequence
<220> FEATURE:
<223> OTHER INFORMATION: primer

<400> SEQUENCE: 22
gttttcccag tcacgacgca atagacgggg aatacag                              37

<210> SEQ ID NO 23
<211> LENGTH: 36
<212> TYPE: DNA
<213> ORGANISM: Artificial sequence
<220> FEATURE:
<223> OTHER INFORMATION: primer

<400> SEQUENCE: 23
aacagctatg accatgatga tggtggtttt cagcag                               36

<210> SEQ ID NO 24
<211> LENGTH: 37
<212> TYPE: DNA
<213> ORGANISM: Artificial sequence
<220> FEATURE:
<223> OTHER INFORMATION: primer

<400> SEQUENCE: 24
gttttcccag tcacgacgtg ttgcttattc cagagcc                              37

<210> SEQ ID NO 25
<211> LENGTH: 38
<212> TYPE: DNA
<213> ORGANISM: Artificial sequence
<220> FEATURE:
<223> OTHER INFORMATION: primer

<400> SEQUENCE: 25
aacagctatg accatggctg tcttttccat ttttctcc                             38

<210> SEQ ID NO 26
<211> LENGTH: 37
<212> TYPE: DNA
<213> ORGANISM: Artificial sequence
<220> FEATURE:
<223> OTHER INFORMATION: primer

<400> SEQUENCE: 26
gttttcccag tcacgacact ttgcacatca cagatcc                              37

<210> SEQ ID NO 27
<211> LENGTH: 35
<212> TYPE: DNA
<213> ORGANISM: Artificial sequence
<220> FEATURE:
<223> OTHER INFORMATION: primer
```

```
<400> SEQUENCE: 27
aacagctatg accatgttcg cactagcatt cctcc                          35

<210> SEQ ID NO 28
<211> LENGTH: 37
<212> TYPE: DNA
<213> ORGANISM: Artificial sequence
<220> FEATURE:
<223> OTHER INFORMATION: primer

<400> SEQUENCE: 28
gttttcccag tcacgaccac ctgagaaatg tgacacc                        37

<210> SEQ ID NO 29
<211> LENGTH: 38
<212> TYPE: DNA
<213> ORGANISM: Artificial sequence
<220> FEATURE:
<223> OTHER INFORMATION: primer

<400> SEQUENCE: 29
aacagctatg accatgtttc cttgtttatg aagctccc                       38

<210> SEQ ID NO 30
<211> LENGTH: 36
<212> TYPE: DNA
<213> ORGANISM: Artificial sequence
<220> FEATURE:
<223> OTHER INFORMATION: primer

<400> SEQUENCE: 30
gttttcccag tcacgaccaa aagcgaaacg aggcac                         36

<210> SEQ ID NO 31
<211> LENGTH: 38
<212> TYPE: DNA
<213> ORGANISM: Artificial sequence
<220> FEATURE:
<223> OTHER INFORMATION: primer

<400> SEQUENCE: 31
aacagctatg accatggttt caccacacag tcatctcc                       38

<210> SEQ ID NO 32
<211> LENGTH: 37
<212> TYPE: DNA
<213> ORGANISM: Artificial sequence
<220> FEATURE:
<223> OTHER INFORMATION: primer

<400> SEQUENCE: 32
gttttcccag tcacgacaga ccagcgaaaa atggaac                        37

<210> SEQ ID NO 33
<211> LENGTH: 35
<212> TYPE: DNA
<213> ORGANISM: Artificial sequence
<220> FEATURE:
<223> OTHER INFORMATION: primer

<400> SEQUENCE: 33
aacagctatg accatgtccc aatgagcctt ctcac                          35

<210> SEQ ID NO 34
<211> LENGTH: 38
```

```
<212> TYPE: DNA
<213> ORGANISM: Artificial sequence
<220> FEATURE:
<223> OTHER INFORMATION: primer

<400> SEQUENCE: 34
gttttcccag tcacgacgct aatgctatct gttcagcc                              38

<210> SEQ ID NO 35
<211> LENGTH: 36
<212> TYPE: DNA
<213> ORGANISM: Artificial sequence
<220> FEATURE:
<223> OTHER INFORMATION: primer

<400> SEQUENCE: 35
aacagctatg accatgtgat tcaacagcac cattcc                                36

<210> SEQ ID NO 36
<211> LENGTH: 17
<212> TYPE: DNA
<213> ORGANISM: Artificial sequence
<220> FEATURE:
<223> OTHER INFORMATION: primer

<400> SEQUENCE: 36
ccatggaagc tgtacgc                                                     17

<210> SEQ ID NO 37
<211> LENGTH: 19
<212> TYPE: DNA
<213> ORGANISM: Artificial sequence
<220> FEATURE:
<223> OTHER INFORMATION: primer

<400> SEQUENCE: 37
gagacagcag gatctctgg                                                   19

<210> SEQ ID NO 38
<211> LENGTH: 17
<212> TYPE: DNA
<213> ORGANISM: Artificial sequence
<220> FEATURE:
<223> OTHER INFORMATION: primer tail

<400> SEQUENCE: 38
gttttcccag tcacgac                                                     17

<210> SEQ ID NO 39
<211> LENGTH: 16
<212> TYPE: DNA
<213> ORGANISM: Artificial sequence
<220> FEATURE:
<223> OTHER INFORMATION: primer tail

<400> SEQUENCE: 39
aacagctatg accatg                                                      16

<210> SEQ ID NO 40
<211> LENGTH: 10723
<212> TYPE: DNA
<213> ORGANISM: Dengue virus
<220> FEATURE:
<221> NAME/KEY: misc_feature
<222> LOCATION: (1)..(10723)
<223> OTHER INFOR
<221> NAME/KEY: misc_feature
<222> LOCATION: (10361)..(10361)
<223> OTHER INFORMATION: n=A or T or G or C

<400> SEQUENCE: 40

| | | | | | | |
|---|---|---|---|---|---|---|
| agttgttagt | ctacgtggac | cgacaaagac | agattctttg | agggagctaa | gctcaatgta | 60 |
| gttctaacag | ttttttaatt | agagagcaga | tctctgatga | ataaccaacg | gaaaaaggcg | 120 |
| aaaaacacgc | ctttcaatat | gctgaaacgc | gagagaaacc | gcgtgtcgac | tgtgcaacag | 180 |
| ctgacaaaga | gattctcact | tggaatgctg | cagggacgag | gaccattaaa | actgttcatg | 240 |
| gccctggtgg | cgttccttcg | tttcctaaca | atcccaccaa | cagcagggat | attgaagaga | 300 |
| tggggaacaa | ttaaaaaatc | aaaagctatt | aatgttttga | gagggttcag | gaaagagatt | 360 |
| ggaaggatgc | tgaacatctt | gaataggaga | cgcagatctg | caggcatgat | cattatgctg | 420 |
| attccaacag | tgatggcgtt | ccatttaacc | acacgtaacg | gagaaccaca | catgatcgtc | 480 |
| agcagacaag | agaaagggaa | aagtcttctg | tttaaaacag | aggttggcgt | gaacatgtgt | 540 |
| accctcatgg | ccatggacct | tggtgaattg | tgtgaagaca | caatcacgta | caagtgtccc | 600 |
| cttctcaggc | agaatgagcc | agaagacata | gactgttggt | gcaactctac | gtccacgtgg | 660 |
| gtaacttatg | ggacgtgtac | caccatggga | gaacatagaa | gagaaaaaag | atcagtggca | 720 |
| ctcgttccac | atgtgcgaat | gggactggag | acacgaactg | aaacatggat | gtcatcagaa | 780 |
| ggggcctgga | aacatgtcca | gagaattgaa | acttggatct | tgagacatcc | aggcttcacc | 840 |
| atgatggcag | caatcctggc | ataccaccata | ggaacgacac | atttccaaag | agccctgatt | 900 |
| ttcatcttac | tgacagctgt | cactccttca | atgacaatgc | gttgcatagg | aatgtcaaat | 960 |
| agagactttg | tggaagggt | ttcaggagga | agctgggttg | acatagtctt | agaacatgga | 1020 |
| agctgtgtga | cgacgatggc | aaaaaacaaa | ccaacattgg | attttgaact | gataaaaaca | 1080 |
| gaagccaaac | agcctgccac | cctaaggaag | tactgtatag | aggcaaagct | aaccaacaca | 1140 |
| acaacagaat | ctcgctgccc | aacacaaggg | gaacccagcc | taaatgaaga | gcaggacaaa | 1200 |
| aggttcgtct | gcaaacactc | catggtagac | agaggatggg | gaaatggatg | tggactattt | 1260 |
| ggaaagggag | gcattgtgac | ctgtgctatg | ttcagatgca | aaaagaacat | ggaaggaaaa | 1320 |
| gttgtgcaac | cagaaaactt | ggaatacacc | attgtgataa | cacctcactc | aggggaagag | 1380 |
| catgcagtcg | gaaatgacac | aggaaaacat | ggcaaggaaa | tcaaaataac | accacagagt | 1440 |
| tccatcacag | aagcagaatt | gacaggttat | ggcactgtca | caatggagtg | ctctccaaga | 1500 |
| acgggcctcg | acttcaatga | gatggtgttg | ctgcagatgg | aaaataaagc | ttggctggtg | 1560 |
| cacaggcaat | ggttcctaga | cctgccgtta | ccatggttgc | ccggagcgga | cacacaagag | 1620 |
| tcaaattgga | tacagaagga | gacattggtc | actttcaaaa | atccccatgc | gaagaaacag | 1680 |
| gatgttgttg | ttttaggatc | ccaagaaggg | gccatgcaca | cagcacttac | aggggccaca | 1740 |
| gaaatccaaa | tgtcatcagg | aaacttactc | ttcacaggac | atctcaagtg | caggctgaga | 1800 |
| atggacaagc | tacagctcaa | aggaatgtca | tactctatgt | gcacaggaaa | gtttaaagtt | 1860 |
| gtgaaggaaa | tagcagaaac | acaacatgga | acaatagtta | tcagagtgca | atatgaaggg | 1920 |
| gacggctctc | catgcaagat | cccttttgag | ataatggatt | tggaaaaaag | acatgtctta | 1980 |
| ggtcgcctga | ttacagtcaa | cccaattgtg | acagaaaaag | atagcccagt | caacatagaa | 2040 |
| gcagaacctc | catttggaga | cagctacatc | atcataggag | tagagccggg | acaactgaag | 2100 |
| ctcaactggt | ttaagaaagg | aagttctatc | ggccaaatgt | ttgagacaac | aatgaggggg | 2160 |
| gcgaagagaa | tggccatttt | aggtgacaca | gcctgggatt | ttggatcctt | gggaggagtg | 2220 |

```
tttacatcta taggaaaggc tctccaccaa gtctttggag caatctatgg agctgccttc    2280
agtggggttt catggactat gaaaatcctc ataggagtca ttatcacatg ataggaatg    2340 aattcacgca gcacctcact gtctgtgaca ctagtattgg tgggaattgt gacactgtat    2400
ttgggagtca tggtgcaggc cgatagtggt tgcgttgtga gctggaaaaa caagaactg    2460 aaatgtggca gtgggatttt catcacagac aacgtgcaca catggacaga acaatacaaa    2520
ttccaaccag aatccccttc aaaactagct tcagctatcc agaaagccca tgaagaggac    2580
atttgtggaa tccgctcagt aacaagactg gagaatctga tgtggaaaca ataacacca    2640 gaattgaatc acattctatc agaaaatgag gtgaagttaa ctattatgac aggagacatc    2700
aaaggaatca tgcaggcagg aaaacgatct ctgcggcctc agcccactga gctgaagtat    2760
tcatggaaaa catggggcaa agcaaaaatg ctctctacag agtctcataa ccagaccttt    2820
ctcattgatg cccccgaaac agcagaatgc cccaacacaa atagagcttg gaattcgttg    2880
gaagttgaag actatggctt tggagtattc accaccaata tatggctaaa attgaaagaa    2940
aaacaggatg tattctgcga ctcaaaactc atgtcagcgg ccataaaaga caacagagcc    3000
gtccatgccg atatgggtta ttggatagaa agtgcactca atgacacatg gaagatagag    3060
aaagcctctt tcattgaagt taaaaactgc cactggccaa atcacacac cctctggagc    3120 aatggagtgc tagaaagtga gatgataatt ccaagaatc tcgctggacc agtgtctcaa    3180
cacaactata gaccaggcta ccatacacaa ataacaggac catggcatct aggtaagctt    3240
gagatggact ttgatttctg tgatggaaca acagtggtag tgactgagga ctgcggaaat    3300
agaggaccct ctttgagaac aaccactgcc tctggaaaac tcataacaga atggtgctgc    3360
cgatcttgca cattccacc gctaagatac agaggtgagg atgggtgctg gtacgggatg    3420
gaaatcagac cattgaagga gaagaagag aatttggtca actccttggt cacagctgga    3480
catgggcagg tcgacaactt ttcactagga gtcttgggaa tggcattgtt cctggaggaa    3540
atgcttagga cccgagtagg aacgaaacat gcaatactac tagttgcagt ttcttttgtg    3600
acattgatca cagggaacat gtcctttaga gacctgggaa gagtgatggt tatggtaggc    3660
gccactatga cggatgacat aggtatgggc gtgacttatc ttgccctact agcagccttc    3720
aaagtcagac caacttttgc agctggacta ctcttgagaa agctgacctc aaggaattg    3780 atgatgacta ctataggaat tgtactcctc tcccagagca ccataccaga gaccattct    3840 gagttgactg atgcgttagc cttaggcatg atggtcctca aaatggtgag aaatatggaa    3900
aagtatcaat tggcagtgac tatcatggct atcttgtgcg tcccaaacgc agtgatatta    3960
caaaacgcat ggaaagtgag ttgcacaata ttggcagtgg tgtccgtttc cccactgttc    4020
ttaacatcct cacagcaaaa aacagattgg ataccattag cattgacgat caaaggtctc    4080
aatccaacag ctattttct aacaaccctc tcaagaacca gcaagaaaag gagctggcca    4140
ttaaatgagg ctatcatggc agtcgggatg gtgagcattt tagccagttc tctcctaaaa    4200
aatgatattc ccatgacagg accattagtg gctggagggc tcctcactgt gtgctacgtg    4260
ctcactggac gatcggccga tttggaactg gagagagcag ccgatgtcaa atgggaagac    4320
caggcagaga tatcaggaag cagtccaatc ctgtcaataa caatatcaga agatggtagc    4380
atgtcgataa aaaatgaaga ggaagaacaa acactgacca tactcattag aacaggattg    4440
ctggtgatct caggactttt tcctgtatca ataccaatca cggcagcagc atggtacctg    4500
tgggaagtga agaaacaacg ggccggagta ttgtgggatg ttccttcacc cccacccatg    4560
```

```
ggaaaggctg aactggaaga tggagcctat agaattaagc aaaaagggat tcttggatat    4620
tcccagatcg gagccggagt ttacaaagaa ggaacattcc atacaatgtg gcatgtcaca    4680
cgtggcgctg ttctaatgca taaaggaaag aggattgaac caacatgggc ggacgtcaag    4740
aaagacctaa tatcatatgg aggaggctgg aagttagaag gagaatggaa ggaaggagaa    4800
gaagtccagg tattggcact ggagcctgga aaaaatccaa gagccgtcca aacgaaacct    4860
ggtcttttca aaaccaacgc cggaacaata ggtgctgtat ctctggactt ttctcctgga    4920
acgtcaggat ctccaattat cgacaaaaaa ggaaagttg tgggtcttta tggtaatggt     4980
gttgttacaa ggagtggagc atatgtgagt gctatagccc agactgaaaa aagcattgaa    5040
gacaacccag agatcgaaga tcacattttc gaaagagaa gactgaccat catggacctc     5100
cacccaggag cgggaaagac gaagagatac cttccggcca tagtcagaga agctataaaa    5160
cggggtttga acattaat cttggccccc actagagttg tggcagctga aatggaggaa      5220
gcccttagag gacttccaat aagataccag accccagcca tcagagctga gcacaccggg    5280
cgggagattg tggacctaat gtgtcatgcc acatttacca tgaggctgct atcaccagtt    5340
agagtgccaa actacaacct gattatcatg gacgaagccc atttcacaga cccagcaagt    5400
atagcagcta gaggatacat ctcaactcga gtggagatgg gtgaggcagc tgggattttt    5460
atgacagcca ctcccccggg aagcagagac ccatttcctc agagcaatgc accaatcata    5520
gatgaagaaa gagaaatccc tgaacgctcg tggaattccg acatgaatgg ggtcacggat    5580
tttaaaggga agactgtttg gttcgttcca agtataaaag caggaaatga tatagcagct    5640
tgcctgagga aaatggaaa gaagtgataa caactcagta ggaagacctt tgattctgag     5700
tatgtcaaga ctagaaccaa tgattgggac ttcgtggtta caactgacat ttcagaaatg    5760
ggtgccaatt tcaaggctga gagggtttata gaccccagac gctgcatgaa ccagtcata    5820 ctaacagatg gtgaagagcg ggtgattctg gcaggaccta tgccagtgac ccactctagt    5880
gcagcacaaa aagagggag aataggaaga aatccaaaaa atgagaatga ccagtacata    5940
tacatggggg aacctctgga aaatgatgaa gactgtgcac actggaaaga agctaaaatg    6000
ctcctagata acatcaacac gccagaagga atcattccta gcatgttcga accagagcgt    6060
gaaaaggtgg atgccattga tggcgaatac cgcttgagag gagaagcaag gaaaaccttt    6120
gtagacttaa tgagaagagg agacctacca gtctggttgg cctacagagt ggcagctgaa    6180
ggcatcaact acgcagacag aaggtggtgt tttgatggag tcaagaacaa ccaaatccta    6240
gaagaaaacg tggaagttga aatctggaca aaagaagggg aaaggaagaa attgaaaccc    6300
agatggttgg atgctaggat ctattctgac ccactggcgc taaaagaatt taaggaattt    6360
gcagccggaa gaaagtctct gaccctgaac ctaatcacag aaatgggtag gctcccaacc    6420
ttcatgactc agaaggcaag agacgcactg gacaacttag cagtgctgca cacggctgag    6480
gcaggtggaa gggcgtacaa ccatgctctc agtgaactgc cggagaccct ggagacattg    6540
cttttactga cacttctggc tacagtcacg ggagggatct ttttattctt gatgagcgca    6600
aggggcatag ggaagatgac cctgggaatg tgctgcataa tcacggctag catcctccta    6660
tggtacgcac aaatacagcc acactggata gcagcttcaa taatactgga gttttttctc    6720
atagttttgc ttattccaga acctgaaaaa cagagaacac cccaagacaa ccaactgacc    6780
tacgttgtca tagccatcct cacagtggtg gccgcaacca tggcaaacga gatgggtttc    6840
ctagaaaaaa cgaagaaaga tctcggattg ggaagcattg caacccagca acccgagagc    6900
aacatcctgg acatagatct acgtcctgca tcagcatgga cgctgtatgc cgtggccaca    6960
```

```
acatttgtta caccaatgtt gagacatagc attgaaaatt cctcagtgaa tgtgtcccta    7020
acagctatag ccaaccaagc cacagtgtta atgggtctcg ggaaaggatg gccattgtca    7080
aagatggaca tcggagttcc ccttctcgcc attggatgct actcacaagt caaccccata    7140
actctcacag cagctctttt cttattggta gcacattatg ccatcatagg gccaggactc    7200
caagcaaaag caaccagaga agctcagaaa agagcagcgg cgggcatcat gaaaaaccca    7260
actgtcgatg gaataacagt gattgaccta gatccaatac cttatgatcc aaagtttgaa    7320
aagcagttgg gacaagtaat gctcctagtc ctctgcgtga ctcaagtatt gatgatgagg    7380
actacatggg ctctgtgtga ggcttttaacc ttagctaccg ggcccatctc cacattgtgg    7440
gaaggaaatc cagggaggtt ttggaacact accattgcgg tgtcaatggc taacattttt    7500
agagggagtt acttggccgg agctggactt ctcttttcta ttatgaagaa cacaaccaac    7560
acaagaaggg gaactggcaa cataggagag acgcttggag agaaatggaa aagccgattg    7620
aacgcattgg gaaaagtga attccagatc tacaagaaaa gtggaatcca ggaagtggat    7680
agaaccttag caaagaagg cattaaaaga ggagaaacgg accatcacgc tgtgtcgcga    7740
ggctcagcaa aactgagatg gttcgttgag agaaacatgg tcacaccaga agggaaagta    7800
gtggacctcg gttgtggcag aggaggctgg tcatactatt gtggaggact aaagaatgta    7860
agagaagtca aaggcctaac aaaaggagga ccaggacacg aagaacccat ccccatgtca    7920
acatatgggt ggaatctagt gcgtcttcaa agtggagttg acgttttctt catcccgcca    7980
gaaaagtgtg acacattatt gtgtgacata ggggagtcat caccaaatcc cacagtggaa    8040
gcaggacgaa cactcagagt ccttaactta gtagaaaatt ggttgaacaa caacactcaa    8100
ttttgcataa aggttctcaa cccatatatg ccctcagtca tagaaaaaat ggaagcacta    8160
caaaggaaat atgggaggagc cttagtgagg aatccactct cacgaaactc cacacatgag    8220
atgtactggg tatccaatgc ttccgggaac atagtgtcat cagtgaacat gatttcaagg    8280
atgttgatca acagatttac aatgagatac aagaaagcca cttacgagcc ggatgttgac    8340
ctcggaagcg gaacccgtaa catcgggatt gaaagtgaga taccaaacct agatataatt    8400
gggaaaagaa tagaaaaaat aaagcaagag catgaaacat catggcacta tgaccaagac    8460
cacccataca aaacgtgggc ataccatggt agctatgaaa caaaacagac tggatcagca    8520
tcatccatgg tcaacggagt ggtcaggctg ctgacaaaac cttgggacgt tgtccccatg    8580
gtgacacaga tggcaatgac agacacgact ccatttggac aacagcgcgt ttttaaagag    8640
aaagtggaca cgagaaccca agaaccgaaa gaaggcacga gaaactaat gaaaataaca    8700 gcagagtggc tttggaaaga attagggaag aaaagacac ccaggatgtg caccagagaa    8760
gaattcacaa gaaaggtgag aagcaatgca gccttggggg ccatattcac tgatgagaac    8820
aagtggaagt cggcacgtga ggctgttgaa gatagtaggt tttgggagct ggttgacaag    8880
gaaaggaatc tccatcttga aggaaagtgt gaaacatgtg tgtacaacat gatgggaaaa    8940
agagagaaga agctagggga attcggcaag gcaaaaggca gcagagccat atggtacatg    9000
tggcttggag cacgcttctt agagtttgaa gccctaggat tcttaaatga agatcactgg    9060
ttctccagag agaactccct gagtggagtg aaggagaag gctgcacaa gctaggttac    9120 attctaagag acgtgagcaa gaaagaggga ggagcaatgt atgccgatga caccgcagga    9180
tgggatacaa aaatcacact agaagaccta aaaaatgaag atgggtaac aaaccacatg    9240 gaaggagaac acaagaaact agccgaggcc attttcaaac taacgtacca aaacaaggtg    9300
```

```
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg gaaccttca    9660 agaggatgga atgattggac acaagtgccc ttctgttcac accatttcca tgagttaatc   9720
atgaaagacg tcgcgtact cgttgttcca tgtagaaacc aagatgaact gattggcaga    9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aaacatggga ggaaatccca  10080
tacttgggga aaagagaaga ccaatggtgc ggctcattga ttgggttaac aagcagggcc  10140
acctgggcaa agaacatcca agcagcaata atcaagtta gatcccttat aggcaatgaa   10200
gaatacacag attacatgcc atccatgaaa agattcagaa gagaagagga agaagcagga  10260
gttctgtggt agaaagcaaa actaactga aacaaggcta aagtcaggt cggattaagc    10320 catagtacgg aaaaaactat gctacctgtg agccccgtcc naggacgtta aaagaagtca  10380
ggccatcata atgccatag cttgagtaaa ctatgcagcc tgtagctcca cctgagaagg   10440
tgtaaaaaat ccgggaggcc acaaaccatg gaagctgtac gcatggcgta gtggactagc   10500
ggttagggga gaccoctccc ttacaaatcg cagcaacaat gggggcccaa ggcgagatga  10560
agctgtagtc tcgctggaag gactagaggt tagaggagac cccccgaaa caaaaaacag   10620 catattgacg ctgggaaaga ccagagatcc tgctgtctcc tcagcatcat tccaggcaca   10680
gaacgccaga aaatggaatg gtgctgttga atcaacaggt tct                    10723
```

<210> SEQ ID NO 41
<211> LENGTH: 3392
<212> TYPE: PRT
<213> ORGANISM: Dengue virus
<220> FEATURE:
<221> NAME/KEY: CHAIN
<222> LOCATION: (1)..(114)
<223> OTHER INFORMATION: capsid protein
<220> FEATURE:
<221> NAME/KEY: CHAIN
<222> LOCATION: (115)..(280)
<223> OTHER INFORMATION: premembrane protein
<220> FEATURE:
<221> NAME/KEY: CHAIN
<222> LOCATION: (281)..(775)
<223> OTHER INFORMATION: envelope glycoprotein
<220> FEATURE:
<221> NAME/KEY: CHAIN
<222> LOCATION: (776)..(1127)
<223> OTHER INFORMATION: nonstructural protein 1
<220> FEATURE:
<221> NAME/KEY: CHAIN
<222> LOCATION: (1128)..(1345)
<223> OTHER INFORMATION: nonstructural protein 2A
<220> FEATURE:
<221> NAME/KEY: CHAIN
<222> LOCATION: (1346)..(1475)
<223> OTHER INFORMATION: nonstructural protein 2B
<220> FEATURE:
<221> NAME/KEY: CHAIN

```
<222> LOCATION: (1476)..(2094)
<223> OTHER INFORMATION: nonstructural protein 3
<220> FEATURE:
<221> NAME/KEY: CHAIN
<222> LOCATION: (2095)..(2244)
<223> OTHER INFORMATION: nonstructural protein 4A
<220> FEATURE:
<221> NAME/KEY: CHAIN
<222> LOCATION: (2245)..(2493)
<223> OTHER INFORMATION: nonstructural protein 4B
<220> FEATURE:
<221> NAME/KEY: CHAIN
<222> LOCATION: (2494)..(3392)
<223> OTHER INFORMATION: nonstructural protein 5

<400> SEQUENCE: 41
```

Met Ile Asn Gln Arg Lys Lys Thr Gly Arg Pro Ser Phe Asn Met Leu
1               5                   10                  15

Lys Arg Ala Arg Asn Arg Val Ser Thr Val Ser Gln Leu Ala Lys Arg
            20                  25                  30

Phe Ser Lys Gly Leu Leu Ser Gly Gln Gly Pro Met Lys Leu Val Met
        35                  40                  45

Ala Phe Ile Ala Phe Leu Arg Phe Leu Ala Ile Pro Pro Thr Ala Gly
    50                  55                  60

Ile Leu Ala Arg Trp Gly Ser Phe Lys Lys Asn Gly Ala Ile Lys Val
65                  70                  75                  80

Leu Arg Gly Phe Lys Arg Glu Ile Ser Asn Met Leu Asn Ile Met Asn
                85                  90                  95

Arg Arg Lys Arg Ser Val Thr Met Leu Leu Met Leu Leu Pro Thr Ala
            100                 105                 110

Leu Ala Phe His Leu Thr Thr Arg Gly Gly Glu Pro His Met Ile Val
        115                 120                 125

Ser Lys Gln Glu Arg Gly Lys Ser Leu Leu Phe Lys Thr Ser Ala Gly
    130                 135                 140

Val Asn Met Cys Thr Leu Ile Ala Met Asp Leu Gly Glu Leu Cys Glu
145                 150                 155                 160

Asp Thr Met Thr Tyr Lys Cys Pro Arg Ile Thr Glu Ala Glu Pro Asp
                165                 170                 175

Asp Val Asp Cys Trp Cys Asn Ala Thr Asp Thr Trp Val Thr Tyr Gly
            180                 185                 190

Thr Cys Ser Gln Thr Gly Glu His Arg Arg Asp Lys Arg Ser Val Ala
        195                 200                 205

Leu Ala Pro His Val Gly Leu Gly Leu Glu Thr Arg Ala Glu Thr Trp
    210                 215                 220

Met Ser Ser Glu Gly Ala Trp Lys Gln Ile Gln Lys Val Glu Thr Trp
225                 230                 235                 240

Ala Leu Arg His Pro Gly Phe Thr Val Ile Ala Leu Phe Leu Ala His
                245                 250                 255

Ala Ile Gly Thr Ser Ile Thr Gln Lys Gly Ile Ile Phe Ile Leu Leu
            260                 265                 270

Met Leu Val Thr Pro Ser Met Ala Met Arg Cys Val Gly Ile Gly Asn
        275                 280                 285

Arg Asp Phe Val Glu Gly Leu Ser Gly Ala Thr Trp Val Asp Val Val
    290                 295                 300

Leu Glu His Gly Ser Cys Val Thr Thr Met Ala Lys Asn Lys Pro Thr
305                 310                 315                 320

Leu Asp Ile Glu Leu Leu Lys Thr Glu Val Thr Asn Pro Ala Val Leu
                325                 330                 335

```
Arg Lys Leu Cys Ile Glu Ala Lys Ile Ser Asn Thr Thr Asp Ser
            340                 345                 350

Arg Cys Pro Thr Gln Gly Glu Ala Thr Leu Val Glu Glu Gln Asp Ala
            355                 360                 365

Asn Phe Val Cys Arg Arg Thr Phe Val Asp Arg Gly Trp Gly Asn Gly
            370                 375                 380

Cys Gly Leu Phe Gly Lys Gly Ser Leu Ile Thr Cys Ala Lys Phe Lys
385                 390                 395                 400

Cys Val Thr Lys Leu Glu Gly Lys Ile Ala Gln Tyr Glu Asn Leu Lys
            405                 410                 415

Tyr Ser Val Ile Val Thr Val His Thr Gly Asp Gln His Gln Val Gly
            420                 425                 430

Asn Glu Thr Thr Glu His Gly Thr Thr Ala Thr Ile Thr Pro Gln Ala
            435                 440                 445

Pro Thr Ser Glu Ile Gln Leu Thr Asp Tyr Gly Thr Leu Thr Leu Asp
            450                 455                 460

Cys Ser Pro Arg Thr Gly Leu Asp Phe Asn Glu Met Val Leu Leu Thr
465                 470                 475                 480

Met Lys Lys Lys Ser Trp Leu Val His Lys Gln Trp Phe Leu Asp Leu
            485                 490                 495

Pro Leu Pro Trp Thr Ser Gly Ala Leu Thr Ser Gln Glu Thr Trp Asn
            500                 505                 510

Arg Gln Asp Leu Leu Val Thr Phe Lys Thr Ala His Ala Lys Lys Gln
            515                 520                 525

Glu Val Val Val Leu Gly Ser Gln Glu Gly Ala Met His Thr Ala Leu
            530                 535                 540

Thr Gly Ala Thr Glu Ile Gln Thr Ser Gly Thr Thr Thr Ile Phe Ala
545                 550                 555                 560

Gly His Leu Lys Cys Arg Leu Lys Met Asp Lys Leu Thr Leu Lys Gly
            565                 570                 575

Met Ser Tyr Val Met Cys Thr Gly Ser Phe Lys Leu Glu Lys Glu Val
            580                 585                 590

Ala Glu Thr Gln His Gly Thr Val Leu Val Gln Val Lys Tyr Glu Gly
            595                 600                 605

Thr Asp Ala Pro Cys Lys Ile Pro Phe Ser Thr Gln Asp Glu Lys Gly
            610                 615                 620

Ala Thr Gln Asn Gly Arg Leu Ile Thr Ala Asn Pro Ile Val Thr Asp
625                 630                 635                 640

Lys Glu Lys Pro Val Asn Ile Glu Ala Glu Pro Pro Phe Gly Glu Ser
            645                 650                 655

Tyr Ile Val Val Gly Ala Gly Glu Lys Ala Leu Lys Leu Ser Trp Phe
            660                 665                 670

Lys Lys Gly Ser Ser Ile Gly Lys Met Phe Glu Ala Thr Ala Arg Gly
            675                 680                 685

Ala Arg Arg Met Ala Ile Leu Gly Asp Thr Ala Trp Asp Phe Gly Ser
            690                 695                 700

Ile Gly Gly Val Phe Thr Ser Met Gly Lys Leu Val His Gln Val Phe
705                 710                 715                 720

Gly Thr Ala Tyr Gly Val Leu Phe Ser Gly Val Ser Trp Thr Met Lys
            725                 730                 735

Ile Gly Ile Gly Ile Leu Leu Thr Trp Leu Gly Leu Asn Ser Arg Asn
            740                 745                 750
```

-continued

Thr Ser Leu Ser Val Met Cys Ile Ala Val Gly Met Thr Leu Tyr
        755                 760                 765
Leu Gly Val Met Val Gln Ala Asp Ser Gly Cys Val Ile Asn Trp Lys
    770                 775                 780
Gly Arg Glu Leu Lys Cys Gly Ser Gly Ile Phe Val Thr Asn Glu Val
785                 790                 795                 800
His Thr Trp Thr Glu Gln Tyr Lys Phe Gln Ala Asp Ser Pro Lys Arg
                805                 810                 815
Leu Ser Ala Ala Ile Gly Lys Ala Trp Glu Gly Val Cys Gly Ile
            820                 825                 830
Arg Ser Ala Thr Arg Leu Glu Asn Ile Met Trp Lys Gln Ile Ser Asn
        835                 840                 845
Glu Leu Asn His Ile Leu Leu Glu Asn Asp Met Lys Phe Thr Val Val
    850                 855                 860
Val Gly Asp Val Ser Gly Ile Leu Ala Gln Gly Lys Lys Met Ile Arg
865                 870                 875                 880
Pro Gln Pro Met Glu His Lys Tyr Ser Trp Lys Ser Trp Gly Lys Ala
                885                 890                 895
Lys Ile Ile Gly Ala Asp Val Gln Asn Thr Thr Phe Ile Ile Asp Gly
            900                 905                 910
Pro Asn Thr Pro Glu Cys Pro Asp Asn Gln Arg Ala Trp Asn Ile Trp
        915                 920                 925
Glu Val Glu Asp Tyr Gly Phe Gly Ile Phe Thr Thr Asn Ile Trp Leu
    930                 935                 940
Lys Leu Arg Asp Ser Tyr Thr Gln Val Cys Asp His Arg Leu Met Ser
945                 950                 955                 960
Ala Ala Ile Lys Asp Ser Lys Ala Val His Ala Asp Met Gly Tyr Trp
            965                 970                 975
Ile Glu Ser Glu Lys Asn Glu Thr Trp Lys Leu Ala Arg Ala Ser Phe
        980                 985                 990
Ile Glu Val Lys Thr Cys Ile Trp Pro Lys Ser His Thr Leu Trp Ser
    995                 1000                1005
Asn Gly Val Leu Glu Ser Glu Met Ile Ile Pro Lys Ile Tyr Gly
    1010                1015                1020
Gly Pro Ile Ser Gln His Asn Tyr Arg Pro Gly Tyr Phe Thr Gln
    1025                1030                1035
Thr Ala Gly Pro Trp His Leu Gly Lys Leu Glu Leu Asp Phe Asp
    1040                1045                1050
Phe Cys Glu Gly Thr Thr Val Val Val Asp Glu His Cys Gly Asn
    1055                1060                1065
Arg Gly Pro Ser Leu Arg Thr Thr Val Thr Gly Lys Ile Ile
    1070                1075                1080
His Glu Trp Cys Cys Arg Ser Cys Thr Leu Pro Pro Leu Arg Phe
    1085                1090                1095
Lys Gly Glu Asp Gly Cys Trp Tyr Gly Met Glu Ile Arg Pro Val
    1100                1105                1110
Lys Asp Lys Glu Glu Asn Leu Val Lys Ser Met Val Ser Ala Gly
    1115                1120                1125
Ser Gly Glu Val Asp Ser Phe Ser Leu Gly Leu Leu Cys Ile Ser
    1130                1135                1140
Ile Met Ile Glu Glu Val Met Arg Ser Arg Trp Ser Lys Lys Met
    1145                1150                1155
Leu Met Thr Gly Thr Leu Ala Val Phe Leu Leu Leu Ile Met Gly

-continued

```
            1160              1165              1170
Gln Leu Thr Trp Ser Asp Leu Ile Arg Leu Cys Ile Met Val Gly
    1175              1180              1185
Ala Asn Ala Ser Asp Lys Met Gly Met Gly Thr Thr Tyr Leu Ala
    1190              1195              1200
Leu Met Ala Thr Phe Lys Met Arg Pro Met Phe Ala Val Gly Leu
    1205              1210              1215
Leu Phe Arg Arg Leu Thr Ser Arg Glu Val Leu Leu Thr Ile
    1220              1225              1230
Gly Leu Ser Leu Val Ala Ser Val Glu Leu Pro Ser Ser Leu Glu
    1235              1240              1245
Glu Leu Gly Asp Gly Leu Ala Ile Gly Ile Met Met Leu Lys Leu
    1250              1255              1260
Leu Thr Asp Phe Gln Ser His Gln Leu Trp Ala Thr Leu Leu Ser
    1265              1270              1275
Leu Thr Phe Ile Lys Thr Thr Phe Ser Leu His Tyr Ala Trp Lys
    1280              1285              1290
Thr Met Ala Met Val Leu Ser Ile Val Ser Leu Phe Pro Leu Cys
    1295              1300              1305
Leu Ser Thr Thr Ser Gln Lys Thr Thr Trp Leu Pro Val Leu Leu
    1310              1315              1320
Gly Ser Leu Gly Cys Lys Pro Leu Pro Met Phe Leu Ile Thr Glu
    1325              1330              1335
Asn Lys Ile Trp Gly Arg Lys Ser Trp Pro Leu Asn Glu Gly Ile
    1340              1345              1350
Met Ala Val Gly Ile Val Ser Ile Leu Leu Ser Ser Leu Leu Lys
    1355              1360              1365
Asn Asp Val Pro Leu Ala Gly Pro Leu Ile Ala Gly Gly Met Leu
    1370              1375              1380
Ile Ala Cys Tyr Val Ile Ser Gly Ser Ser Ala Asp Leu Ser Leu
    1385              1390              1395
Glu Lys Ala Ala Glu Val Ser Trp Glu Glu Ala Glu His Ser
    1400              1405              1410
Gly Ala Ser His Asn Ile Leu Val Glu Val Gln Asp Asp Gly Thr
    1415              1420              1425
Met Lys Ile Lys Asp Glu Glu Arg Asp Asp Thr Leu Thr Ile Leu
    1430              1435              1440
Leu Lys Ala Thr Leu Leu Ala Val Ser Gly Val Tyr Pro Met Ser
    1445              1450              1455
Ile Pro Ala Thr Leu Phe Val Trp Tyr Phe Trp Gln Lys Lys Lys
    1460              1465              1470
Gln Arg Ser Gly Val Leu Trp Asp Thr Pro Ser Pro Pro Glu Val
    1475              1480              1485
Glu Arg Ala Val Leu Asp Asp Gly Ile Tyr Arg Ile Leu Gln Arg
    1490              1495              1500
Gly Leu Leu Gly Arg Ser Gln Val Gly Val Gly Val Phe Gln Glu
    1505              1510              1515
Gly Val Phe His Thr Met Trp His Val Thr Arg Gly Ala Val Leu
    1520              1525              1530
Met Tyr Gln Gly Lys Arg Leu Glu Pro Ser Trp Ala Ser Val Lys
    1535              1540              1545
Lys Asp Leu Ile Ser Tyr Gly Gly Gly Trp Arg Phe Gln Gly Ser
    1550              1555              1560
```

-continued

Trp Asn Thr Gly Glu Glu Val Gln Val Ile Ala Val Glu Pro Gly
1565                1570                1575

Lys Asn Pro Lys Asn Val Gln Thr Thr Pro Gly Thr Phe Lys Thr
1580                1585                1590

Pro Glu Gly Glu Val Gly Ala Ile Ala Leu Asp Phe Lys Pro Gly
1595                1600                1605

Thr Ser Gly Ser Pro Ile Val Asn Arg Glu Gly Lys Ile Val Gly
1610                1615                1620

Leu Tyr Gly Asn Gly Val Val Thr Thr Ser Gly Thr Tyr Val Ser
1625                1630                1635

Ala Ile Ala Gln Ala Lys Ala Ser Gln Glu Gly Pro Leu Pro Glu
1640                1645                1650

Ile Glu Asp Lys Val Phe Arg Lys Arg Asn Leu Thr Ile Met Asp
1655                1660                1665

Leu His Pro Gly Ser Gly Lys Thr Arg Arg Tyr Leu Pro Ala Ile
1670                1675                1680

Val Arg Glu Ala Ile Lys Arg Lys Leu Arg Thr Leu Ile Leu Ala
1685                1690                1695

Pro Thr Arg Val Val Ala Ser Glu Met Ala Glu Ala Leu Lys Gly
1700                1705                1710

Val Pro Ile Arg Tyr Gln Thr Thr Ala Val Lys Ser Glu His Thr
1715                1720                1725

Gly Lys Glu Ile Val Asp Leu Met Cys His Ala Thr Phe Thr Met
1730                1735                1740

Arg Leu Leu Ser Pro Val Arg Val Pro Asn Tyr Asn Met Ile Ile
1745                1750                1755

Met Asp Glu Ala His Phe Thr Asp Pro Ala Ser Ile Ala Ala Arg
1760                1765                1770

Gly Tyr Ile Ser Thr Arg Val Gly Met Gly Glu Ala Ala Ala Ile
1775                1780                1785

Phe Met Thr Ala Thr Pro Pro Gly Ser Val Glu Ala Phe Pro Gln
1790                1795                1800

Ser Asn Ala Ile Ile Gln Asp Glu Glu Arg Asp Ile Pro Glu Arg
1805                1810                1815

Ser Trp Asn Ser Gly Tyr Asp Trp Ile Thr Asp Phe Pro Gly Lys
1820                1825                1830

Thr Val Trp Phe Val Pro Ser Ile Lys Ser Gly Asn Asp Ile Ala
1835                1840                1845

Asn Cys Leu Arg Lys Asn Gly Lys Arg Val Ile Gln Leu Ser Arg
1850                1855                1860

Lys Thr Phe Asp Thr Glu Tyr Gln Lys Thr Lys Asn Asn Asp Trp
1865                1870                1875

Asp Tyr Val Val Thr Thr Asp Ile Ser Glu Met Gly Ala Asn Phe
1880                1885                1890

Arg Ala Asp Arg Val Ile Asp Pro Arg Arg Cys Leu Lys Pro Val
1895                1900                1905

Ile Leu Lys Asp Gly Pro Glu Arg Val Ile Leu Ala Gly Pro Met
1910                1915                1920

Pro Val Thr Val Ala Ser Ala Ala Gln Arg Arg Gly Arg Ile Gly
1925                1930                1935

Arg Asn Gln Asn Lys Glu Gly Asp Gln Tyr Ile Tyr Met Gly Gln
1940                1945                1950

-continued

Pro Leu Lys Asn Asp Glu Asp His Ala His Trp Thr Glu Ala Lys
1955                1960                1965

Met Leu Leu Asp Asn Ile Asn Thr Pro Glu Gly Ile Ile Pro Ala
1970                1975                1980

Leu Phe Glu Pro Glu Arg Glu Lys Ser Ala Ala Ile Asp Gly Glu
1985                1990                1995

Tyr Arg Leu Arg Gly Glu Ala Arg Lys Thr Phe Val Glu Leu Met
2000                2005                2010

Arg Arg Gly Asp Leu Pro Val Trp Leu Ser Tyr Lys Val Ala Ser
2015                2020                2025

Glu Gly Phe Gln Tyr Ser Asp Arg Arg Trp Cys Phe Asp Gly Glu
2030                2035                2040

Arg Asn Asn Gln Val Leu Glu Glu Asn Met Asp Val Glu Ile Trp
2045                2050                2055

Thr Lys Glu Gly Glu Arg Lys Lys Leu Arg Pro Arg Trp Leu Asp
2060                2065                2070

Ala Arg Thr Tyr Ser Asp Pro Leu Ala Leu Arg Glu Phe Lys Glu
2075                2080                2085

Phe Ala Ala Gly Arg Arg Ser Val Ser Gly Asp Leu Ile Leu Glu
2090                2095                2100

Ile Gly Lys Leu Pro Gln His Leu Thr Gln Arg Ala Gln Asn Ala
2105                2110                2115

Leu Asp Asn Leu Val Met Leu His Asn Ser Glu Gln Gly Gly Lys
2120                2125                2130

Ala Tyr Arg His Ala Met Glu Glu Leu Pro Asp Thr Ile Glu Thr
2135                2140                2145

Leu Met Leu Leu Ala Leu Ile Ala Val Leu Thr Gly Gly Val Thr
2150                2155                2160

Leu Phe Phe Leu Ser Gly Arg Gly Leu Gly Lys Thr Ser Ile Gly
2165                2170                2175

Leu Leu Cys Val Met Ala Ser Ser Ala Leu Leu Trp Met Ala Ser
2180                2185                2190

Val Glu Pro His Trp Ile Ala Ala Ser Ile Ile Leu Glu Phe Phe
2195                2200                2205

Leu Met Val Leu Leu Ile Pro Glu Pro Asp Arg Gln Arg Thr Pro
2210                2215                2220

Gln Asp Asn Gln Leu Ala Tyr Val Val Ile Gly Leu Leu Phe Val
2225                2230                2235

Ile Leu Thr Val Ala Ala Asn Glu Met Gly Leu Leu Glu Thr Thr
2240                2245                2250

Lys Lys Asp Leu Gly Ile Gly His Val Ala Ala Glu Asn His His
2255                2260                2265

His Ala Thr Met Leu Asp Val Asp Leu His Pro Ala Ser Ala Trp
2270                2275                2280

Thr Leu Tyr Ala Val Ala Thr Thr Ile Ile Thr Pro Met Met Arg
2285                2290                2295

His Thr Ile Glu Asn Thr Thr Ala Asn Ile Ser Leu Thr Ala Ile
2300                2305                2310

Ala Asn Gln Ala Ala Ile Leu Met Gly Leu Asp Lys Gly Trp Pro
2315                2320                2325

Ile Ser Lys Met Asp Ile Gly Val Pro Leu Leu Ala Leu Gly Cys
2330                2335                2340

Tyr Ser Gln Val Asn Pro Leu Thr Leu Ile Ala Ala Val Leu Met

```
                2345                2350                2355
Leu Val Ala His Tyr Ala Ile Ile Gly Pro Gly Leu Gln Ala Lys
        2360                2365                2370
Ala Thr Arg Glu Ala Gln Lys Arg Thr Ala Ala Gly Ile Met Lys
        2375                2380                2385
Asn Pro Thr Val Asp Gly Ile Val Ala Ile Asp Leu Asp Pro Val
        2390                2395                2400
Val Tyr Asp Ala Lys Phe Glu Lys Gln Leu Gly Gln Ile Met Leu
        2405                2410                2415
Leu Ile Leu Cys Thr Ser Gln Ile Leu Leu Met Arg Thr Thr Trp
        2420                2425                2430
Ala Leu Cys Glu Ser Ile Thr Leu Ala Thr Gly Pro Leu Thr Thr
        2435                2440                2445
Leu Trp Glu Gly Ser Pro Gly Lys Phe Trp Asn Thr Thr Ile Ala
        2450                2455                2460
Val Ser Met Ala Asn Ile Phe Arg Gly Ser Tyr Leu Ala Gly Ala
        2465                2470                2475
Gly Leu Ala Phe Ser Leu Met Lys Ser Leu Gly Gly Arg Arg
        2480                2485                2490
Gly Thr Gly Ala Gln Gly Glu Thr Leu Gly Glu Lys Trp Lys Arg
        2495                2500                2505
Gln Leu Asn Gln Leu Ser Lys Ser Glu Phe Asn Thr Tyr Lys Arg
        2510                2515                2520
Ser Gly Ile Met Glu Val Asp Arg Ser Glu Ala Lys Glu Gly Leu
        2525                2530                2535
Lys Arg Gly Glu Thr Thr Lys His Ala Val Ser Arg Gly Thr Ala
        2540                2545                2550
Lys Leu Arg Trp Phe Val Glu Arg Asn Leu Val Lys Pro Glu Gly
        2555                2560                2565
Lys Val Ile Asp Leu Gly Cys Gly Arg Gly Gly Trp Ser Tyr Tyr
        2570                2575                2580
Cys Ala Gly Leu Lys Lys Val Thr Glu Val Lys Gly Tyr Thr Lys
        2585                2590                2595
Gly Gly Pro Gly His Glu Glu Pro Ile Pro Met Ala Thr Tyr Gly
        2600                2605                2610
Trp Asn Leu Val Arg Leu His Ser Gly Lys Asp Val Phe Phe Ile
        2615                2620                2625
Pro Pro Glu Lys Cys Asp Thr Leu Leu Cys Asp Ile Gly Glu Ser
        2630                2635                2640
Ser Pro Asn Pro Thr Ile Glu Glu Gly Arg Thr Leu Arg Val Leu
        2645                2650                2655
Lys Met Val Glu Pro Trp Leu Arg Gly Asn Gln Phe Cys Ile Lys
        2660                2665                2670
Ile Leu Asn Pro Tyr Met Pro Ser Val Val Glu Thr Leu Glu Gln
        2675                2680                2685
Met Gln Arg Lys His Gly Gly Met Leu Val Arg Asn Pro Leu Ser
        2690                2695                2700
Arg Asn Ser Thr His Glu Met Tyr Trp Val Ser Cys Gly Thr Gly
        2705                2710                2715
Asn Ile Val Ser Ala Val Asn Met Thr Ser Arg Met Leu Leu Asn
        2720                2725                2730
Arg Phe Thr Met Ala His Arg Lys Pro Thr Tyr Glu Arg Asp Val
        2735                2740                2745
```

```
Asp Leu Gly Ala Gly Thr Arg His Val Ala Val Glu Pro Glu Val
    2750                2755                2760

Ala Asn Leu Asp Ile Ile Gly Gln Arg Ile Glu Asn Ile Lys Asn
    2765                2770                2775

Glu His Lys Ser Thr Trp His Tyr Asp Glu Asp Asn Pro Tyr Lys
    2780                2785                2790

Thr Trp Ala Tyr His Gly Ser Tyr Glu Val Lys Pro Ser Gly Ser
    2795                2800                2805

Ala Ser Ser Met Val Asn Gly Val Val Arg Leu Leu Thr Lys Pro
    2810                2815                2820

Trp Asp Val Ile Pro Met Val Thr Gln Ile Ala Met Thr Asp Thr
    2825                2830                2835

Thr Pro Phe Gly Gln Gln Arg Val Phe Lys Glu Lys Val Asp Thr
    2840                2845                2850

Arg Thr Pro Lys Ala Lys Arg Gly Thr Ala Gln Ile Met Glu Val
    2855                2860                2865

Thr Ala Arg Trp Leu Trp Gly Phe Leu Ser Arg Asn Lys Lys Pro
    2870                2875                2880

Arg Ile Cys Thr Arg Glu Glu Phe Thr Arg Lys Val Arg Ser Asn
    2885                2890                2895

Ala Ala Ile Gly Ala Val Phe Val Asp Glu Asn Gln Trp Asn Ser
    2900                2905                2910

Ala Lys Glu Ala Val Glu Asp Glu Arg Phe Trp Glu Leu Val His
    2915                2920                2925

Arg Glu Arg Glu Leu His Lys Gln Gly Lys Cys Ala Thr Cys Val
    2930                2935                2940

Tyr Asn Met Met Gly Lys Arg Glu Lys Lys Leu Gly Glu Phe Gly
    2945                2950                2955

Lys Ala Lys Gly Ser Arg Ala Ile Trp Tyr Met Trp Leu Gly Ala
    2960                2965                2970

Arg Phe Leu Glu Phe Glu Ala Leu Gly Phe Met Asn Glu Asp His
    2975                2980                2985

Trp Phe Ser Arg Glu Asn Ser Leu Ser Gly Val Glu Gly Glu Gly
    2990                2995                3000

Leu His Lys Leu Gly Tyr Ile Leu Arg Asp Ile Ser Arg Ile Pro
    3005                3010                3015

Gly Gly Asn Met Tyr Ala Asp Asp Thr Ala Gly Trp Asp Thr Arg
    3020                3025                3030

Ile Thr Glu Asp Asp Leu Gln Asn Glu Ala Lys Ile Thr Asp Ile
    3035                3040                3045

Met Glu Pro Glu His Ala Leu Leu Ala Thr Ser Ile Phe Lys Leu
    3050                3055                3060

Thr Tyr Gln Asn Lys Val Val Arg Val Gln Arg Pro Ala Lys Asn
    3065                3070                3075

Gly Thr Val Met Asp Val Ile Ser Arg Arg Asp Gln Arg Gly Ser
    3080                3085                3090

Gly Gln Val Gly Thr Tyr Gly Leu Asn Thr Phe Thr Asn Met Glu
    3095                3100                3105

Ala Gln Leu Ile Arg Gln Met Glu Ser Glu Gly Ile Phe Leu Pro
    3110                3115                3120

Ser Glu Leu Glu Thr Pro Asn Leu Ala Gly Arg Val Leu Asp Trp
    3125                3130                3135
```

```
Leu Glu  Lys Tyr Gly Val Glu  Arg Leu Lys Arg Met  Ala Ile Ser
    3140                 3145                 3150

Gly Asp  Asp Cys Val Val Lys  Pro Ile Asp Asp Arg  Phe Ala Thr
    3155                 3160                 3165

Ala Leu  Thr Ala Leu Asn Asp  Met Gly Lys Val Arg  Lys Asp Ile
    3170                 3175                 3180

Pro Gln  Trp Glu Pro Ser Lys  Gly Trp Asn Asp Trp  Gln Gln Val
    3185                 3190                 3195

Pro Phe  Cys Ser His His Phe  His Gln Leu Ile Met  Lys Asp Gly
    3200                 3205                 3210

Arg Glu  Ile Val Val Pro Cys  Arg Asn Gln Asp Glu  Leu Val Gly
    3215                 3220                 3225

Arg Ala  Arg Val Ser Gln Gly  Ala Gly Trp Ser Leu  Arg Glu Thr
    3230                 3235                 3240

Ala Cys  Leu Gly Lys Ser Tyr  Ala Gln Met Trp Gln  Leu Met Tyr
    3245                 3250                 3255

Phe His  Arg Arg Asp Leu Arg  Leu Ala Ala Asn Ala  Ile Cys Ser
    3260                 3265                 3270

Ala Val  Pro Val Asp Trp Val  Pro Thr Ser Arg Thr  Thr Trp Ser
    3275                 3280                 3285

Ile His  Ala His His Gln Trp  Met Thr Thr Glu Asp  Met Leu Ser
    3290                 3295                 3300

Val Trp  Asn Arg Val Trp Ile  Glu Glu Asn Pro Trp  Met Glu Asp
    3305                 3310                 3315

Lys Thr  His Val Ser Ser Trp  Glu Glu Val Pro Tyr  Leu Gly Lys
    3320                 3325                 3330

Arg Glu  Asp Gln Trp Cys Gly  Ser Leu Ile Gly Leu  Thr Ala Arg
    3335                 3340                 3345

Ala Thr  Trp Ala Thr Asn Ile  Gln Val Ala Ile Asn  Gln Val Arg
    3350                 3355                 3360

Arg Leu  Ile Gly Asn Glu Asn  Tyr Leu Asp Tyr Met  Thr Ser Met
    3365                 3370                 3375

Lys Arg  Phe Lys Asn Glu Ser  Asp Pro Glu Gly Ala  Leu Trp
    3380                 3385                 3390
```

<210> SEQ ID NO 42
<211> LENGTH: 10723
<212> TYPE: DNA
<213> ORGANISM: Dengue virus
<220> FEATURE:
<221> NAME/KEY: misc_feature
<222> LOCATION: (1)..(10723)
<223> OTHER INFORMATION: LAV2

<400> SEQUENCE: 42

```
agttgttagt ctacgtggac cgacaaagac agattctttg agggagctaa gctcaatgta     60
gttctaacag ttttttaatt agagagcaga tctctgatga ataaccaacg gaaaaaggcg    120
aaaaacacgc ctttcaatat gctgaaacgc gagagaaacc gcgtgtcgac tgtgcaacag    180
ctgacaaaga gattctcact tggaatgctg cagggacgag gaccattaaa actgttcatg    240
gccctggtgg cgttccttcg tttcctaaca atcccaccaa cagcagggat attgaagaga    300
tggggaacaa ttaaaaaatc aaaagctatt aatgttttga gagggttcag gaaagagatt    360
ggaaggatgc tgaacatctt gaataggaga cgcagatctg caggcatgat cattatgctg    420
attccaacag tgatggcgtt ccatttaacc acacgtaacg gagaaccaca catgatcgtc    480
```

```
agcagacaag agaaagggaa aagtcttctg tttaaaacag aggttggcgt gaacatgtgt    540
accctcatgg ccatggacct tggtgaattg tgtgaagaca caatcacgta caagtgtccc    600
cttctcaggc agaatgagcc agaagacata gactgttggt gcaactctac gtccacgtgg    660
gtaacttatg ggacgtgtac caccatggga aacatagaa gagaaaaaag atcagtggca    720
ctcgttccac atgtgggaat gggactggag acacgaactg aaacatggat gtcatcagaa    780
ggggcctgga acatgtcca gagaattgaa acttggatct tgagacatcc aggcttcacc    840
atgatggcag caatcctggc atacaccata ggaacgacac atttccaaag agccctgatt    900
ttcatcttac tgacagctgt cactccttca atgacaatgc gttgcatagg aatgtcaaat    960
agagactttg tggaaggggt ttcaggagga agctgggttg acatagtctt agaacatgga    1020
agctgtgtga cgacgatggc aaaaaacaaa ccaacattgg attttgaact gataaaaaca    1080
gaagccaaac agcctgccac cctaaggaag tactgtatag aggcaaagct aaccaacaca    1140
acaacagaat ctcgctgccc aacacaaggg gaacccagcc taatgaaga gcaggacaaa    1200 aggttcgtct gcaaacactc catggtagac agaggatggg gaaatggatg tggactattt    1260
ggaaagggag gcattgtgac ctgtgctatg ttcagatgca aaaagaacat ggaaggaaaa    1320
gttgtgcaac cagaaaactt ggaatacacc attgtgataa cacctcactc aggggaagag    1380
catgcagtcg gaaatgacac aggaaaacat ggcaaggaaa tcaaaataac accacagagt    1440
tccatcacag aagcagaatt gacaggttat ggcactgtca caatggagtg ctctccaaga    1500
acgggcctcg acttcaatga gatggtgttg ctgcagatgg aaaataaagc ttggctggtg    1560
cacaggcaat ggttcctaga cctgccgtta ccatggttgc ccggagcgga cacacaaggg    1620
tcaaattgga tacagaaaga gacattggtc actttcaaaa atcccatgc gaagaaacag    1680 gatgttgttg ttttaggatc ccaagaaggg gccatgcaca cagcacttac aggggccaca    1740
gaaatccaaa tgtcatcagg aaacttactc ttcacaggac atctcaagtg caggctgaga    1800
atggacaagc tacagctcaa aggaatgtca tactctatgt gcacaggaaa gtttaaagtt    1860
gtgaaggaaa tagcagaaac acaacatgga acaatagtta tcagagtgca atatgaaggg    1920
gacggctctc catgcaagat ccctttgag ataatggatt tggaaaaaag acatgtctta    1980
ggtcgcctga ttacagtcaa cccaattgtg acagaaaaag atagcccagt caacatagaa    2040
gcagaacctc catttggaga cagctacatc atcataggag tagagccggg acaactgaag    2100
ctcaactggt ttaagaaagg aagttctatc ggccaaatgt ttgagacaac aatgaggggg    2160
gcgaagagaa tggccatttt aggtgacaca gcctgggatt ttggatcctt gggaggagtg    2220
tttacatcta taggaaaggc tctccaccaa gtctttggag caatctatgg agctgccttc    2280 agtgggttt catggactat gaaaatcctc ataggagtca ttatcacatg gataggaatg    2340
aattcacgca gcacctcact gtctgtgaca ctagtattgg tgggaattgt gacactgtat    2400
ttgggagtca tggtgcaggc cgatagtggt tgcgttgtga gctggaaaaa caaagaactg    2460
aaatgtggca gtgggatttt catcacagac aacgtgcaca catggacaga acaatacaag    2520
ttccaaccag aatcccttc aaaactagct tcagctatcc agaaagccca tgaagaggac    2580
atttgtggaa tccgctcagt aacaagactg gagaatctga tgtggaaaca aataacacca    2640
gaattgaatc acattctatc agaaaatgag gtgaagttaa ctattatgac aggagacatc    2700
aaaggaatca tgcaggcagg aaaacgatct ctgcggcctc agcccactga gctgaagtat    2760
tcatggaaaa catgggcaa agcaaaaatg ctctctctacag agtctcataa ccagacctt    2820 ctcattgatg gccccgaaac agcagaatgc cccaacacaa atagagcttg gaattcgttg    2880
```

```
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgaccct caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
aatccaacag ctattttctc aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtctttttca aaaccaacgc cggaacaata ggtgctgtat ctctggactt ttctcctgga   4920
acgtcaggat ctccaattat cgacaaaaaa ggaaaagttg tgggtctta tggtaatggt   4980
gttgttacaa ggagtggagc atatgtgagt gctatagccc agactgaaaa aagcattgaa   5040
gacaacccag atcgaagat gacatttttc gaaagagaa gactgaccat catggaccte   5100
cacccaggag cgggaaagac gaagagatac cttccggcca tagtcagaga agctataaaa   5160
cggggtttga gaacattaat cttggccccc actagagttg tggcagctga aatggaggaa   5220
```

```
gcccttagag gacttccaat aagataccag accccagcca tcagagctgw gcacaccggg    5280
cgggagattg tggacctaat gtgtcatgcc acatttacca tgaggctgct atcaccagtt    5340
agagtgccaa actacaacct gattatcatg gacgaagccc atttcacaga cccagcaagt    5400
atagcagcta gaggatacat ctcaactcga gtggagatgg gtgaggcagc tgggattttt    5460
atgacagcca ctcccccggg aagcagagac ccatttcctc agagcaatgc accaatcata    5520
gatgaagaaa gagaaatccc tgaacgctcg tggaattccg gacatgaatg ggtcacggat    5580
tttaaaggga agactgtttg gttcgttcca agtataaaag caggaaatga tatagcagct    5640
tgcctgagga aaaatggaaa gaaagtgata caactcagta ggaagacctt tgattctgag    5700
tatgtcaaga ctagaaccaa tgattgggac ttcgtggtta caactgacat tcagaaatg    5760 ggtgccaatt tcaaggctga gagggttata gaccccagac gctgcatgaa accagtcata    5820
ctaacagatg gtgaagagcg ggtgattctg gcaggaccta tgccagtgac ccactctagt    5880
gcagcacaaa aagagggag aataggaaga aatccaaaaa atgagaatga ccagtacata    5940
tacatggggg aacctctgga aaatgatgaa gactgtgcac actggaaaga agctaaaatg    6000
ctcctagata acatcaacac gccagaagga atcattccta gcatgttcga accagagcgt    6060
gaaaaggtgg atgccattga tggcgaatac cgcttgagag gagaagcaag gaaaaccttt    6120
gtagacttaa tgagaagagg agacctacca gtctggttgg cctacagagt ggcagctgaa    6180
ggcatcaact acgcagacag aaggtggtgt tttgatggag tcaagaacaa ccaaatccta    6240
gaagaaaacg tggaagttga atctggaca aaagaagggg aaaggaagaa attgaaaccc    6300
agatggttgg atgctaggat ctattctgac ccactggcgc taaaagaatt taaggaattt    6360
gcagccggaa gaaagtctct gaccctgaac ctaatcacag aaatgggtag gctcccaacc    6420
ttcatgactc agaaggcaag agacgcactg gacaacttag cagtgctgca cacggctgag    6480
gcaggtggaa gggcgtacaa ccatgctctc agtgaactgc cggagaccct ggagacattg    6540
cttttactga cacttctggc tacagtcacg ggagggatct ttttattctt gatgagcgca    6600
aggggcatag ggaagatgac cctgggaatg tgctgcataa tcacggctag catcctccta    6660
tggtacgcac aaatacagcc acactggata gcagcttcaa taatactgga gttttttctc    6720
atagttttgc ttattccaga acctgaaaaa cagagaacac cccaagacaa ccaactgacc    6780
tacgttgtca tagccatcct cacagtggtg gccgcaacca tggcaaacga gatgggtttc    6840
ctagaaaaaa cgaagaaaga tctcggattg ggaagcattg caacccagca acccgagagc    6900
aacatcctgg acatagatct acgtcctgca tcagcatgga cgctgtatgc cgtggccaca    6960
acatttgtta caccaatgtt gagacatagc attgaaaatt cctcagtgaa tgtgtcccta    7020
acagctatag ccaaccaagc cacagtgtta atgggtctcg ggaaaggatg gccattgtca    7080
aagatggaca tcggagttcc ccttctcgcc attggatgct actcacaagt caaccccata    7140
actctcacag cagctctttt cttattggta gcacattatg ccatcatagg gccaggactc    7200
caagcaaaag caaccagaga agctcagaaa agagcagcgg cgggcatcat gaaaaaccca    7260
actgtcgatg gaataacagt gattgaccta gatccaatac cttatgatcc aaagtttgaa    7320
aagcagttgg acaagtaat gctcctagtc ctctgcgtga ctcaagtatt gatgatgagg    7380
actacatggg ctctgtgtga ggctttaacc ttagctaccg ggcccatctc cacattgtgg    7440
gaaggaaatc cagggaggtt ttggaacact accattgcgg tgtcaatggc taacattttt    7500
agagggagtt acttggccgg agctggactt ctcttttcta ttatgaagaa cacaaccaac    7560
acaagaaggg gaactggcaa cataggagag acgcttggag agaaatggaa aagccgattg    7620
```

-continued

| | |
|---|---|
| aacgcattgg gaaaaagtga attccagatc tacaagaaaa gtggaatcca ggaagtggat | 7680 |
| agaaccttag caaaagaagg cattaaaaga ggagaaacgg accatcacgc tgtgtcgcga | 7740 |
| ggctcagcaa aactgagatg gttcgttgag agaaacatgg tcacaccaga agggaaagta | 7800 |
| gtggacctcg gttgtggcag aggaggctgg tcatactatt gtggaggact aaagaatgta | 7860 |
| agagaagtca aaggcctaac aaaaggagga ccaggacacg aagaacccat ccccatgtca | 7920 |
| acatatgggt ggaatctagt gcgtcttcaa agtggagttg acgttttctt catcccgcca | 7980 |
| gaaaagtgtg acacattatt gtgtgacata ggggagtcat caccaaatcc cacagtggaa | 8040 |
| gcaggacgaa cactcagagt ccttaactta gtagaaaatt ggttgaacaa caacactcaa | 8100 |
| ttttgcataa aggttctcaa cccatatatg ccctcagtca tagaaaaaat ggaagcacta | 8160 |
| caaaggaaat atggaggagc cttagtgagg aatccactct cacgaaactc cacacatgag | 8220 |
| atgtactggg tatccaatgc ttccgggaac atagtgtcat cagtgaacat gatttcaagg | 8280 |
| atgttgatca acagatttac aatgagatac aagaaagcca cttacgagcc ggatgttgac | 8340 |
| ctcggaagcg gaacccgtaa catcgggatt gaaagtgaga taccaaacct agatataatt | 8400 |
| gggaaaagaa tagaaaaaat aaagcaagag catgaaacat catggcacta tgaccaagac | 8460 |
| cacccataca aaacgtgggc ataccatggt agctatgaaa caaaacagac tggatcagca | 8520 |
| tcatccatgg tcaacggagt ggtcaggctg ctgacaaaac cttgggacgt tgtccccatg | 8580 |
| gtgacacaga tggcaatgac agacacgact ccatttggac aacagcgcgt ttttaaagag | 8640 |
| aaagtggaca cgagaaccca agaaccgaaa gaaggcacga agaaactaat gaaaataaca | 8700 |
| gcagagtggc tttggaaaga attagggaag aaaaagacac ccaggatgtg caccagagaa | 8760 |
| gaattcacaa gaaaggtgag aagcaatgca gccttggggg ccatattcac tgatgagaac | 8820 |
| aagtggaagt cggcacgtga ggctgttgaa gatagtaggt tttgggagct ggttgacaag | 8880 |
| gaaaggaatc tccatcttga aggaaagtgt gaaacatgtg tgtacaacat gatgggaaaa | 8940 |
| agagagaaga agctaggga attcggcaag gcaaaaggca gcagagccat atggtacatg | 9000 |
| tggcttggag cacgcttctt agagtttgaa gccctaggat tcttaaatga agatcactgg | 9060 |
| ttctccagag agaactccct gagtggagtg aaggagaag ggctgcacaa gctaggttac | 9120 |
| attctaagag acgtgagcaa gaaagaggga ggagcaatgt atgccgatga caccgcagga | 9180 |
| tgggatacaa gaatcacact agaagaccta aaaaatgaag aaatggtaac aaaccacatg | 9240 |
| gaaggagaac acaagaaact agccgaggcc attttcaaac taacgtacca aaacaaggtg | 9300 |
| gtgcgtgtgc aaagaccaac accaagaggc acagtaatgg acatcatatc gagaagagac | 9360 |
| caaagaggta gtggacaagt tggcacctat ggactcaata ctttcaccaa tatggaagcc | 9420 |
| caactaatca gacagatgga gggagaagga gtctttaaaa gcattcagca cctaacaatc | 9480 |
| acagaagaaa tcgctgtgca aaactggtta gcaagagtgg ggcgcgaaag gttatcaaga | 9540 |
| atggccatca gtgagatga ttgtgttgtg aaacctttag atgacaggtt cgcaagcgct | 9600 |
| ttaacagctc taaatgacat gggaaagatt aggaaagaca tacaacaatg gaaccttca | 9660 |
| agaggatgga atgattggac acaagtgccc ttctgttcac accatttcca tgagttaatc | 9720 |
| atgaaagacg gtcgcgtact cgttgttcca tgtagaaacc aagatgaact gattggcaga | 9780 |
| gcccgaatct cccaaggagc agggtggtct ttgcgggaga cggcctgttt ggggaagtct | 9840 |
| tacgcccaaa tgtggagctt gatgtacttc cacagacgcg acctcaggct ggcggcaaat | 9900 |
| gctatttgct cggcagtacc atcacattgg gttccaacaa gtcgaacaac ctggtccata | 9960 |

```
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
gttctgtggt agaaagcaaa actaacatga aacaaggcta gaagtcaggt cggattaagc  10320
catagtacgg aaaaaactat gctacctgtg agccccgtcc aaggacgtta aaagaagtca  10380
ggccatcata aatgccatag cttgagtaaa ctatgcagcc tgtagctcca cctgagaagg  10440
tgtaaaaaat ccgggaggcc acaaaccatg gaagctgtac gcatggcgta gtggactagc  10500
ggttagagga gacccctccc ttacaaatcg cagcaacaat gggggcccaa ggcgagatga  10560
agctgtagtc tcgctggaag gactagaggt tagaggagac ccccccgaaa caaaaaacag  10620
catattgacg ctgggaaaga ccagagatcc tgctgtctcc tcagcatcat tccaggcaca  10680
gaacgccaga aaatggaatg gtgctgttga atcaacaggt tct                    10723
```

```
<210> SEQ ID NO 43
<211> LENGTH: 10699
<212> TYPE: DNA
<213> ORGANISM: Dengue virus
<220> FEATURE:
<221> NAME/KEY: misc_feature
<222> LOCATION: (1)..(10699)
<223> OTHER INFORMATION: LAV3

<400> SEQUENCE: 43
agttgttagt ctacgtggac cgacaagaac agtttcgact cggaagcttg cttaacgtag     60
tgctgacagt tttttattag agagcagatc tctgatgaac aaccaacgga aaaagacggg    120
aaaaccgtct atcaatatgc tgaaacgcgt gagaaaccgt gtgtcaactg gatcacagtt    180
ggcgaagaga ttctcaagag gattgctgaa cggccaagga ccaatgaaat tggttatggc    240
atttatagct ttcctcagat ttctagccat tccaccgaca gcaggagtct tggctagatg    300
ggtacctttt aagaagtcgg gggctattaa ggtcttaaaa ggcttcaaga aggagatctc    360
aaacatgctg agcattatca acaaacggaa aaagacatcg ctctgtctca tgatgatgtt    420
accagcaaca cttgctttcc acttaacttc acgagatgga gagccgcgca tgattgtggg    480
gaagaatgaa agaggaaaat ccctactttt caagacagcc tctggaatca acatgtgcac    540
actcatagct atggatctgg gagagatgtg tgatgacacg gtcacttaca aatgccccca    600
cattaccgaa gtggagcctg aagacattga ctgctggtgc aaccttacat cgacatgggt    660
gacttatgga acatgcaatc aagctggaga gcatagacgc gataagagat cagtggcgtt    720
agctccccat gttggcatgg gactggacac acgcactcaa acctggatgt cggctgaagg    780
agcttggaga caagtcgaga aggtagagac atgggccctt aggcacccag ggtttaccat    840
actagcccta tttcttgccc attacatagg cacttccttg acccagaaag tggttatttt    900
tatactatta atgctggtta ccccatccat gacaatgaga tgtgtaggag taggaaacag    960
agattttgtg gaaggcctat cgggagctac gtgggttgac gtggtgctcg agcacggtgg   1020
gtgtgtgact accatggcta agaacaagcc cacgctggac atagagcttc agaagaccga   1080
ggccacccaa ctggcgaccc taaggaagct atgcattgag ggaaaaatta ccaacataac   1140
aaccgactca agatgtccca cccaagggga agcgatttta cctgaggagc aggaccagaa   1200
ctacgtgtgt aagcatacat acgtggacag aggctgggga aacggttgtg gtttgtttgg   1260
```

```
caagggaagc ttggtgacat gcgcgaaatt tcaatgttta gaatcaatag agggaaaagt    1320
ggtgcaacat gagaacctca aatacaccgt catcatcaca gtgcacacag agaccaaca     1380
ccaggtggga aatgaaacgc agggagtcac ggctgagata caccccagg catcaaccgc     1440
tgaagccatt ttacctgaat atggaaccct cgggctagaa tgctcaccac ggacaggttt    1500
ggatttcaat gaaatgatct yattgacaat gaagaacaaa gcatggatgg tacatagaca    1560
atggttcttt gacttacccc taccatggac atcaggagct acagcagaaa caccaacttg    1620
gaacaggaaa gagcttcttg tgacatttaa aaatgcacat gcaaaaaagc aagaagtagt    1680
tgttcttgga tcacaagagg gagcaatgca tacagcactg acaggagcta cagagatcca    1740
aacctcagga ggcacaagta tctttgcggg gcacttaaaa tgtagactca agatggacaa    1800
attggaactc aaagggatga gctatgcaat gtgcttgggt agctttgtgt tgaagaaaga    1860
agtctccgaa acgcagcatg gacaatact cattaaggtt gagtacaaag ggaaagatgc     1920
accctgcaag attcctttct ccacggagga tggacaagga aaagctcaca atggcagact    1980
gatcacagcc aatccagtgg tgaccaagaa ggaggagcct gtcaacattg aggctgaacc    2040
tcctttggga gaaagtaaca tagtaattgg aattggagac aaagccctga aaatcaactg    2100
gtacaagaag ggaagctcga ttgggaagat gttcgaggct actgccagag gtgcaaggcg    2160
catggccatc ttgggagaca cagcctggga ctttggatca gtgggtggtg ttttgaattc    2220
attagggaaa atggtccacc aaatatttgg gagtgcttac acagccctat ttggtggagt    2280
ctcctggatg atgaaaattg gaataggtgt cctcttaacc tggataggt tgaactcaaa     2340
aaatacttct atgtcatttt catgcatcgc gataggaatc attacactct atctgggagc    2400
cgtggtgcaa gctgacatgg ggtgtgtcat aaactgaaaa ggcaaagaac tcaaatgtgg    2460
aagtggaatt ttcgtcacta atgaggtcca cacctggaca gagcaataca aatttcaagc    2520
agactccccc aagagactgg caacagccat tgcaggcgct tgggaaaatg gagtgtgcgg    2580
aattaggtca acaaccagaa tggagaacct cttgtggaag caaatagcca atgaactgaa    2640
ttacatatta tgggaaaaca acattaaatt aacggtagtt gtaggcgaca taactggggt    2700
cttagagcaa gggaaaagaa cactaacacc acaacccatg gagctaaaat attcttggaa    2760
aacatgggga aaggcaaaaa tagtgacagc tgaaacacaa aattcctctt tcataataga    2820
tgggccaagc acaccggagt gtccaagtgc ctcaagagca tggaatgtgt gggaggtgga    2880
ggattacggg ttcggagttt tcacaaccaa catatggctg aaactccgag aggtgtacac    2940
ccaactatgt gaccatagc taatgtcggc agccgtcaag gatgagaggg ctgtacatgc     3000
cgacatgggc tattggatag aaagccaaaa gaatgggagt tggaagctag aaaaagcatc    3060
cttcatagag gtgaaaacct gcacatggcc aaaatcacac actctctgga gcaatggtgt    3120
gctagagagt gacatgatta tcccaaagag tctagctggt cccatttcgc aacacaacca    3180
caggcccggg taccacaccc aaacggcagg accctggcac ttaggaaaat ggagctggaa    3240
cttcaactat tgtgaaggaa caacagttgt catctcagaa aactgtggga caagaggccc    3300
atcattgaga acaacaacgg tgtcaggaa gttgatacac gaatggtgct gccgctcgtg    3360
cacacttcct cccctacgat acatgggaga agacggctgc tggtatgca tggaaatcag     3420
acccattaat gagaaagaag agaatatggt aaagtctcta gcctcagcag ggagtggaaa    3480
ggtgacaac ttcacaatgg gtgtcttgtg tttggcaatc ctctttgaag aggtgatgag    3540
aggaaaattt gggaaaaaac acatgattgc aggggttctc ttcacgtttg tgctcctcct    3600
```

```
ctcagggcaa ataacatgga gagacatggc gcacacactc ataatgattg ggtccaacgc    3660
ctctgacaga atggggatgg gcgtcactta cctagctcta attgcaacat ttaaaattca    3720
gccactcctg gctttgggat tcttcctgag gaaactgaca tctagagaaa atttattgct    3780
gggagttggg ttggccatgg cagcaacgtt acgactgcca gaggacattg aacagatggc    3840
gaatggaatt gctttggggc tcatggctct taaactgata acacaatttg aaacatacca    3900
actatggacg gcattagttt ccctaacgtg ttcaaataca attttcacgt tgactgttgc    3960
ctggagaaca gccactctga ttttagccgg aatttcgctt ttgccagtgt gccagtcttc    4020
gagcatgagg aaaacagatt ggctcccaat gactgtggca gctatgggag ctcaacccct    4080
accacttttt attttcagtc tgaaagatac actcaaaagg agaagctggc cactgaatga    4140
gggggtgatg gcagttggac ttgtgagcat tctagctagt tctctcctta ggaatgatgt    4200
gcctatggct ggaccattag tggctggggg cttgctgata gcgtgctacg tcataactgg    4260
cacgtcagca gacctcactg tagaaaaagc agcagatgta acatgggagg aagaggccga    4320
gcaaacagga gtgtcccaca atttaatggt cacagttgat gatgatgaa caatgagaat    4380
aaaagatgac gagactgaga acatcttaac agtgctttta aaaacagcac tactaatagt    4440
atcaggcatc tttccatact ccatacccgc aacactgttg gtctggcata cttggcaaaa    4500
gcaaacccaa agatccggcg tcctatggga cgtacccagc cccccagaga cacagaaagc    4560
ggaactggaa aaggggtct ataggatcaa acagcaagga attttgga aaacccaagt    4620
ggggttgga gtacagaaag aaggagttt ccacaccatg tggcatgtca agagggc    4680
agtgttgaca cacaatggga aaagactgga accaaactgg gctagcgtga aaaaagatct    4740
gatttcatac ggaggaggat ggagattgag tgcacaatgg aaaaggggg aggaggtgca    4800
ggttattgcc gtagagcctg ggaagaaccc aaagaacttt caaaccatgc caggcatttt    4860
tcagacaaca acagggaaa taggagcaat gcactggat ttcaagcctg gaacttcagg    4920
atctcccatc ataaacagag agggaaaggt agtgggactg tatggcaatg gagtggttac    4980
aaagaatgga ggctatgtca gtggaatagc gcaaacaaat gcagaaccag atggaccgac    5040
accagagttg gaagaagaga tgttcaaaaa gcgaaatcta accataatgg atctccatcc    5100
tgggtcagga aagacgcgga aatatcttcc agctattgtt agagaggcaa tcaagagacg    5160
cttaaggact ctaattttgg caccaacaag ggtagttgca gctgagatgg aagaagcatt    5220
gaaagggctc ccaataaggt atcaaacaac tgcaacaaaa tctgaacaca caggaagaga    5280
gattgttgat ctaatgtgtc acgcaacgtt cacaatgcgc ttgctgtcac cagtcagggt    5340
tccaaactac aacttgataa taatggatga ggcccatttc acagacccag ccagtatagc    5400
ggctagaggg tacatatcaa ctcgtgtagg aatgggagag gcagccgcaa ttttcatgac    5460
agcaacaccc cctgaacag ctgatgcctt tcctcagagc aacgctccaa ttcaagatga    5520
agagagagac ataccggaac gctcatggaa ttcaggcaat gaatggatta ctgactttgt    5580
tgggaagaca gtgtggtttg tccctagcat caaagccgga aatgacatag caactgcttt    5640
gcggaaaaat ggaaaaaagg ttattcaact cagcaggaag acctttgaca cagaatatca    5700
aaagaccaaa ctgaatgatt gggactttgt ggtgacaaca gacatttcag aaatgggagc    5760
caatttcaaa gcagatagag tgatcgaccc aagaagatgt ctcaagccgg tgattttgac    5820
agatggaccc gagcgggtga tcctggctgg accaatgcca gtcaccgtag cgagcgctgc    5880
gcaaaggaga gggagagttg gcaggaaccc acaaaaagaa aatgaccagt acatattcat    5940
gggccagcct ctcaacaatg atgaagacca tgctcactgg acagaagcaa aaatgctgct    6000
```

```
ggacaacatc aacacaccag aagggattat accagctctc tttgaaccag aaagggagaa    6060
gtcagccgcc atagacggcg aataccgcct gaagggtgag tccaggaaga ctttcgtgga    6120
actcatgagg aggggtgacc tcccagtttg gctagcccat aaagtagcat cagaagggat    6180
caaatataca gatagaaaat ggtgctttga tggagaacgt aataatcaaa ttttagagga    6240
gaatatggat gtggaaatct ggacaaagga aggagaaaag aaaaaactga gacctaggtg    6300
gcttgatgcc cgcacttatt cagatccttt agcactcaaa gaattcaagg attttgcagc    6360
tggcagaaag tcaatcgccc ttgatcttgt gacagaaata ggaagagtgc cttcacactt    6420
agcccacaga acgagaaacg ccctggataa tttggtgatg ctgcacacgt cagaacatgg    6480
cggtagggcc tacaggcatg cagtggagga actaccagaa acgatggaaa cactcttact    6540
cctgggactg atgatcttgt aacaggtgg agcaatgctc ttcttgatat caggtaaagg    6600
gattggaaag acttcaatag gactcatttg tgtaattgct ccagcggca tgttatggat    6660 ggctgatgtc ccactccaat ggatcgcatc ggctatagtc ctggagtttt ttatgatggt    6720
gttgctcata ccagaaccag aaaagcagag aactccccaa gacaaccaac tcgcatatgt    6780
cgtgataggc atacttacat tggctgcaat agtagcggcc aatgaaatgg gactgttgga    6840
aactacaaag agagatttag gaatgtctaa agaaccaggt gttgtttctc caaccagcta    6900
tttggatgtg gacttgcacc cagcatcagc ctggacattg tacgccgtgg ccacaacagt    6960
aataacacca atgttgagac acaccataga gaattccaca gcaaatgtgt ctctggcagc    7020
catagctaac caggcagtgg tcctgatggg tttagacaaa ggatggccga tatcgaaaat    7080
ggacttgggc gtaccactat ggcactgggt tgctattca caagtgaacc cactaactct    7140
tgcagcggca gtactttgc tagtcacaca ttatgcaatt ataggtccag gattgcaggc    7200
aaaagccacc cgtgaagctc agaaaaggac agctgctgga ataatgaaga atccaacggt    7260
ggatggaata atgacaatag acctagatcc tgtaatatat gattcaaaat ttgaaaagca    7320
actaggacag gtcatgctcc tggttctgtg tgcagtccaa cttttattga tgagaacatc    7380
atgggccttg tgtgaagttc taaccctagc cacaggacca ataacaacac tctgggaagg    7440
atcacctggg aagttctgga acaccacgat agctgtttcc atggcgaaca tctttagagg    7500
gagctattta gcaggagctg ggcttgcttt ttctatcatg aaatcagttg aacaggaaa    7560 gagaggaaca gggtcacaag gtgaaacctt aggagaaaag tggaaaaaga attaaatca    7620 gttatcccgg aaagagtttg acctttacaa gaaatccgga atcaccgaag tggatagaac    7680
agaagccaaa gaagggttaa aaagaggaga ataacacac catgccgtgt ccagaggcag    7740
cgcaaaactt caatggttcg tggagagaaa catggtcatt cctgaaggaa gagtcataga    7800
cctaggctgt ggaagaggag ctggtcata ttactgtgca ggactgaaaa aagttacaga    7860
agtgcgagga tacacaaaag gcggcccagg acacgaagaa ccagtaccta tgtctacata    7920
cggatggaac atagtcaagt taatgagtgg aaaggatgtt ttttatctgc cacctgaaaa    7980
gtgtgatacc ctattgtgtg acattggaga atcttccacca agcccaacag tggaagaaag    8040
cagaaccata agagttttga agatggttga accatggcta agaacaacc agttttgcat    8100 taaagtattg aacccataca tgccaactgt gattgagcac ttagaaagac tacaaaggaa    8160
acatggagga atgcttgtga gaatccact ctcacgaaac tccacgcacg aaatgtattg    8220
gatatccaat ggtacaggca atatcgtctc ttcagtcaac atggtatcca gattgctact    8280
gaacagattc acaatgacac acaggagacc caccatagag aaagatgtgg atctaggagc    8340
```

```
aggaacccga catgtcaatg cggaaccaga acacccaac atggatgtca ttggggaaag   8400
aataaaaagg atcaaagagg agcatagttc aacatggcac tatgatgatg aaaatcctta   8460
caaaacgtgg gcttaccatg gatcctatga agtaaaagcc acaggctcag cctcctccat   8520
gataaatgga gtcgtgaaac tcctcacaaa accatgggag gtggtgccca tggtgacaca   8580
gatggcaatg acagatacaa ctccattcgg ccagcaaaga gttttttaaag agaaagtgga   8640
caccaggaca cctaggccca tgccaggaac aagaaaggtt atggagatca cagcggagtg   8700
gctttggagg accctgggaa ggaacaaaag acccagatta tgcacaaggg aggaattcac   8760
aaagaaggtc agaaccaacg cagctatggg cgctgtcttc acagaagaga accaatggga   8820
cagtgcgaga gctgctgttg aggacgaaga attttggaaa cttgtggaca gagaacgtga   8880
actccacaaa ctgggcaagt gtggaagctg cgtttacaac atgatgggca agagagagaa   8940
aaaacttgga gagtttggta aagcaaaagg cagtagggct atatggtaca tgtggttggg   9000
agccaggtac cttgagttcg aggcgctcgg attcctcaat gaagaccact ggttctcgcg   9060
tgaaaactct tacagtggag tagaaggaga aggactgcac aagctgggat acatcttgag   9120
agatatttcc aagataccg gaggagccat gtatgctgat gacacagccg gttgggacac   9180
aagaataaca gaagatgacc tgcacaatga ggaaaaaatc acacagcaga tggaccctga   9240
acacaggcag ctagcgaacg ctatattcaa gctcacatac caaaacaaag tggtcaaagt   9300
ccaacgacca actccaaagg gcacggtaat ggacatcata tctaggaaag accaagagg   9360
cagtggacag gtgggaactt atggtctgaa cacattcacc aacatggaag cccagctaat   9420
cagacaaatg gaaggagaag gcgtgttgtc aaaggcagca ctcgagaacc ccatccgct   9480
agagaagaaa attacacaat ggttggaaac taaaggagtg gaaaggttaa aaagaatggc   9540
catcagcggg gatgattgcg ttgtgaaacc aatcgacgac agattcgcca atgccctgct   9600
tgccctgaac gatatgggaa aggttagaaa ggacatacct caatggcagc catcaaaggg   9660
atggcatgat tggcaacagg tccccttctg ctcccaccac tttcatgaat tgatcatgaa   9720
agatgggaga aagttggtag ttcccctgca gacccccagga gaactaatag aagagcgag   9780
aatctcccaa ggagcaggat ggagccttag agaaactgca tgtctaggga aagcctacgc   9840
tcaaatgtgg gctctcatgt atttttcacag aagagatctt agactagcat ccaacgccat   9900
atgttcagca gtaccagtcc actgggtccc cacgagcaga acgacatggt ctattcatgc   9960
tcaccatcag tggatgacta cagaagacat gcttactgtc tggaacaggg tgtggataga  10020
ggacaatcca tggatggaag acaaaactcc agtcacaacg tgggaagatg ttccatatct  10080
agggaagaga gaagaccaat ggtgcggatc actcatagt ctcacttcca gagcaacctg  10140
ggcccagaac atactcacag caatccaaca ggtgagaagc ctcataggca atgaagagtt  10200
tctggactac atgccttcga tgaagagatt caggaaggag gaggagtcag agggagccat  10260
ttggtaaaag caggaggtaa actgtcaggc cacattaagc cacagtacgg aagaagctgt  10320
gcagcctgtg agccccgtcc aaggacgtta aaagaagaag tcaggcccaa aagccacggt  10380
ttgagcaaac cgtgctgcct gtagctccgt cgtggggacg taaagcctgg gaggctgcaa  10440
accgtggaag ctgtacgcac ggtgtagcag actagtggtt agaggagacc cctcccatga  10500
cacaacgcag cagcggggcc cgagcactga gggaagctgt acctccttgc aaaggactag  10560
aggttagagg agaccccccg caaacaaaaa cagcatattg acgctgggag agaccagaga  10620
tcctgctgtc tcctcagcat cattccaggc acagaacgcc agaaaatgga atggtgctgt  10680
tgaatcaaca ggttctagt                                              10699
```

<210> SEQ ID NO 44
<211> LENGTH: 10648
<212> TYPE: DNA
<213> ORGANISM: Dengue virus
<220> FEATURE:
<221> NAME/KEY: misc_feature
<222> LOCATION: (1)..(10648)
<223> OTHER INFORMATION: LAV4

<400> SEQUENCE: 44
agttgttagt ctgtgtggac cgacaaggac agttccaaat cggaagcttg cttaacacag 60
ttctaacagt ttgtttgaat agagagcaga tctctggaaa aatgaaccaa cgaaaaaagg 120
tggttagacc acctttcaat atgctgaaac gcgagagaaa ccgcgtatca acccctcaag 180
ggttggtgaa gagattctca accggacttt tttctgggaa aggaccctta cggatggtgc 240
tagcattcat cacgtttttg cgagtccttt ccatcccacc aacagcaggg attctgaaaa 300
gatggggaca gttgaagaaa aataaggcca tcaggatact gattggattc aggaaggaga 360
taggccgcat gctgaacatc ttgaacggga gaaaaaggtc aacgataaca ttgctgtgct 420
tgattcccac cgtaatggcg tttcacttgt caacaagaga tggcgaaccc ctcatgatag 480
tggcaaaaca tgaaaggggg agacctctct tgtttaagac aacagagggg atcaacaaat 540
gcactctcat tgccatggac ttgggtgaaa tgtgtgagga cactgtcacg tataaatgcc 600
ccttactggt caataccgaa cctgaagaca ttgattgctg gtgcaatctc acgtctacct 660
gggtcatgta tgggacatgc acccagagcg gagaacggag acgagagaag cgctcagtag 720
ctttaacacc acattcagga atgggattgg aaacaagagc tgagacatgg atgtcatcgg 780
aaggggcttg gaagcatgct cagagagtag agagctggat actcagaaac ccaggattcg 840
cgctcttggc aggatttatg gcttatatga ttgggcaaac aggaatccag cgaactgtct 900
tctttgtcct aatgatgctg gtcgccccat cctacggaat gcgatgcgta ggagtaggaa 960
acagagactt tgtggaagga gtctcaggtg gagcatgggt cgatctggtg ctagaacatg 1020
gaggatgcgt cacaaccatg gcccagggaa aaccaacctt ggattttgaa ctgactaaga 1080
caacagccaa ggaagtggct ctgttaagaa cctattgcat tgaagcctca atatcaaaca 1140
taaccacggc aacaagatgt ccaacgcaag gagagcctta tctaaaagag gaacaagacc 1200
aacagtacat ctgccggaga gatgtggtag acagagggtg gggcaatggc tgtggcttgt 1260
ttggaaaagg aggagttgtg acatgtgcga agttttcatg ttcggggaag ataacaggca 1320
atttggtcca aattgagaac cttgaataca cagtggttgt aacagtccac aatggagaca 1380
cccatgcagt aggaaatgac acatccaatc atggagttac agccacgata actcccaggt 1440
caccatcggt ggaagtcaaa ttgccggact atggagaact aacactcgat tgtgaaccca 1500
ggtctggaat tgactttaat gagatgattc tgatgaaaat gaaaaagaaa acatggcttg 1560
tgcataagca atggtttttg gatctacctc taccatggac agcaggagca gacacatcag 1620
aggttcactg gaattacaaa gagagaatgg tgacatttaa ggttcctcat gccaagagac 1680
aggatgtgac agtgctggga tctcaggaag gagccatgca ttctgccctc gctggagcca 1740
cagaagtgga ctccggtgat ggaaatcaca tgtttgcagg acatctcaag tgcaaagtcc 1800
gtatggagaa attgagaatc aagggaatgt catacacgat gtgttcagga aagttctcaa 1860
ttgacaaaga gatggcagaa acacagcatg ggacaacagt ggtgaaagtc aagtatgaag 1920
gtgctggagc tccgtgtaaa gtccccatag agataagaga tgtgaacaag aaaaaagtgg 1980

```
ttgggcgtat catctcatcc accccttttgg ctgagaatac caacagtgca accaacatag   2040
agttagaacc cccctttggg gacagctaca tagtgatagg tgttggaaac agtgcattaa   2100
cactccattg gttcaggaaa gggagttcca ttggcaagat gtttgagtcc acatacagag   2160
gtgcaaaacg aatggccatt ctaggtgaaa cagcttggga ttttggttcc gttggtggac   2220
tgttcacatc attgggaaag gctgtgcacc aggttttttgg aagtgtgtat acaaccatgt   2280
ttggaggagt ctcatggatg attagaatcc taattgggtt cctagtgttg tggattggca   2340
cgaactcaag gaacacttca atggctatga cgtgcatagc tgttggagga atcactctgt   2400
ttctgggctt cacagttcaa gcagacatgg gttgtgtggt gtcatggagt gggaaagaat   2460
tgaagtgtgg aagcggaatt tttgtggttg acaacgtgca cacttggaca gaacagtaca   2520
aatttcaacc ggagtcccca gcgagactag cgtctgcaat attgaatgcc cacaaagatg   2580
gggtctgtgg aattagatca accacgaggc tggaaaatgt catgtggaag caaataacca   2640
acgagctaaa ttatgttctc tgggaaggag gacatgacct cactgtagtg gctggggatg   2700 tgaaggggt gttgaccaaa ggcaagagag cactcacacc cccagtgaat gatctgaaat   2760
attcatggaa gacatgggga aaagcaaaaa tcttcaccc agaagcaaga aatagcacat   2820
ttttaataga cggaccagac acctccgaat gccccaatga cgaagagca tggaactttc   2880 ttgaggtgga agactatgga tttggcatgt tcacgaccaa catatggatg aaattccgag   2940
aaggaagttc agaagtgtgt gaccacaggt taatgtcagc ggcaattaaa gatcagaaag   3000
ctgtgcatgc tgacatgggt tattggatag agagctcaaa aaaccagacc tggcagatag   3060
agaaagcatc tcttattgaa gtgaaaacat gtctgtggcc caagacccac acattgtgga   3120
gcaatggagt gctggaaagc cagatgctca ttccaaaatc atatgcgggc cctttttcac   3180
accacaatta ccgccaggc tatgccacgc aaacgtggg cccatggcac ttaggcaaat   3240 tagagatag cttttggagaa tgccccggaa caacagtcgc aattcaggag gattgtgacc   3300
atagaggccc atcttgagg accaccactg catctggaaa actagtcacg caatggtgct   3360
gccgctcctg cacgatgcct cccttaaggt tcttgggaga agatgggtgc tggtatggga   3420
tggagattag gccccttgagt gaaaaagaag agaacatggt caaatcacag gtaacggccg   3480
gacagggcac atcagaaact ttttctatgg gtctgttgtg cctgaccttg tttgtggaag   3540
aatgcttgag gagaagagtc actaggaaac acatgatatt ggttgtggtg atcactcttt   3600
gtgccatcat cctaggaggc ctcacatgga tggacttact acgagccctc atcatgttgg   3660
gggacactat gtctggtaga ataggaggac agatccacct agccatcatg gcagtgttca   3720
agatgtcacc aggatacgtg ctgggtgtgt ttttaaggaa actcacttca agagagacag   3780
cactaatggt aataggaatg gccatgacaa cggtgctttc aattccacat gaccttatgg   3840
aactcattga tggaatatca ctggggctaa ttttgctaaa aatagtgaca cattttgaca   3900
acacccaagt gggaaccta gcccttttcct tgaccttcat aagatcaaca atgccattgg   3960
tcatggcttg gaggaccatt atggctgtgt tgtttgtggt cacactcatt cctttgtgca   4020
ggacaagctg tcttcaaaaa cagtctcatt gggtagaaat aacagcactc atcctaggag   4080
cccaagctct gccagtgtac ctaatgactc ttatgaaagg agcctcaaga agatcttggc   4140
ctcttaacga gggcataatg gctgtgggtt tggttagtct cttaggaagc gctcttttaa   4200
agaatgatgt ccctttagct ggcccaatgg tggcaggagg cttacttctg cgggcttacg   4260
tgatgagtgg tagctcagca gatctgtcac tagagaaggc cgccaatgtg cagtgggatg   4320
aaatggcaga cataacaggc tcaagcccaa tcatagaagt gaagcaggat gaagatggct   4380
```

```
cttttctccat acgggacgtc gaggaaacca atatgataac ccttttggtg aaactggcac    4440
tgataacagt gtcaggtctc taccccttgg caattccagt cacaatgacc ttatggtaca    4500
tgtggcaagt gaaaacacaa agatcaggag ccctgtggga cgtcccctca cccgctgcca    4560
ctcaaaaagc cgcactgtct gaaggagtgt acaggatcat gcaaagaggg ttatttggga    4620
aaactcaggt tggagtaggg atacacatgg aaggtgtatt tcacacaatg tggcatgtaa    4680
caagaggatc agtgatctgc catgagactg ggagattgga gccatcttgg gctgacgtca    4740
ggaatgacat gatatcatac ggtgggggat ggagacttgg agacaaatgg gacaaagaag    4800
aagatgttca ggtcctcgcc atagaaccag gaaaaaatcc taaacatgtc caaacgaaac    4860
ccggcctttt caagacccta actggagaaa ttggagcagt aacattagat ttcaaacccg    4920
gaacgtctgg ttctcccatc atcaacagga aggaaaagt catcggactc tatggaaatg    4980
gagtagttac caaatcaggt gattacgtca gtgccataac gcaagccgaa agaattggag    5040
agccagatta tgaagtggat gaggacattt ttcgaaagaa aagattaact ataatggact    5100
tacaccccgg agctggaaag acaaaaagaa ttcttccatc aatagtgaga gaagccttaa    5160
aaaggaggct gcgaaccttg attttggctc ccacgagagt ggtggcggcc gagatggaag    5220
aggccctacg tggactgcca atccgttatc agaccccagc tgtgaaatca gaacacacag    5280
gaagagagat tgtagacctc atgtgtcatg caaccttcac aacaagactt ttgtcatcaa    5340
ccagagttcc aaattacaac ctcatagtga tggatgaagc acatttcacc gatccttcta    5400
gtgtcgcggc tagaggatac atctcgacca gggtggaaat gggagaggca gcagccatct    5460
tcatgaccgc aaccccctccc ggagcgacag atccctttcc ccagagcaac agcccaatag    5520
aagacatcga gagggaaatt ccggaaaggt catggaacac agggttcgac tggataacag    5580
actaccaagg gaaaactgtg tggtttgttc ccagcataaa agctggaaat gacattgcaa    5640
attgtttgag aaagtcggga aagaaagtta tccagttgag taggaaaacc tttgatacag    5700
agtatccaaa aacgaaactc acggactggg attttgtggt cactacagac atatctgaaa    5760 tggggggccaa ttttagagct gggagagtga tagaccctag gagatgcctc aagccagtta    5820
tcctaacaga tgggccagag agagtcattt tagcaggtcc tattccagtg actccagcaa    5880
gcgctgctca gagaagaggg cgaataggaa ggaacccagc acaagaagac gaccaatacg    5940
ttttctccgg agacccacta aaaaatgatg aagatcatgc ccactggaca gaagcaaaga    6000
tgctgcttga caatatctac accccagaag ggatcattcc aacattgttt ggtccggaaa    6060
gggaaaaaac ccaagccatt gatggagagt ttcgcctcag aggggaacaa aggaagactt    6120
ttgtggaatt aatgaggaga ggagaccttc cggtgtggct gagctataag gtagcttctg    6180
ctggcatttc ttacaaagat cgggaatggt gcttcacagg ggaaaggaat aaccaaattt    6240
tagaagaaaa catggaggtt gaaatttgga ctagagaggg agaaaagaaa aagctaaggc    6300
caagatggtt agatgcacgt gtatacgctg accccatggc tttgaaggat tttaaggagt    6360 tgctagtgg aaggaagagc ataactctcg acatcctaac agagattgcc agtttgccaa    6420
cttacctttc ctctagggcc aagctcgccc ttgataacat agtcatgctc cacacaacag    6480
aaagaggagg gagggcctac caacacgccc tgaacgaact cccggagtca ctggaaacac    6540
ttatgcttgt agctttacta ggtgctatga cagcaggtat cttcctgttt ttcatgcaag    6600
ggaaaggaat agggaaattg tcaatggggtt tgataaccat tgcggtggct agtggcttgt    6660
tctgggtagc agaaattcaa ccccagtgga tagcggcctc aatcatacta gagttttttc    6720
```

```
tcatggtact gttgataccg gaaccagaaa acaaaggac cccacaagac aatcaattga    6780
tctacgtcat attgaccatt ctcaccatta ttggtctcat agcagccaac gagatggggc    6840
tgattgaaaa acaaaaacg gatttttgggt tttaccaggt aaaaacagaa accaccatcc   6900
tcgatgtgga cttgagacca gcttcagcat ggacgctcta tgcagtagcc accacawttc   6960
tgactcccat gctgagacac accatagaaa acacgtcggc caacctatct ctagcagcca   7020
ttgccaacca gcggccgtc ctaatggggc ttggaaaagg atggccgctc cacagaatgg     7080
acctcggtgt gccgctgtta gcaatgggat gctattctca agtgaaccca acaactttga   7140
cagcatcctt agtcatgctt tcagtccatt atgcaataat aggtccagga ttgcaggcaa    7200
aagccacaag agaggcccag aaaaggacag ctgctgggat catgaaaaac cccacggtgg    7260
acgggataac agtaatagat ctagaaccaa tatcctatga cccaaaattt gaaaagcaat    7320
tagggcaggt catgctactc gtcttgtgtg ctggacaact actcttgatg agaacaacat    7380
gggcttctg tgaagtcttg actttggcca caggaccaat cttgaccttg tgggagggca    7440
acccgggaag gttttggaac acgaccatag ccgtatccac cgccaacatt ttcagggaa     7500
gttacctggc gggagctgga ctggcttttt cactcataaa gaatgyacaa accctagga    7560
ggggaactgg gaccacagga gagacactgg gagagaagtg gaagagacag ctaaactcat    7620
takacagaaa agagtttgaa gagtataaaa gaagtggaat actagaagtg gacaggactg    7680
aagccaagtc tgccctgaaa gatgggtcta aaatcaagca tgcagtatct agagggtcca    7740
gtaagattag atggattgtt gagagaggga tggtaaagcc aaaagggaaa gttgtagatc    7800
ttggctgtgg gagaggagga tggtcttatt acatggcgac gctcaagaac gtgactgaag    7860
tgaaagggta tacaaaagga ggtccaggac atgaagaacc gattcccatg gctacttatg    7920
gctggaattt ggtcaaactc cattcagggg ttgacgtgtt ctacaaaccc acagagcaag   7980
tggacaccct gctctgtgat attggggagt catcttctaa tccaacaata gaggaaggaa    8040
gaacattaag agtttttgaag atggtggagc catggctctc ttcaaaacct gaattctgca    8100
tcaaagtcct taacccctac atgccaacag tcatagaaga gctggagaaa ctgcagagaa    8160
aacatggtgg gaaccttgtc agatgcccgc tgtccaggaa ctccacccat gagatgtatt    8220
gggtgtcagg agcgtcggga aacattgtga gctctgtgaa cacaacatca aagatgttgt   8280
tgaacaggtt cacaacaagg cataggaaac ccacttatga aaggacgta gatcttgggg      8340
caggaacgag aagtgtctcc actgaaacag aaaaaccaga catgacaatt attgggagaa    8400
ggcttcagcg attgcaagag gagcacaaag aaacctggca ttatgatcag gaaaacccat    8460
acagaacctg ggcgtatcat ggaagctatg aagctccttc gacaggctct gcatcctcca    8520
tggtgaacgg ggtagtaaaa ctgctaacaa accttgggga tgtggttcca atggtgaccc    8580
agttagccat gacagacaca ccccttttg ggcaacaaag agtgttcaaa gagaaggtgg      8640
ataccagaac accacaacca aaacccggta cacgaatggt tatgaccacg acagccaatt    8700
ggctgtgggc cctccttggg aagaagaaaa atcccagact gtgcacaagg gaaagagttca    8760
tctcaaaagt tagatcaaac gcagccatag gcgcagtctt tcaggaagaa cagggatgga    8820
catcagccag tgaagctgtg aatgacagcc ggttttggga actggttgac aaagaaaggg    8880
ccctacacca ggaagggaaa tgtgaatcgt gtgtctacaa catgatggga aaacgtgaga    8940
aaaagtagg agagtttggc agagccaagg gaagccgagc aatctggtac atgtggctgg    9000
gagcgcggtt tctggaattt gaagccctgg gttttttgaa tgaagatcac tggtttggca    9060
gagaaaattc atggagtgga gtggaagggg aaggtctgca cagattggga tatatcctgg    9120
```

```
aggagataga caagaaggat ggagacctaa tgtatgctga tgacacagca ggctgggaca    9180
caagaatcac tgaggatgac cttcaaaatg aagaactgat cacggaacag atggcccccc    9240
accacaagat cctagccaaa gccattttca aactaaccta tcaaaacaaa gtggtgaaag    9300
tcctcagacc cacaccgaga ggagcggtga tggatatcat atccaggaaa gaccaaagag    9360
gtagtggaca agttggaaca tatggtttga acacattcac caacatggaa gttcaactca    9420
tccgccaaat ggaagctgaa ggagtcatca cacaagatga catgcagaac ccaaaagggt    9480
tgaaagaaag agttgagaaa tggctgaaag agtgtggtgt cgacaggtta aagaggatgg    9540
caatcagtgg agacgattgc gtggtgaagc ccctggatga gaggtttggc acttccctcc    9600
tcttcttgaa cgacatggga aaggtgagga aagacattcc gcagtgggaa ccatctaagg    9660
gatggaaaaa ctggcaagag gttccttttt gctcccacca ctttcacaag atcttcatga    9720
aggatggccg ctcactagtt gttccatgta gaaaccagga tgaactgata gggagagcca    9780
gaatctcgca gggggctgga tggagcttaa gagaaacagc ctgcctgggc aaagcttacg    9840
cccagatgtg gtcgctcatg tacttccaca gaagggatct gcgtttagcc tccatggcca    9900
tatgctcagc agttccaacg gaatggtttc caacaagcag aacaacatgg tcaatccacg    9960
ctcatcatca gtggatgacc actgaagata tgctcaaagt gtggaacaga gtgtggatag   10020
aagacaaccc taatatgact gacaagactc cagtccattc gtgggaagat ataccttacc   10080
tagggaaaag agaggatttg tggtgtggat ccctgattgg actttcttcc agagccacct   10140
gggcgaagaa cattcacacg gccataaccc aggtcagaaa cctgatcgga aaagaggaat   10200
acgtggatta catgccagta atgaaaagat acagcgctcc ttcagagagt gaaggagttc   10260
tgtaattacc aacaacaaac accaaaggct attgaagtca ggccacttgt gccacggctt   10320
gagcaaaccg tgctgcctgt agctccgcca ataatgggag gcgtgaaatc cctagggagg   10380
ccatgcgcca cggaagctgt acgcgtggca tattggacta gcggttagag gagacccctc   10440
ccatcactga caaaacgcag caaaagggg cccgaagcca ggaggaagct gtactcctgg    10500
tggaaggact agaggttaga ggagaccccc ccaacacaaa aacagcatat tgacgctggg   10560
aaagaccaga gatcctgctg tctctgcaac atcaatccag gcacagagcg aagcaagatg   10620
gattggtgtt gttgatccaa caggttct                                      10648
```